(12) United States Patent
Arterburn et al.

(10) Patent No.: US 7,884,131 B2
(45) Date of Patent: Feb. 8, 2011

(54) OXYLIPINS FROM LONG CHAIN POLYUNSATURATED FATTY ACIDS AND METHODS OF MAKING AND USING THE SAME

(75) Inventors: Linda Arterburn, Ellicott City, MD (US); William Barclay, Boulder, CO (US); Bindi Dangi, Elkridge, MD (US); James Flatt, Baltimore, MD (US); Jung Lee, McLean, VA (US); Mary Van Elswyk, Longmont, CO (US)

(73) Assignee: Martek Biosciences, Corporation, Columbia, MD (US)

( * ) Notice: Subject to any disclaimer, the term of this patent is extended or adjusted under 35 U.S.C. 154(b) by 486 days.

(21) Appl. No.: 11/284,790

(22) Filed: Nov. 21, 2005

(65) Prior Publication Data
US 2006/0241088 A1    Oct. 26, 2006

Related U.S. Application Data

(60) Provisional application No. 60/629,842, filed on Nov. 19, 2004, provisional application No. 60/729,038, filed on Oct. 21, 2005.

(51) Int. Cl.
*A61K 31/22* (2006.01)
*C07C 59/00* (2006.01)
*C07C 57/00* (2006.01)

(52) U.S. Cl. ............ 514/549; 514/165; 514/546; 514/560; 562/400; 562/579; 562/512; 554/82; 554/227; 554/230

(58) Field of Classification Search ............ 514/165, 514/546, 549, 560; 562/400, 512, 579; 554/82, 554/227, 230; 424/195.7, 489, 490
See application file for complete search history.

(56) References Cited

U.S. PATENT DOCUMENTS 5,102,670 A    4/1992 Abraham et al.

(Continued)

FOREIGN PATENT DOCUMENTS

CZ        281096    *  6/1996

(Continued)

OTHER PUBLICATIONS

Milks, M. et al., Metabolism of 4,7,10,13,16-docosapentaenoic acid by human platelet cyclooxygenase and lipoxygenase, 1985, Biochimica et Biophysica Acta, Lipids and Lipid Megabolism, 835(1), Abstract (HCAPLUS).*

(Continued)

*Primary Examiner*—Rosalynd Keys
*Assistant Examiner*—Yate' K Cutliff
(74) *Attorney, Agent, or Firm*—Sheridan Ross, P.C.

(57) ABSTRACT

Disclosed are novel oxylipins, referred to herein as docosanoids, that are derived from C22 polyunsaturated fatty acids, and method of making and using such oxylipins. Also disclosed is the use of docosapentaenoic acid (C22:5n-6) (DPAn-6), docosapentaenoic acid (C22:5n-3) (DPAn-3), and docosatetraenoic acid (DTAn-6: C22:4n-6) as substrates for the production of novel oxylipins, and to the oxylipins produced thereby. Also disclosed is the use of DPAn-6, DPAn-3, DTAn-6, and/or the oxylipins derived therefrom, and/or novel docosanoids derived from the structures of C22 fatty acids, in therapeutic and nutritional or cosmetic applications, and particularly as anti-inflammatory or anti-neurodegenerative compounds. The invention also relates to novel ways of producing long chain polyunsaturated acid (LCPUFA)-rich oils and compositions that contain enhanced and effective amounts of LCPUFA-derived oxylipins, and particularly, docosanoids.

7 Claims, 40 Drawing Sheets

U.S. PATENT DOCUMENTS

| | | | |
|---|---|---|---|
| 5,603,959 A * | 2/1997 | Horrobin et al. | 424/490 |
| 5,955,496 A | 9/1999 | Hammock et al. | |
| 6,174,695 B1 | 1/2001 | Hammock et al. | |
| 6,596,766 B1 | 7/2003 | Igarashi et al. | |
| 6,670,396 B2 * | 12/2003 | Serhan et al. | 514/549 |
| 6,777,211 B1 | 8/2004 | Saitoh et al. | |
| 6,887,901 B1 | 5/2005 | Serhan | |
| 6,949,664 B2 | 9/2005 | Petasis | |
| 7,041,485 B2 | 5/2006 | Bouarab et al. | |
| 7,045,143 B1 | 5/2006 | Sawatzki et al. | |
| 7,154,022 B2 | 12/2006 | Howe et al. | |
| 7,273,624 B2 | 9/2007 | Rosenberg et al. | |
| 2004/0048927 A1 | 3/2004 | Horrobin | |
| 2004/0166130 A1 | 8/2004 | Filippi et al. | |
| 2005/0106603 A1 | 5/2005 | Onuki et al. | |
| 2005/0228047 A1 | 10/2005 | Petasis | |
| 2007/0248586 A1 | 10/2007 | Arterburn et al. | |

FOREIGN PATENT DOCUMENTS

| | | |
|---|---|---|
| WO | WO 99/33355 | 7/1999 |
| WO | 01/34547 | 5/2001 |

OTHER PUBLICATIONS

VanRollins, M. et al., Oxidaiton of dicoshexaenoic acid by rat liver microsomes, 1984, Journal of Biological Chemistry, 259(9), Abstract (HCAPLUS).*

Oliw, E.H. et al., Metabolism of polyunsaturated fatty acids by an (n-6)-lipoxygenase associated with human ejaculates, 1989, Biochemica et Biophysica Acta, Lipids and Lipid Metabolism, 1002(3) Abstract (HCAPLUS.*

Karanian, J.W., et al., Inhibitory Effects of n-6 and n-3 Hydroxy Fatty Acids on Thromboxane 9U46619)-Induced Smooth Muscel Contraction, 1994, The journal of Pharmacology and Experimental Therapeutics, vol. 270, No. 3, pp. 1105-1109.*

Simopoulos, A.P., et al. Evolutinary aspects of diet, essential fatty acids and cardiovaxcular disease, 2001, European Heart Journal supplements, 3, (Supplement D), D8-D21.*

Bergholte et al., Archives of Biochemistry and Biophysics, Sep. 1987, vol. 257, No. 2, pp. 444-450.

Chavis et al., Biochemical and Biophysical Research Communications, vol. 207, No. 1, 1995, pp. 273-279.

Chavis et al., Biochemical Pharmacology, vol. 56, 1998, pp. 535-541.

Chavis et al., J. Exp. Med., Apr. 1996, vol. 183, pp. 1633-1643.

Costello et al., Annals of the Rheumatic Diseases, 1992, vol. 51, pp. 1215-1218.

Di Marzo et al., Biochem. J. (1994), Viol. 300, pp. 501-507.

Green et al., Lipids, 1990, vol. 25, No. 10, pp. 618-623.

Hamberg, J. Chem. Soc. Perkin Trans., 1993, pp. 3065-3072.

Jiang et al., Phytochemistry, 1991, vol. 30, No. 4, pp. 1187-1190.

Jubiz et al., Biochemical and Biophysical Research Communications, 1983, vol. 114, No. 2, pp. 855-862.

Knight et al., Biofouling, 1999, vol. 14(3), pp. 213-217.

Knight et al., J. Mar. Biol., Ass. U.K., 2000, vol. 80, pp. 113-117.

Lam et al., "Transformation of 15-Hydroperoxyeicosapentaenoic Acid Into Mono and Dihydroxyeicosapentaenoic Acids by Human Platelets", Life Sciences, 1985, vol. 95, ISSN: 0258-1213 pp. 167-180.

Lam et al., Biochimica et Biophysica Acta, 1987, vol. 917, pp. 398-405.

Maas et al., Proc. Natl. Acad. Sci. USA, May 1983, vol. 80, pp. 2884-2888.

Mancini et al., Helvetica Chimica Acta, 1999, vol. 82, pp. 677-684.

Mitchell et al. "Inhibition of platelet 12-lipoxygenase by hydroxy-fatty acids", Biochemical Society Transactions, 607th Meeting, London, 1984, pp. 839-841.

Nicolaou et al., J. Am. Chem. Soc., 1984, vol. 106, pp. 5734-5736.

Petrich et al., Biochem. J. (1996) vol. 314, pp. 911-916.

Rabinovitch et al., Agents and Actions, 1981, vol. 11, 617, pp. 580-583.

Rowley et al., Biochemistry, 1994, vol. 33, pp. 856-863.

Sirois et al., Prostaglandins, Sep. 1982, vol. 24, No. 3, pp. 405-418.

Sok et al., Korean Biochem. J., 1988, vol. 21, No. 4, pp. 512-518.

Sprecher et al., Prostaglandins, Leukotrienes and Medicine, 1986, vol. 23, pp. 129-134.

Thomas et al., Inflamm Res., 19995, vol. 44, pp. 121-124.

Tori et al., Molecules, 2003, vol. 8, pp. 882-885.

VanRollins et al., Biocimica et Biophysica Acta, 1985, vol. 833, pp. 272-280.

Woolard et al., Journal of Chromatography, 1984, vol. 306, pp. 1-21.

Yamane et al., Journal of Chromatography, 1992, vol. 579, pp. 25-36.

Hong et al., "Novel Docosatrienes and 17S-Resolvins Generated from Docosahexaenoic Acid in Murine Brain, Human Blood, and Glial Cells", The Journal of Biological Chemistry, vol. 278, No. 17, Apr. 25, 2003, pp. 14677-14687.

Marcheselli et al., "Novel Docosanoids Inhibit Brain Ischemia-Reperfusion-mediated Leukocyte Infiltration and Pro-inflammatory Gene Expression", The Journal of Biological Chemistry, vol. 278, No. 44, Oct. 31, 2003, pp. 43807-43817.

Oliw et al., "Metabolism of polyunsaturated fatty acids by an (n-6)-lipoxygenase associated with human ejaculates", Biochimica et Biophysica Acta, 1002 (1989), pp. 283-291.

Serhan et al., "Resolvins: A Family of Bioactive Products of Omega-3 Fatty Acid Transformation Circuits Initiated by Aspirin Treatment that Counter Proinflammation Signals", J. Exp. Med., vol. 196, No. 8, Oct. 21, 2002, pp. 1025-1037.

International Search Report for International (PCT) Patent Application No. PCT/US2005/042462, mailed Aug. 14, 2006.

Written Opinion for International (PCT) Patent Application No. PCT/US2005/042462, mailed Aug. 14, 2006.

International Preliminary Report on Patentability for International (PCT) Patent Application No. PCT/US2005/042462, mailed May 31, 2007.

Coffa et al., Lipids, vol. 35, No. 11, 2000, pp. 1195-1204.

Senger et al., The Journal of Biological Chemistry, vol. 280, No. 9, Mar. 4, 1005, pp. 758-7596.

Bouarab et al. "The Innate Immunity of a Marine Red Alga Involves Oxyllpins from Both the Eicosanold and Octadecanoid Pathways", Plant Physiology, Jul. 2004, vol. 135, pp. 1838-1848.

International Search Report for International (PCT) Patent Application No. PCT/US07/61397, mailed Apr. 29, 2008.

Written Opinion for International (PCT) Patent Application No. PCT/US07/61397, mailed Apr. 29, 2008.

U.S. Appl. No. 12/162,945, filed Jan. 31, 2007, Arterburn et al.

Greiner et al., Lipids, 2003, vol. 38(4), pp. 431-435.

Hoshino et al., Agricultural and Biological Chemistry, 1990, vol. 54(6), pp. 1459-1467.

Moriguchi et al., Journal of Lipid Research, 2001, vol. 42, pp. 419-427.

Official Action for U.S. Appl. No. 11/669,730, mailed Sep. 22, 2008.

International Search Report for International (PCT) Patent Application No. PCT/US08/54456, mailed Aug. 6, 2008.

Written Opinion for International (PCT) Patent Application No. PCT/US08/54456, mailed Aug. 6, 2008.

International Preliminary Report on Patentability for International (PCT) Patent Application No. PCT/US07/61397, mailed Aug. 14, 2008.

U.S. Appl. No. 12/357,388, filed Jan. 21, 2009, Dangi.

"Fatty acids—good for the brain, good for Alzheimer disease", vol. 115, No. 10, Oct. 2005, p. 2585.

Arita et al. "Resolvin E1, an endogenous lipid mediator derived from omega-3 eicosapentaenoic acid, protects against 2,4,6-trinitrobenzene sulfonic acid-induced colitis", PNAS May 24, 2005, vol. 102, No. 21, 7671-7676.

Arita et al. "The contributions of aspirin and microbial oxygenase to the biosynthesis of anti-inflammatory resolvins: Novel oxygenase products from x-3 polyunsaturated fatty acids", Biochemical and Biophysical Research Communications 336 (2005), 9 pages.

Arita et al., "Stereochemical assignment, antiinflammatory properties, and receptor for the omega-3 lipid mediator resolvin E1", JEM vol. 201, No. 5, Mar. 7, 2005 713-722.

Bannenberg et al. "Molecular Circuits of Resolution: Formation and Actions of Resolvins and Protectins", The Journal of Immunology, 2005, pp. 4345-4355.

Belayev et al., "Docosahexaenoic Acid Complexed to Albumin Elicits High-Grade Ischemic Neuroprotection", Stroke, Jan. 2005, pp. 118-123.

Butovich "On the Structure, Synthesis and Mechanism of Formation Ofneuroprotectin D1—A Novel Anti-Nflammatory Compound of Docosahexaenoic Acid Family", Department of Ophthalmology, University of Texas Southwestern Medical Center, Dallas, TX 75390-9057, 2005, 17 pages.

Butovich et al. "Novel Oxylipins Formed from Docosahexaenoic Acid by Potato Lipoxygenase-10(S)-Hydroxydocosahexaenoic Acid and 10,20-Dihydroxydocosahexaenoic Acid" Lipids, vol. 40, No. 3, 2005, pp. 249-257.

Chen et al. "Lipid signaling: Sleep, synaptic plasticity, and neuroprotection", Prostaglandins & other Lipid Mediators 77 (2005) 65-76.

Flower et al., "Controlling inflammation: a fat chance?", JEM, vol. 201, No. 5, Mar. 7, 2005 671-674.

Jiang et al., "5-Lipoxygenase-derived oxylipins from the red alga Rhodymenia pertusa" Phytochemistry 53 (2000) 129-133.

Kumon et al., "A new labyrinthulid isolate, which solely produces n-6 docosapentaenoic acid", Appl. Microbiol Biotechnol, 2003, vol. 63, pp. 22-28.

Lukiw et al. "A role for docosahexaenoic acid—derived neuroprotectin D1 in neural cell survival and Alzheimer disease", The Journal of Clinical Investigation, vol. 115, No. 10, Oct. 2005, pp. 2774-2783.

Mukherjee et al., "Neuroprotectin D1: A docosahexaenoic acid-derived docosatriene protects human retinal pigment epithelial cells from oxidative stress", PNAS, Jun. 1, 2004, vol. 101, No. 22, pp. 8491-8496.

Napier et al. "The production of very-long-chain PUFA biosynthesis in transgenic plants: towards a sustainable source of fish oils", Proceedings of the Nutrition Society (2005), 64, 387-393.

Robert et al., "Metabolic engineering of Arabidopsisto produce nutritionally important DHA in seed oil", Functional Plant Biology, 2005, 32, pp. 473-479.

Rorrer et al. "Bioreactor seaweed cell culture for production of bioactive oxylipins", Journal of Applied Phycology (Historical Archive), vol. 7, Issue 2, Apr 1995, pp. 187-198.

Rorrer et al. "Development and Bioreactor Cultivation of a Novel Semidifferentiated Tissue Suspension Derived from the Marine Plant Acrosiphonia coalita", Biotechnology and Bioengineering, vol. 49, pp. 559-567 (1996).

Rorrer et al., "Production of Hydroxy Fatty Acids by Cell Suspension Cultures of the Marine Brown Alga Laminaria Saccharina", Phytochemistry, vol. 46, No. 5, 1997, pp. 871-877.

Serhan et al. "Resolvins, docosatrienes, and neuroprotectins, novel omega-3-derived mediators, and their aspirin-triggered endogenous epimers: an overview of their protective roles in catabasis", Prostaglandins & other Lipid Mediators 73 (2004) 155-172.

VanRollins et al, "Oxidation of dicoshexaenoic acid by rat liveer microsomes", 1984, Journal of Biological Chemistry, vol. 259, No. 9, Issue of May 10,1984, pp. 5776-5783.

Gardner et al., "Lipoxygenase as a Versatile Biocatalyst", Journal of American Oil Chemist's Society, vol. 73, No. 11, 1986, pp. 1347-1357.

U.S. Appl. No. 12/531,344, filed Sep. 15, 2009, Arterburn et al.

Wheelean et al., Metabolism of Lukotriene B4 in cultured hepatoma cells, Aug. 20, 1995, Archives of Biochemistry and Biophysics, vol. 321, No. 2, pp. 381-389.

Kobayashi et al., Important contribution of the methylene part of LTB4 toward binding affinity to the LTB$ receptors and rise in intracellular-free calcium concentration, 1994, Biochimica et Biophysica Acta, vol. 1215(3), pp. 280-284.

International Preliminary Report on Patentability for International (PCT) Patent Application No. PCT/US08/54456, mailed Sep. 3, 2009.

Official Action for U.S. Appl. No. 11/669,730, mailed Sep. 24, 2009.

"Chemical and Biological Characterization of Two Omega-6 Docosapentaenoic Acid (DPAn-6)-derived Oxylipins Involved in the Resolution of Inflammation: 17-hydroxy DPAn-6 and 10, 17-dihydroxy DPAn-6." Martek Biosciences Corporation. 40 pages. Oct. 1, 2008.

* cited by examiner

Fig. 7

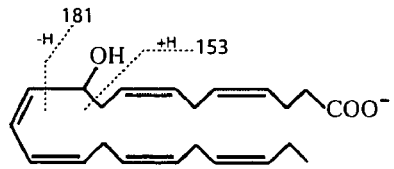

10-hydroxy DHA

| 343 | [M-H] |
| 325 | [M-H]-$H_2O$ |
| 299 | [M-H]-$CO_2$ |
| 281 | [M-H]-$CO_2$-$H_2O$ |
| 181 | fragment |
| 153 | fragment |
| 137 | 181-$CO_2$ |

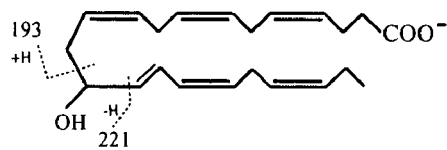

13-hydroxy DHA

| 343 | [M-H] |
| 325 | [M-H]-$H_2O$ |
| 299 | [M-H]-$CO_2$ |
| 281 | [M-H]-$CO_2$-$H_2O$ |
| 193 | fragment |
| 221 | fragment |

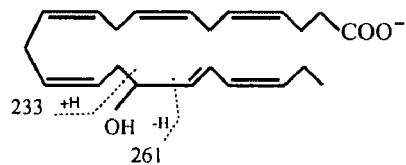

16-hydroxy DHA

| 343 | [M-H] |
| 325 | [M-H]-$H_2O$ |
| 299 | [M-H]-$CO_2$ |
| 281 | [M-H]-$CO_2$-$H_2O$ |
| 233 | fragment |
| 261 | fragment |
| 189 | 233-$CO_2$ |

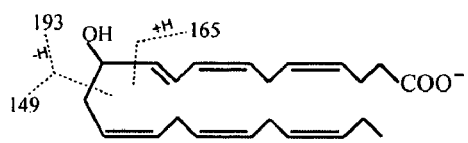

11-hydroxy DHA

| 343 | [M-H] |
| 325 | [M-H]-$H_2O$ |
| 299 | [M-H]-$CO_2$ |
| 281 | [M-H]-$CO_2$-$H_2O$ |
| 193 | fragment |
| 149 | fragment |
| 165 | fragment |
| 121 | 165-$CO_2$ |

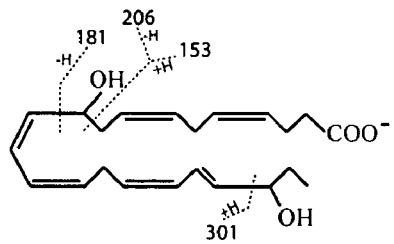

10, 20- dihydroxy DHA

| 359 | [M-H] |
| 341 | [M-H]-$H_2O$ |
| 315 | [M-H]-$CO_2$ |
| 297 | [M-H]-$CO_2$-$H_2O$ |
| 279 | [M-H]-$CO_2$-2$H_2O$ |
| 181 | fragment |
| 206 | fragment |
| 153 | fragment |
| 257 | 301-$CO_2$ |
| 239 | 301-$CO_2$-$H_2O$ |
| 137 | 181-$CO_2$ |

10-hydroxy DPAn-6

| 345 | [M-H] |
| 327 | [M-H]-H2O |
| 301 | [M-H]-CO2 |
| 283 | [M-H]-CO2-H2O |
| 181 | fragment |
| 153 | fragment |
| 137 | 181-CO2 |

Fig. 9
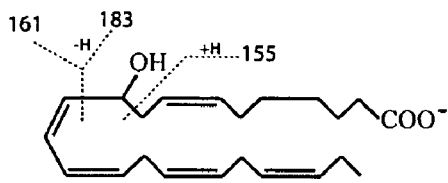
10-hydroxy DPAn-3
| 345 | [M-H] |
| 327 | [M-H]-H2O |
| 301 | [M-H]-CO2 |
| 283 | [M-H]-CO2-H2O |
| 183 | fragment |
| 155 | fragment |
| 161 | fragment |
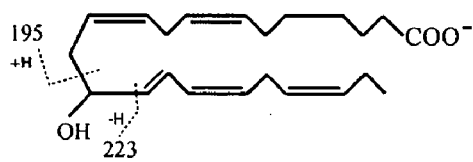
13-hydroxy DPAn-3
| 345 | [M-H] |
| 327 | [M-H]-H2O |
| 301 | [M-H]-CO2 |
| 283 | [M-H]-CO2-H2O |
| 195 | fragment |
| 223 | fragment |
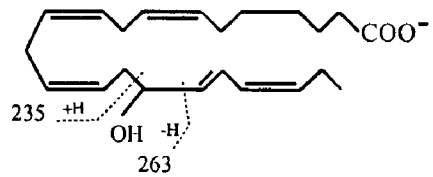
16-hydroxy DPAn-3
| 345 | [M-H] |
| 327 | [M-H]-H2O |
| 301 | [M-H]-CO2 |
| 283 | [M-H]-CO2-H2O |
| 235 | fragment |
| 263 | fragment |
| 191 | 235-CO2 |
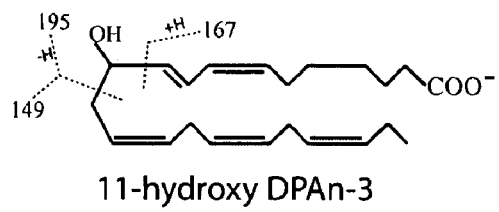
11-hydroxy DPAn-3
| 345 | [M-H] |
| 327 | [M-H]-H2O |
| 301 | [M-H]-CO2 |
| 283 | [M-H]-CO2-H2O |
| 195 | fragment |
| 149 | fragment |
| 167 | fragment |
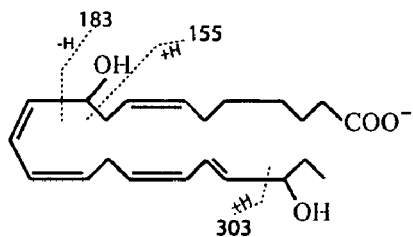
10, 20 dihydroxy DPAn-3
| 361 | [M-H] |
| 343 | [M-H]-H2O |
| 317 | [M-H]-CO2 |
| 299 | [M-H]-CO2-H2O |
| 183 | fragment |
| 155 | fragment |
| 303 | fragment |

Fig. 10
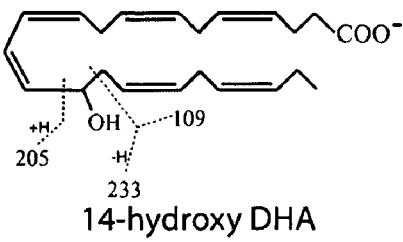
14-hydroxy DHA
| 343 | [M-H] |
| 325 | [M-H]-H2O |
| 299 | [M-H]-CO2 |
| 281 | [M-H]-CO2-H2O |
| 233 | fragment |
| 205 | fragment |
| 109 | fragment |
| 161 | 205-CO2 |
| 189 | 233-CO2 |
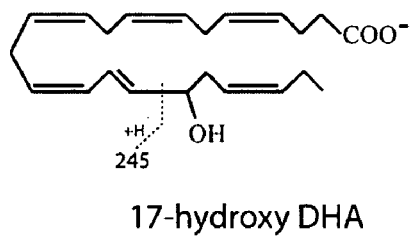
17-hydroxy DHA
| 343 | [M-H] |
| 325 | [M-H]-H2O |
| 299 | [M-H]-CO2 |
| 281 | [M-H]-CO2-H2O |
| 245 | fragment |
| 201 | 245-CO2 |
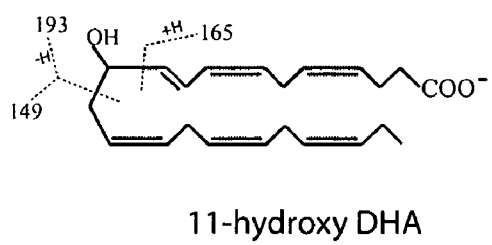
11-hydroxy DHA
| 343 | [M-H] |
| 325 | [M-H]-H2O |
| 299 | [M-H]-CO2 |
| 281 | [M-H]-CO2-H2O |
| 149 | fragment |
| 165 | fragment |
| 193 | fragment |
| 121 | 165-CO2 |
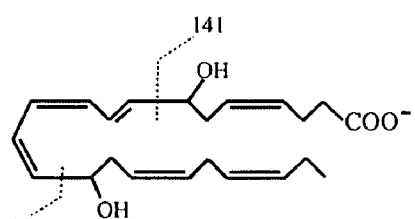
7,14-dihydroxy DHA
| 359 | [M-H] |
| 341 | [M-H]-H2O |
| 315 | [M-H]-CO2 |
| 297 | [M-H]-CO2-H2O |
| 279 | [M-H]-CO2-2H2O |
| 221 | fragment |
| 141 | fragment |
| 177 | 221-CO2 |
| 203 | 221-H2O |
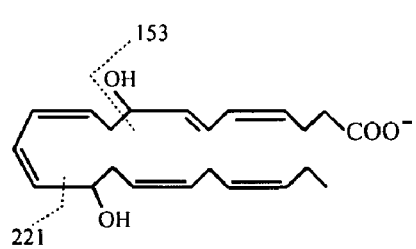
8,14-dihydroxy DHA
| 359 | [M-H] |
| 341 | [M-H]-H2O |
| 315 | [M-H]-CO2 |
| 297 | [M-H]-CO2-H2O |
| 279 | [M-H]-CO2-2H2O |
| 221 | fragment |
| 153 | fragment |

Fig. 11

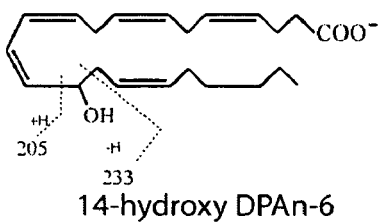

14-hydroxy DPAn-6

| 345 | [M-H] |
|---|---|
| 327 | [M-H]-$H_2O$ |
| 301 | [M-H]-$CO_2$ |
| 283 | [M-H]-$CO_2$-$H_2O$ |
| 233 | fragment |
| 205 | fragment |
| 161 | 205-$CO_2$ |
| 189 | 233-$CO_2$ |

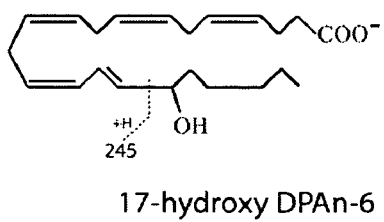

17-hydroxy DPAn-6

| 345 | [M-H] |
|---|---|
| 327 | [M-H]-$H_2O$ |
| 301 | [M-H]-$CO_2$ |
| 283 | [M-H]-$CO_2$-$H_2O$ |
| 245 | fragment |
| 201 | 245-$CO_2$ |

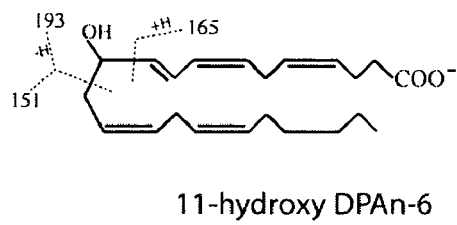

11-hydroxy DPAn-6

| 345 | [M-H] |
|---|---|
| 327 | [M-H]-$H_2O$ |
| 301 | [M-H]-$CO_2$ |
| 283 | [M-H]-$CO_2$-$H_2O$ |
| 151 | fragment |
| 165 | fragment |
| 193 | fragment |
| 121 | 165-$CO_2$ |

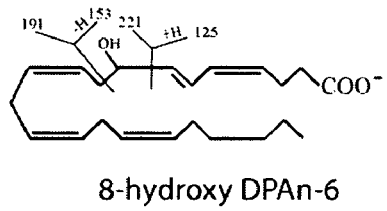

8-hydroxy DPAn-6

| 345 | [M-H] |
|---|---|
| 327 | [M-H]-$H_2O$ |
| 301 | [M-H]-$CO_2$ |
| 283 | [M-H]-$CO_2$-$H_2O$ |
| 153 | fragment |
| 191 | fragment |
| 135 | 153-$H_2O$ |

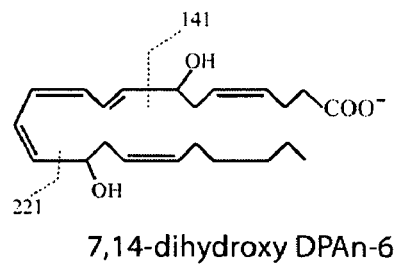

7,14-dihydroxy DPAn-6

| 361 | [M-H] |
|---|---|
| 343 | [M-H]-$H_2O$ |
| 317 | [M-H]-$CO_2$ |
| 299 | [M-H]-$CO_2$-$H_2O$ |
| 281 | [M-H]-$CO_2$-2$H_2O$ |
| 221 | fragment |
| 141 | fragment |
| 177 | 221-$CO_2$ |
| 203 | 221-$H_2O$ |

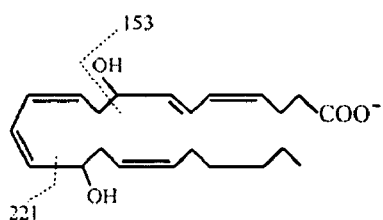

8,14-dihydroxy DPAn-6

| 361 | [M-H] |
|---|---|
| 343 | [M-H]-$H_2O$ |
| 317 | [M-H]-$CO_2$ |
| 299 | [M-H]-$CO_2$-$H_2O$ |
| 281 | [M-H]-$CO_2$-2$H_2O$ |
| 221 | fragment |
| 153 | fragment |
| 203 | 221-$H_2O$ |

Fig. 12
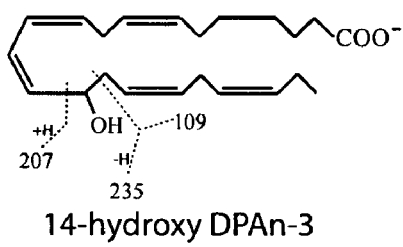
14-hydroxy DPAn-3
| 345 | [M-H] |
|---|---|
| 327 | [M-H]-$H_2O$ |
| 301 | [M-H]-$CO_2$ |
| 283 | [M-H]-$CO_2$-$H_2O$ |
| 235 | fragment |
| 207 | fragment |
| 109 | fragment |
| 163 | 205-$CO_2$ |
| 191 | 233-$CO_2$ |
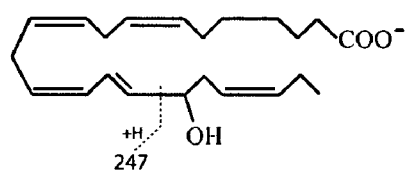
17-hydroxy DPAn-3
| 345 | [M-H] |
|---|---|
| 327 | [M-H]-$H_2O$ |
| 301 | [M-H]-$CO_2$ |
| 283 | [M-H]-$CO_2$-$H_2O$ |
| 247 | fragment |
| 203 | 245-$CO_2$ |
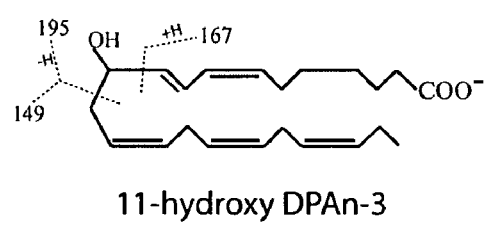
11-hydroxy DPAn-3
| 345 | [M-H] |
|---|---|
| 327 | [M-H]-$H_2O$ |
| 301 | [M-H]-$CO_2$ |
| 283 | [M-H]-$CO_2$-$H_2O$ |
| 149 | fragment |
| 167 | fragment |
| 195 | fragment |
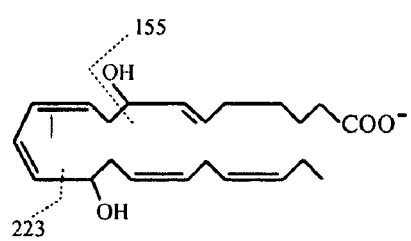
8,14-dihydroxy DPAn-3
| 361 | [M-H] |
|---|---|
| 343 | [M-H]-$H_2O$ |
| 317 | [M-H]-$CO_2$ |
| 299 | [M-H]-$CO_2$-$H_2O$ |
| 281 | [M-H]-$CO_2$-2$H_2O$ |
| 223 | fragment |
| 155 | fragment |
| 137 | 155-$CO_2$ |
| 205 | 223-$H_2O$ |

OXYLIPINS FROM LONG CHAIN POLYUNSATURATED FATTY ACIDS AND METHODS OF MAKING AND USING THE SAME

CROSS-REFERENCE TO RELATED APPLICATIONS

This application claims the benefit of priority from U.S. Provisional Application Ser. No. 60/629,842, filed Nov. 19, 2004, and from U.S. Provisional Application Ser. No. 60/729,038, filed Oct. 21, 2005. The entire disclosure of each of U.S. Provisional Application Ser. No. 60/629,842, filed Nov. 19, 2004, and U.S. Provisional Application Ser. No. 60/729,038 is incorporated herein by reference.

FIELD OF THE INVENTION

This invention generally relates to the use of docosapentaenoic acid (C22:5n-6) (DPAn-6), docosapentaenoic acid (C22:5n-3) (DPAn-3), and docosatetraenoic acid (DTAn-6: C22:4n-6) as substrates for the production of novel oxylipins, and to the oxylipins produced thereby. The invention further relates to the use of DPAn-6, DPAn-3, DTAn-6, and/or the oxylipins derived therefrom, particularly as anti-inflammatory compounds. The invention also relates to novel ways of producing long chain polyunsaturated acid (LCPUFA)-rich oils and compositions that contain enhanced and effective amounts of LCPUFA-derived oxylipins, and particularly, docosanoids.

BACKGROUND OF THE INVENTION

Researchers in the 1990s identified hydroxy derivatives of some fatty acids in macroalgae (seaweeds) and described the possible role of these compounds in wound healing and cell signaling in the organisms (Gerwick & Bemart 1993; Gerwick et al 1993; Gerwick 1994). They recognized these compounds to be similar to those produced in the human body through the lipoxygenase pathway. These same researchers also attempted to develop cell suspension cultures of these seaweeds to produce eicosanoids and related oxylipins from C18 fatty acids (linoleic acid, and linolenic acid) and arachidonic acid (C20:4n-6) (ARA) in the red, brown and green seaweeds. However, production of seaweed biomass in these cultures systems proved to be very poor (e.g. about 0.6 to 1.0 g/L seaweed biomass after 15 days (Rorrer et al. 1996)) and even direct addition of key fatty acids to the cultures only minimally increased production of oxylipins over that of controls (Rorrer et al. 1997). Additionally, in some cases, the added free fatty acids proved toxic to the cultures (Rorrer et al. 1997). Therefore these systems have only remained academically interesting for producing oxygenated forms of these fatty acids, and studies continue on the C18 and C20 oxylipins in these seaweeds (e.g., Bouarab et al. 2004).

The oxylipins from the long chain omega-6 (n-6 or ω-6 or N6) fatty acid, ARA, have been well studied and are generally considered to be proinflammatory in humans. Oxylipins from the long chain omega-3 (n-3 or ω-3 or N3) fatty acids, however, have generally been found to be anti-inflammatory. In the early 2000's, Serhan and other researchers discovered that hydroxylated forms of two long chain omega-3 polyunsaturated fatty acids (omega-3 LCPUFAs) (i.e., eicosapentaenoic acid (C20:5, n-3) (EPA) and docosahexaenoic acid C22:6, n-3) (DHA)) were made in the human body (Serhan et al. 2004a,b; Bannenberg et al. 2005a,b) They identified pathways whereby the omega-3 (n-3 or ω-3) LCPUFAs, EPA and DHA, were processed by cyclooxygenases, acetylated cyclooxygenase-2 or by lipoxygenase enzymes, resulting in production of novel mono-, di- and tri-hydroxy derivatives of these fatty acids. The resulting compounds, which were named "resolvins" (because they were involved in the resolution phase of acute inflammation) or docosatrienes (because they were made from docosahexaenoic acid and contain conjugated double bonds), were determined to have strong anti-inflammatory (Arita et al. 2005a,b,c; Flower & Perretti 2005; Hong et al. 2003; Marcjeselli et al. 2003; Ariel et al. 2005), antiproliferative, and neuroprotective (Bazan 2005a,b; Bazan et al. 2005; Belayev et al. 2005; Butovich et al. 2005; Chen & Bazan 2005; Lukiw et al. 2005; Mukherjee et al 2004) properties. These compounds were also noted to have longer half-lives in the human body as compared to other types of eicosanoids.

In the past few years, various patents and patent application publications have described analogs of hydroxy derivatives of ARA, DHA and EPA, the pathways by which they are formed, methods for their synthesis in the laboratory via organic synthetic means or through biogenesis using cyclooxygenase or lipoxygenase enzymes, and use of these hydroxy derivatives as pharmaceutical compounds for the treatment of inflammatory diseases. These patents and publications are summarized briefly below.

U.S. Pat. No. 4,560,514 describes the production of both pro-inflammatory (LX-A) and anti-inflammatory tri-hydroxy lipoxins (LX-B) derived from arachidonic acid (ARA). Use of these compounds in both studying and preventing inflammation (as pharmaceutical compounds) are also described.

U.S. Patent Application Publication No. 2003/0166716 describes the use of lipoxins (derived from ARA) and aspirin-triggered lipoxins in the treatment of asthma and inflammatory airway diseases. Chemical structures of various anti-inflammatory lipoxin analogs are also taught.

U.S. Patent Application Publication No. 2003/0236423 discloses synthetic methods based on organic chemistry for preparing trihydroxy polyunsaturated eicosanoids and their structural analogs including methods for preparing derivatives of these compounds. Uses for these compounds and their derivatives in the treatment of inflammatory conditions or undesired cell proliferation are also discussed.

PCT Publication No. WO 2004/078143 is directed to methods for identifying receptors that interact with di- and tri-hydroxy EPA resolving analogs.

U.S. Patent Application Publication No. 2004/0116408A1 discloses that the interaction of EPA or DHA in the human body with cyclooxygenase-II (COX2) and an analgesic such as aspirin leads to the formation of di- and tri-hydroxy EPA or DHA compounds with beneficial effects relating to inflammation. It also teaches methods of use and methods of preparing these compounds.

U.S. Patent Application Publication No. 2005/0075398A1 discloses that the docosatriene 10,17S-docosatriene (neuroprotectin D1) appears to have neuroprotective effects in the human body.

PCT Publication No. WO 2005/089744A2 teaches that di- and tri-hydroxy resolvin derivatives of EPA and DHA and stable analogs thereof are beneficial in the treatment of airway diseases and asthma.

While the references above describe lipoxins derived from ARA and docosatrienes and resolvins derived from DHA and EPA, as well as various applications of such compounds, there remains a need in the art for alternative ways of delivering the anti-inflammatory benefits and other benefits of these LCPUFA oxylipins (and in particular docosanoids) to consumers other than by providing consumers with combinations of LCPUFA oil and aspirin or by chemically synthesizing these derivatives or their analogs.

Moreover, none of the references above describe methods for making these specific compounds in microbial cultures or plants, nor do they describe methods for increasing the content of these beneficial hydroxy fatty acid derivatives in edible oils. In addition, none of these references describe any hydroxy derivatives from other LCPUFAs, nor do any of these references suggest that that there could be a beneficial role for hydroxy derivatives of any LCPUFAs other than ARA, DHA and EPA.

SUMMARY OF THE INVENTION

One embodiment of the present invention generally relates to an isolated docosanoid of docosapentaenoic acid (DPAn-6). Such a docosanoid can include, but is not limited to, an R- or S-epimer of a docosanoid selected from: monohydroxy derivatives of DPAn-6, dihydroxy derivatives of DPAn-6, and tri-hydroxy derivatives of DPAn-6. Such a docosanoid can more particularly include, but is not limited to, an R- or S-epimer of a docosanoid selected from: 7-hydroxy DPAn-6; 8-hydroxy DPAn-6; 10-hydroxy DPAn-6; 11-hydroxy DPAn-6; 13-hydroxy DPAn-6; 14-hydroxy DPAn-6; 17-hydroxy DPAn-6; 7,17-dihydroxy DPAn-6; 10,17-dihydroxy DPAn-6; 13,17-dihydroxy DPAn-6; 7,14-dihydroxy DPAn-6; 8,14-dihydroxy DPAn-6; 16,17-dihdroxy DPAn-6; 4,5-dihydroxy DPAn-6; 7,16,17-trihydroxy DPAn-6; and 4,5,17-trihydroxy DPAn-6; or an analog, derivative or salt thereof.

Another embodiment of the present invention relates to an isolated docosanoid of docosapentaenoic acid (DPAn-3). Such a docosanoid can include, but is not limited to, an R- or S-epimer of a docosanoid selected from: monohydroxy derivatives of DPAn-3, dihydroxy derivatives of DPAn-3, and tri-hydroxy derivatives of DPAn-3. Such a docosanoid can more particularly include, but is not limited to, an R- or S-epimer of a docosanoid selected from: 7-hydroxy DPAn-3; 10-hydroxy DPAn-3; 11-hydroxy DPAn-3; 13-hydroxy DPAn-3; 14-hydroxy DPAn-3; 16-hydroxy DPAn-3; 17-hydroxy DPAn-3; 7,17-dihydroxy DPAn-3; 10,17-dihydroxy DPAn-3; 8,14-dihydroxy DPAn-3; 16,17-dihydroxy DPAn-3; 13,20-dihydroxy DPAn-3; 10,20-dihydroxy DPAn-3; and 7,16,17-trihydroxy DPAn-3; or an analog, derivative or salt thereof.

Yet another embodiment of the present invention relates to an isolated docosanoid of docosatetraenoic acid (DTAn-6). Such a docosanoid can include, but is not limited to, an R- or S-epimer of a docosanoid selected from: monohydroxy derivatives of DTAn-6, dihydroxy derivatives of DTAn-6, and tri-hydroxy derivatives of DTAn-6. Such a docosanoid can more particularly include, but is not limited to, an R- or S-epimer of a docosanoid selected from: 7-hydroxy DTAn-6; 10-hydroxy DTAn-6; 13-hydroxy DTAn-6; 17-hydroxy DTAn-6; 7,17-dihydroxy DTAn-6; 10,17-dihydroxy DTAn-6; 16,17-dihydroxy DTAn-6; and 7,16,17-trihydroxy DTAn-6; or an analog, derivative or salt thereof.

Another embodiment of the present invention relates to an isolated docosanoid of a C22 polyunsaturated fatty acid, wherein the docosanoid is an R- or S-epimer of a docosanoid selected from: 4,5-epoxy-17-hydroxy DPA; 7,8-epoxy DHA; 10,11-epoxy DHA; 13,14-epoxy DHA; 19,20-epoxy DHA; 13,14-dihydroxy DHA; 16,17-dihydroxy DTAn-6; 7,16,17-trihydroxy DTAn-6; 4,5,17-trihydroxy DTAn-6; 7,16,17-trihydroxy DTAn-3; 16,17-dihydroxy DTAn-3; 16,17-dihydroxy DTRAn-6; 7,16,17-trihydroxy DTRAn-6; 4,5-dihydroxy DTAn-6; and 10,16,17-trihydroxy DTRAn-6; or an analog, derivative or salt thereof.

Another embodiment of the invention relates to a composition comprising at least one of any of the above-described docosanoids. The composition includes, but is not limited to, a therapeutic composition, a nutritional composition or a cosmetic composition. In one aspect, the composition further comprises aspirin. In another aspect, the composition further comprises a compound selected from: DPAn-6, DPAn-3, DTAn-6, DHA, EPA, an oxylipin derivative of DHA and an oxylipin derivative of EPA. In another aspect, the composition further comprises at least one agent selected from: a statin, a non-steroidal anti-inflammatory agent, an antioxidant, and a neuroprotective agent. In another aspect, the composition further comprises a pharmaceutically acceptable carrier. In yet another aspect, the composition comprises an oil selected from: a microbial oil, a plant seed oil, and an aquatic animal oil.

Yet another embodiment of the present invention relates to an oil comprising at least about 10 µg of docosanoid per gram of oil. Other embodiments include an oil comprising at least about 20 µg of docosanoid per gram of oil, at least about 50 µg of docosanoid per gram of oil, or at least about 100 µg of docosanoid per gram of oil. In one aspect, the docosanoid in the above-identified oil is a polyunsaturated fatty acid selected from: docosatetraenoic acid (DTAn-6), docosapentaenoic acid (DPAn-6), docosapentaenoic acid (DPAn-3), docosahexaenoic acid (DHA), and eicosapentaenoic acid (EPA). In another aspect, the docosanoid is from a polyunsaturated fatty acid selected from: docosatetraenoic acid (DTAn-6), docosapentaenoic acid (DPAn-6), and docosapentaenoic acid (DPAn-3). In one aspect, the docosanoid is any of the above-identified docosanoids. The oil can include, but is not limited to, a microbial oil, a plant seed oil, and an aquatic animal oil.

Another embodiment of the invention includes a composition comprising any of the above-described oils, which can include, but is not limited to, a therapeutic composition, a nutritional composition or a cosmetic composition.

Yet another embodiment of the present invention relates to a composition comprising a long chain polyunsaturated fatty acid selected from: DPAn-6, DPAn-3, and DTAn-6 and a pharmaceutically or nutritionally acceptable carrier. In one aspect, the composition further comprises aspirin. In another aspect, the composition further comprises an enzyme that catalyzes the production of the docosanoids from DPAn-6, DTAn-6 or DPAn-3.

Another embodiment of the present invention relates to a method to prevent or reduce at least one symptom of inflammation or neurodegeneration in an individual. The method includes the step of administering to an individual at risk of, diagnosed with, or suspected of having inflammation or neurodegeneration or a condition or disease related thereto, an agent selected from the group consisting of: DPAn-6, DPAn-3, an oxylipin derivative of DPAn-6, and an oxylipin derivative of DPAn-3, to reduce at least one symptom of inflammation or neurodegeneration in the individual. In one aspect, the agent is effective to reduce the production of tumor necrosis factor-α (TNF-α) by T lymphocytes. In another aspect, the agent is effective to reduce the migration of neutrophils and macrophages into a site of inflammation. In another aspect, the agent is effective to reduce interleukin-1β (IL-1β) production in the individual. In yet another aspect, the agent is effective to reduce macrophage chemotactic protein-1 (MCP-1) in the individual. The oxylipin derivative used in the present method can include any of the above-identified docosanoids of the present invention. In one preferred embodiment, the agent is selected from: 17-hydroxy DPAn-6 and 10,17-dihydroxy DPAn-6, or a derivative or analog or salt thereof. In another embodiment, the agent is selected from: DPAn-6 and DPAn-3.

In one aspect, the method further includes administering at least one long chain omega-3 fatty acid and/or oxylipin derivative thereof to the individual. Such an omega-3 fatty acid can include, but is not limited to, DHA and/or EPA.

In one aspect, the DPAn-6 or DPAn-3 is provided in one of the following forms: as triglyceride containing DPAn-6 or DPAn-3, as a phospholipid containing DPAn-6 or DPAn-3, as a free fatty acid, as an ethyl or methyl ester of DPAn-6 or DPAn-3.

In another aspect, the DPAn-6, or DPAn-3, or oxylipin derivative thereof is provided in the form of a microbial oil, an animal oil, or from a plant oil that has been derived from an oil seed plant that has been genetically modified to produce long chain polyunsaturated fatty acids. In another aspect, the oxylipin derivative is produced from an enzymatic conversion of DPAn-6 or DPAn-3 to its oxylipin derivative. In yet another aspect, the oxylipin derivative is chemically synthesized de novo.

In any of the above aspects of this method of the invention, the method can further include administering aspirin to the individual. In one aspect, the method further includes administering at least one agent selected from: a statin, a non-steroidal anti-inflammatory agent, an antioxidant, and a neuroprotective agent.

Another embodiment of the present invention relates to a method to produce a docosanoid, comprising chemically synthesizing any of the above-described docosanoids of the present invention.

Yet another embodiment of the present invention relates to a method to produce docosanoids, comprising catalytically producing docosanoids by contacting a DPAn-6 substrate, a DTAn-6 substrate, or a DPAn-3 substrate with an enzyme that catalyzes the production of the docosanoids from said DPAn-6 substrate, said DTAn-6 substrate or said DPAn-3 substrate.

Yet another embodiment of the present invention relates to a method to produce docosanoids, comprising culturing long chain polyunsaturated fatty acid (LCPUFA)-producing microorganisms or growing LCPUFA-producing plants that have been genetically modified to overexpress an enzyme that catalyzes the production of the docosanoids from a 22 carbon LCPUFA, to produce said docosanoids.

Another method of the present invention relates to a method to produce docosanoids, comprising contacting long chain polyunsaturated fatty acids (LCPUFAs) produced by LCPUFA-producing microorganisms, LCPUFA-producing plants, or LCPUFA-producing animals, with an enzyme that catalyzes the conversion of said LCPUFAs to docosanoids.

In one aspect of the above-described methods to produce docosanoids, the enzyme is selected from the group consisting of a lipoxygenase, a cyclooxygenase, and a cytochrome P450 enzyme. For example, such enzymes include, but are not limited to: 12-lipoxygenase, 5-lipoxygenase, 15-lipoxygenase, cyclooxygenase-2, hemoglobin alpha 1, hemoglobin beta, hemoglobin gamma A, CYP4A11, CYP4B1, CYP4F11, CYP4F12, CYP4F2, CYP4F3, CYP4F8, CYP4V2, CYP4X1, CYP41, CYP2J2, CYP2C8, thromboxane A synthase 1, prostaglandin 12 synthase, and prostacyclin synthase. In one aspect, the LCPUFA is selected from: DPAn-6, DTAn-6 and DPAn-3.

In one aspect of the above-described methods, the LCPUFA-producing microorganisms or LCPUFA-producing plants have been genetically modified to produce LCPUFAs.

In another aspect, the LCPUFA-producing microorganisms endogenously produce LCPUFAs (e.g., Thraustochytrids).

Yet another embodiment of the present invention relates to a method to enrich an oil for the presence of at least one oxylipin derived from an LCPUFA or stabilize said oxylipin in the oil. The method includes culturing an LCPUFA-producing microorganism with a compound that enhances the enzymatic activity of an enzyme that catalyzes the conversion of LCPUFAs to oxylipins. In one aspect, the compound stimulates expression of the enzyme. In another aspect, the compound enhances or initiates autooxidation of the LCPUFAs. In one preferred aspect, the compound is acetosalicylic acid.

Another embodiment of the present invention relates to a method to enrich an oil for the presence of at least one oxylipin derived from an LCPUFA or stabilize said oxylipin in the oil. The method includes rupturing microbes or plant oil seeds in the presence of an enzyme that catalyzes the conversion of LCPUFAs to oxylipins, wherein the microbes and plant oil seeds produce at least one LCPUFA.

In one aspect of the above-described methods, the enzyme is selected from the group consisting of a lipoxygenase, a cyclooxygenase, and a cytochrome P450 enzyme. In another aspect, the method further comprises recovering and purifying the oxylipins. In this aspect, the oxylipins can also be further processed and recovered as derivatives of the oxylipins or salts thereof.

Another embodiment of the present invention relates to a method to process an oil containing oxylipin derivatives of LCPUFAs, comprising the steps of: (a) recovering an oil containing oxylipin derivatives of LCPUFAs produced by a microbial, plant or animal source; and (b) refining the oil using a process that minimizes the removal of free fatty acids from the oil to produce an oil that retains oxylipin derivatives of LCPUFAs. In one aspect, the animal is an aquatic animal, including, but not limited to, a fish. In one aspect, the plant is an oil seed plant. In one aspect, the microbial source is a Thraustochytrid.

In the above-described method, in one aspect, the step of refining comprises extraction of the oil with an alcohol, an alcohol:water mixture, or organic solvent. In another aspect, the step of refining comprises extraction of the oil with a non-polar organic solvent. In yet another aspect, the step of refining comprises extraction of the oil with an alcohol or an alcohol:water mixture.

In the above-described method, the step of refining can further comprise chill filtering, bleaching, further chill filtering and deodorizing of the oil. In one aspect, the step of refining further comprises bleaching and deodorizing the oil, in the absence of chill filtering steps. In another aspect, the step of refining further comprises deodorizing the oil, in the absence of chill filtering or bleaching steps.

In the above-described method, the method can further include a step of adding an antioxidant to the oil.

In the above-described method, the step of refining can include preparing the oil as an emulsion.

In one aspect of the above-described method the oil is further processed by contact with an enzyme that catalyzes the conversion of LCPUFAs to oxylipins. Such an enzyme can include, but is not limited to, a lipoxygenase, a cyclooxygenase, and a cytochrome P450 enzyme. In one aspect, the enzyme is immobilized on a substrate.

The above-described method can further include a step of separating the LCPUFA oxylipin derivatives from LCPUFAs in the oil by a technique including, but not limited to chromatography. This step of separating can further include adding said separated LCPUFA oxylipins to an oil or composition.

Yet another embodiment of the present invention relates to a method to process an oil containing oxylipin derivatives of LCPUFAs, comprising the steps of: (a) recovering an oil containing oxylipin derivatives of LCPUFAs produced by a microbial, plant or animal source; (b) refining the oil; and (c) separating LCPUFA oxylipins from LCPUFAs in the oil. In one aspect, the method further comprises, prior to step (c), a step of converting LCPUFAs in the oil to LCPUFA oxylipins by a chemical or biological process. In one aspect, the method further comprises adding said separated LCPUFA oxylipins to a product.

Another embodiment of the present invention relates to a method to prevent or reduce at least one symptom of inflammation or neurodegeneration in an individual, comprising administering to a patient at risk of, diagnosed with, or suspected of having inflammation or neurodegeneration or a condition or disease related thereto, an agent selected from: DTAn-6 and an oxylipin derivative of DTAn-6, to reduce at least one symptom of inflammation or neurodegeneration in the individual. In one aspect, the agent is an R- or S-epimer of a docosanoid selected from the group consisting of: mono-hydroxy derivatives of DTAn-6, dihydroxy derivatives of DTAn-6, and tri-hydroxy derivatives of DTAn-6. In another aspect, the agent is an R- or S-epimer of any of the above-described docosanoids from DTAn-6, or an analog, derivative or salt thereof.

Another embodiment of the present invention relates to an organism comprising a PUFA PKS pathway, wherein the organism has been genetically transformed to express an enzyme that converts an LCPUFA to an oxylipin. In one aspect, the organism is selected from the group consisting of plants and microorganisms. In another aspect, the organism is an oil seed plant that has been genetically modified to express a PUFA PKS pathway to produce long chain polyunsaturated fatty acids. In yet another aspect, the organism is a microorganism, including, but not limited to, a microorganism comprising an endogenous PUFA PKS pathway. In one aspect, the enzyme is selected from the group consisting of a lipoxygenase, a cyclooxygenase, and a cytochrome P450 enzyme.

BRIEF DESCRIPTION OF THE FIGURES OF THE INVENTION

FIG. 1 is a graph showing the kinetics of 15-lipoxygenase reactions with DHA, DPAn-6 and DPAn-3.
FIG. 2A shows the structure of 15-lipoxygenase products of DHA.
FIG. 2B is a mass spectral analysis of 17-hydroxy DHA.
FIG. 2C is a mass spectral analysis of 10,17-dihydroxy DHA.
FIG. 2D is a mass spectral analysis of 7,17-dihydroxy DHA.
FIG. 3A shows the structure of 15-lipoxygenase products of DPAn-6.
FIG. 3B is a mass spectral analysis of 17-hydroxy DPAn-6.
FIG. 3C is a mass spectral analysis of 10,17-dihydroxy DPAn-6.
FIG. 3D is a mass spectral analysis of 7,17-dihydroxy DPAn-6.
FIG. 4A shows the structure of 15-lipoxygenase products of DPAn-3.
FIG. 4B is a mass spectral analysis of 17-hydroxy DPAn-3.
FIG. 4C is a mass spectral analysis of 10,17-dihydroxy DPAn-3.
FIG. 4D is a mass spectral analysis of 7,17-dihydroxy DPAn-3.
FIG. 5A shows the structure of 15-lipoxygenase products of DTAn-6.
FIG. 5B is a mass spectral analysis of 17-hydroxy DTAn-6.
FIG. 5C is a mass spectral analysis of 7,17-dihydroxy DTAn-6.
FIG. 6 shows the major oxylipin products of DPAn-6 after sequential treatment with 15-lipoxygenase followed by hemoglobin.
FIG. 7 shows the major 5-lipoxygenase products of DHA.
FIG. 8 shows the major 5-lipoxygenase products of DPAn-6.
FIG. 9 shows the major 15-lipoxygenase products of DPAn-3.
FIG. 10 shows the major 5-lipoxygenase products of DHA.
FIG. 11 shows the major 5-lipoxygenase products of DPAn-6.
FIG. 12 shows the major 5-lipoxygenase products of DPAn-3.
FIG. 13 shows structures of EPA-derived oxylipins.
FIGS. 14A and 14B show structures of DHA-derived oxylipins.
FIG. 15 shows structures of DPAn-6-derived oxylipins.
FIG. 16 shows structures of DPAn-3-derived oxylipins.
FIG. 17 shows structures of DTAn-6-derived oxylipins.
FIG. 18A is a mass spectral total ion chromatograph of mono- and dihydroxy derivatives of DHA and DPAn-6 in algal DHA+DPAn-6 oil.
FIG. 18B shows MS/MS spectra of mono-hydroxy DPAn-6 derivatives in algal DHA+DPAn-6 oil.
FIG. 18C shows MS/MS spectra of dihydroxy DPAn-6 derivatives in algal DHA+DPAn-6 oil.
FIG. 19 is a graph showing the effect of feeding LCPUFA oils on paw edema in rats.
FIG. 20A is a graph showing the total cell migration into air pouch exudates after administration of docosanoids derived from DHA and DPAn-6 in the mouse dorsal air pouch model of inflammation.
FIG. 20B is a graph showing IL-1β concentrations in air pouch exudates after administration of docosanoids derived from DHA and DPAn-6 in the mouse dorsal air pouch model of inflammation.
FIG. 20C is a graph showing macrophage chemotactic protein 1 (MCP-1) concentrations in air pouch exudates after administration of docosanoids derived from DHA and DPAn-6 in the mouse dorsal air pouch model of inflammation.
FIG. 21 is a graph showing the effect of docosanoids on TNFα-induced IL-1β production in human glial cells.
FIG. 22 is a graph showing the effect of docosanoids on TNFα secretion by human T lymphocytes.
FIG. 23 shows structures of additional, novel C22-PUFA-derived oxylipins.

DETAILED DESCRIPTION OF THE INVENTION

Recognizing the need in the art for novel anti-inflammatory compounds and for alternative ways of providing known anti-inflammatory compounds, such as the lipoxins, resolvins and docosatrienes described above, the present inventors have made several interrelated discoveries that have resulted in the provision of novel anti-inflammatory reagents and improved compositions for use in anti-inflammation applications.

First, the present invention relates to the discovery by the present inventors that the long chain omega-6 fatty acids, docosapentaenoic acid (DPAn-6; C22:5n-6) and docosatetraenoic acid (DTAn-6; C22:4n-6) (also called adrenic acid), as well as the omega-3 counterpart of DPAn-6, docosapentaenoic acid (DPAn-3; C22:5n-3), are substrates for the production of novel compounds referred to generally herein as LCPUFA oxylipins, and more particularly referred to as docosanoids (including mono-, di-, tri-, tetra-, and pentahydroxy derivatives of such docosanoids). The terms "oxylipin" and "docosanoid" as used herein are defined and described in detail below. The present inventors have discovered that DPAn-6, DPAn-3, DTAn-6 and the oxylipin derivatives thereof, can serve, like the long chain omega-3 fatty acids DHA and EPA and their oxylipin derivatives, as potent anti-inflammatory agents. Therefore, in one embodiment, the present invention provides novel oxylipins derived from the omega-6 fatty acids DPAn-6 and DTAn-6 and/or from the omega-3 fatty acid DPAn-3, and derivatives and analogs thereof, as well as methods for the production and use of such oxylipins as anti-inflammatory compounds and nutritional/health supplements. The present invention also provides the use of these LCPUFAs (DPAn-6, DTAn-6 and DPAn-3) themselves as novel anti-inflammatory compounds (e.g., as a precursor for the oxylipins or as an agent with intrinsic anti-inflammatory activity).

Initially, the present inventors recognized that the presence of DPAn-6 in a DHA oil substantially enhanced the reduction in inflammation in patients (e.g., enhanced a reduction in indicators or mediators of inflammation, such as pro-inflammatory cytokine production and eicosanoid production) as compared to a DHA oil that did not contain any other fatty acids. From this discovery, the inventors have now discovered that the unique structure of DPAn-6, DTAn-6, and DPAn-3 will allow these LCPUFAs to serve as a substrate in an enzymatic reaction similar to that which converts DHA to docosatrienes or resolvins, resulting in the surprising discovery that DPAn-6, DTAn-6, and DPAn-3, and oxylipin derivatives thereof are new, potent, anti-inflammatory agents.

Prior to the present invention, it was not known that the long chain omega-6 fatty acid, DPAn-6, could serve as a substrate for producing novel oxylipins with anti-inflammatory properties similar to or exceeding those of the previously described docosatrienes and resolvins derived from EPA and DHA. Evidence prior to this invention suggested that the presence of DPAn-6 in an oil would lead to the production of pro-inflammatory compounds and therefore decrease the overall anti-inflammatory effect of the DHA-containing oil. For example, DPAn-6 can readily retroconvert to arachidonic acid (ARA), which is generally considered to be pro-inflammatory since it is a precursor to a variety of highly potent pro-inflammatory eicosanoids, including leukotriene B4 and prostaglandin E2. Indeed, most of the eicosanoids derived from the omega-6 fatty acid ARA are pro-inflammatory (Gilroy et al, 2004; Meydani et all, 1990; Simopoulos 2002), and consumption of ARA reverses the anti-inflammatory effects of DHA (See Example 14 below). Therefore, prior to the present invention, it was generally believed that DPAn-6 would be pro-inflammatory since it would feed into the ARA metabolic pathway. Moreover, it was not recognized prior to the present invention that docosapentaenoic acid (DPAn-6; C22:5n-6), because of its unique structure, is an important substrate for the production of novel oxylipins, or that novel oxylipins could also be derived from docosapentaenoic acid (DPAn-3; C22:5n-3) and docosatetraenoic acid (DTAn-6; C22:4n-6). Indeed, the present inventors have found that DPAn-6 and DPAn-3 are superior substrates in oxylipin-generating reactions as compared to DHA and have found that DTAn-6 is also a substrate in oxylipin-generating reactions. This is demonstrated with regard to the conversion of each of DHA, DPAn-6 and DPAn-3 with 15-lipoxygenase in Example 1 below. Therefore, the production of docosanoids from DPAn-6 and DPAn-3 is more efficient and will result in greater oxylipin product levels than the production of docosanoids from DHA.

Additionally, it was not recognized that the oxylipins synthesized from DPAn-6 and DPAn-3 have unique properties, especially with regard to inflammation. In particular, and without being bound by theory, the present inventors believe that DPAn-6 and DPAn-3 and oxylipin derivatives thereof, and particularly DPAn-6 and oxylipin derivatives thereof, are equal to or even more potent anti-inflammatory compounds than DHA, EPA, or the oxylipin derivatives of those LCPUFAs. Without being bound by theory, the present inventors also expect that DTAn-6 and oxylipin derivatives thereof will have anti-inflammatory properties. Indeed, combinations of DPAn-6 and DPAn-3 and/or oxylipin derivatives thereof, and particularly DPAn-6 and/or oxylipin derivatives thereof, with DHA or EPA and/or oxylipin derivatives thereof (and particularly with DHA and/or oxylipin derivatives thereof) will provide a greater benefit in nutritional applications (e.g., any applications of the invention directed to the provision of nutrients and nutritional agents to maintain, stabilize, enhance, strengthen, or improve the health of an individual or the organic process by which an organism assimilates and uses food and liquids for functioning, growth and maintenance, and which includes nutraceutical applications), therapeutic applications (e.g., any applications of the invention directed to prevention, treatment, management, healing, alleviation and/or cure of a disease or condition that is a deviation from the health of an individual) and other applications (e.g., cosmetic) than that provided by DHA, EPA and/or oxylipin derivatives thereof alone.

More particularly, the present inventors have discovered that consumption of an oil containing DPAn-6 in addition to the omega-3 fatty acid, DHA, causes up to >90% reduction in inflammatory cytokine production, while consuming DHA alone in an oil facilitates reductions in inflammatory cytokine production of only about 13-29%, even when the DHA dose is approximately three times higher than in the DHA+DPAn-6 oil. Inflammatory eicosanoid secretion is also significantly reduced by DPAn-6 as compared to DHA alone. Therefore, the inventors discovered that an oil containing DPAn-6 and its oxylipin derivatives has significant anti-inflammatory properties. Furthermore, the inventors submit that the presence of DPAn-6 and a long chain omega-3 fatty acid (e.g., DHA), or the oxylipin derivatives thereof, jointly known as docosanoids, in combination results in the production of docosanoids (defined below) that have complementary anti-inflammatory activities. Therefore, formulations containing both a long chain omega-3 fatty acid such as DHA and DPAn-6 or oxylipins thereof are significantly more potent anti-inflammatory formulations than formulations containing omega-3 fatty acids alone. Furthermore, DPAn-6 and its oxylipin derivatives represent novel anti-inflammatory agents for use alone or in combination with a variety of other agents. DPAn-3 and its oxylipin derivatives and/or DTAn-6 and its oxylipin derivatives can also provide advantages over the use of DHA alone.

The present inventors were the first to recognize that DPAn-6 has anti-inflammatory properties and will enhance the anti-inflammatory effect of long chain omega-3 fatty acids, such as DHA. More particularly, the present inventors have recognized that the most distal n-3 bond between carbons 19 and 20 in DHA is not involved in the formation of the biologically important docosatrienes or 17S-resolvins, and therefore, the absence of this double bond in DPAn-6 would not hinder this fatty acid from being metabolically converted to analogous oxylipins by biological enzymes, such as the lipoxygenases. The inventors further recognized the double bonds involved in the majority of enzymatic conversions of DHA to oxylipins, particularly those compounds known as resolvins (i.e., those double bonds between carbons 7 and 8, carbons 10 and 11, carbons 13 and 14, and carbons 16 and 17 in DHA), were also present in DPAn-6, DTAn-6 and DPAn-3, facilitating their use as a substrate for the production of oxylipins. Without being bound by theory, this is believed to account for the differences in the data that were observed by the present inventors in studies using oil containing DHA and DPAn-6 as compared to DHA alone. The inventors have now demonstrated that the same enzymes that convert DHA to docosanoids or the 17S-resolvins recognize any (n-3) or (n-6) C-22 PUFA. Therefore, like DHA, DPAn-6, DTAn-6 and DPAn-3 are substrates for novel oxylipins that can serve as potent anti-inflammatory molecules. Additionally, these observations also suggest that LCPUFA of 24 or more carbons and that have double bonds located between carbons 7 and 8, carbons 10 and 11, carbons 13 and 14, and carbons 16 and 17, also serve as substrates for the production of novel oxylipins, and can be produced or enhanced in various oils and compositions using the methods outlined in the present application.

The inventors were, therefore, the first to recognize that the enzymes forming the oxylipins such as the previously described docosatrienes and resolvins derived from DHA did not discriminate between the (n-6) and (n-3) 22-carbon fatty acids as substrates because of the presence of the particular double bonds in the same location in these molecules. In fact, the inventors were the first to discover that the C22n-6 fatty acids are preferred substrates for these enzymes. The inventors were also the first to recognize that oxylipins from DPAn-6 have strong anti-inflammatory activity, and that a combination of oxylipins from both DHA and DPAn-6 has more anti-inflammatory benefits than those from DHA alone.

In another embodiment of the invention, the present inventors have also discovered novel ways of producing LCPUFA-rich oils that also contain enhanced and effective amounts of LCPUFA oxylipins (and in particular docosanoids), including the novel oxylipins of the present invention, as well as oxylipins that had been previously described. These LCPUFA-rich oils can be used in nutritional (including nutraceutical), cosmetic and/or pharmaceutical (including therapeutic) applications to deliver the immediate anti-inflammatory/neuroprotective action(s) of the hydroxy-LCPUFA derivatives along with the inherent long-term benefits of the LCPUFAs themselves.

The present inventors have also discovered that conventional sources of LCPUFAs, such as algal oils and fish oils, have only extremely small amounts of the hydroxyl-derivatives of LCPUFAs, and therefore, of the LCPUFA oxylipins, particularly docosanoids (e.g., from about 1 ng/g oil to about 10 µg/g oil). This is in part due to genetic and environmental factors associated with the production organisms (e.g., algae, fish), and is also due to the methods used to process LCPUFA oils from these organisms. Realizing that the provision of oils enriched in LCPUFA oxylipins would be of great benefit to human nutrition and health and would provide an alternative to the provision of chemically synthesized oxylipin analogs or to oils containing inadequate amounts of LCPUFA oxylipins, the present inventors have discovered alternative ways to produce these LCPUFA oils so that they are enriched in LCPUFA oxylipins (and in particular docosanoids), as well as alternative ways to process the LCPUFA oils to further enrich and enhance the LCPUFA oxylipin (and in particular docosanoid) content of the oils, thereby significantly enhancing their LCPUFA oxylipin (and in particular docosanoid) levels over those found in conventionally produced/processed LCPUFA oils.

In addition, the present inventors have discovered the oxylipins that are produced from DPAn-6, DTAn-6 and DPAn-3, and these oxylipins can now be chemically or biogenically produced and used as crude, semi-pure or pure compounds in a variety of compositions and formulations, or even added to oils, such as LCPUFA- or LCPUFA-oxylipin-containing oils, to enhance or supplement the natural oxylipins in such oils. Such compounds can also serve as lead compounds for the production of additional active analogs of these oxylipins in the design and production of nutritional agents and therapeutic drugs.

General Definitions

For the purposes of this application, long chain polyunsaturated fatty acids (LCPUFAs) are defined as fatty acids of 18 and more carbon chain length, and are preferably fatty acids of 20 or more carbon chain length, containing 3 or more double bonds. LCPUFAs of the omega-6 series include: di-homo-gammalinoleic acid (C20:3n-6), arachidonic acid (C20:4n-6), docosatetraenoic acid or adrenic acid (C22:4n-6), and docosapentaenoic acid (C22:5n-6). The LCPUFAs of the omega-3 series include: eicosatrienoic acid (C20:3n-3), eicosatetraenoic acid (C20:4n-3), eicosapentaenoic acid (C20:5n-3), docosapentaenoic acid (C22:5n-3), and docosahexaenoic acid (C22:6n-3). The LCPUFAs also include fatty acids with greater than 22 carbons and 4 or more double bonds including, but not limited to, C24:6(n-3) and C28:8(n-3).

The terms "polyunsaturated fatty acid" and "PUFA" include not only the free fatty acid form, but other forms as well, such as the triacylglycerol (TAG) form, the phospholipid (PL) form and other esterified forms.

As used herein, the term "lipid" includes phospholipids; free fatty acids; esters of fatty acids; triacylglycerols; diacylglycerides; monoacylglycerides; lysophospholipids; soaps; phosphatides; sterols and sterol esters; carotenoids; xanthophylls (e.g., oxycarotenoids); hydrocarbons; and other lipids known to one of ordinary skill in the art.

For the purposes of this application, "oxylipins" are defined as biologically active, oxygenated derivatives of polyunsaturated fatty acids, formed by oxidative metabolism of polyunsaturated fatty acids. Oxylipins that are formed via the lipoxygenase pathway are called lipoxins. Oxylipins that are formed via the cyclooxygenase pathway are called prostanoids. Oxylipins formed from 20 carbon fatty acids (arachidonic acid and eicosapentaenoic acid) are called eicosanoids. Eicosanoids include prostaglandins, leukotrienes and thromboxanes. They are formed either via the lipoxygenase pathway (leukotrienes) or via the cyclooxygenase pathway (prostaglandins, prostacyclin, thromboxanes). Oxylipins formed from 22 carbon fatty acids (docosapentaenoic acid (n-6 or n-3), docosahexaenoic acid and docosatetraenoic acid) are called docosanoids. Specific examples of these compounds are described below. General reference to an oxylipin described herein is intended to encompass the derivatives and analogs of a specified oxylipin compound.

As used herein, the term "analog" refers to a chemical compound that is structurally similar to another compound but differs slightly in composition (as in the replacement of one atom by an atom of a different element or in the presence of a particular functional group, or the replacement of one functional group by another functional group) (see detailed discussion of analogs of the present invention below).

As used herein, the term "derivative", when used to describe a compound of the present invention, means that at least one hydrogen bound to the unsubstituted compound is replaced with a different atom or a chemical moiety (see detailed discussion of derivatives of the present invention below).

In general, the term "biologically active" indicates that a compound has at least one detectable activity that has an effect on the metabolic or other processes of a cell or organism, as measured or observed in vivo (i.e., in a natural physiological environment) or in vitro (i.e., under laboratory conditions).

The oxygenated derivatives of long chain polyunsaturated fatty acids (LCPUFAs) include mono-, di-, tri-, tetra-, and penta-hydroxy derivatives of the LCPUFAs, and also include the free, esterified, peroxy and epoxy forms of these derivatives. These mono-, di-, tri-, tetra-, and penta-hydroxy derivatives of LCPUFAs are those derivatives that contain 3, 4 or more double bonds, generally at least two of which are conjugated, and one or more non-carboxy, hydroxyl groups. Preferably, these derivatives contain 4-6 double bonds and at least 1-3 non-carboxy, hydroxyl groups, and more preferably, 2 or more non-carboxy, hydroxyl groups.

Oxygenated derivatives of the omega-3 fatty acids EPA and DHA, catalyzed by lipoxygenase or cyclo-oxygenase enzymes, including acetylated forms of cyclooxygenase 2 (COX2), which are capable of down regulating or resolving inflammatory processes, are commonly referred to as "resolvins", which is a coined term (neologism) that is functional in nature. The "docosatrienes" are a subclass of oxylipins derived from DHA and contain three conjugated double bonds. "Protectin" is another coined functional term for hydroxy derivatives of the omega-3 fatty acid DHA that have a neuroprotective effect.

According to the present invention, the term "docosanoid" specifically refers to any oxygenated derivatives (oxylipins) of any 22-carbon LCPUFA (e.g., DHA, DPAn-6, DPAn-3, or DTAn-6). The structures of such derivatives are described in detail below. It is noted that while the present inventors recognize that the novel oxylipin derivatives (docosanoids) of the present invention that are derived from DPAn-6, DPAn-3 and DTAn-6 might also be considered to be "resolvins" or "protectins" based on similar functional attributes of such oxylipins, for the purposes of this invention, it is preferred that the novel oxylipins of the present invention be generally referenced using the term "docosanoid", which provides a clear structural definition of such compounds. The docosanoids from DPAn-6, DPAn-3 and DTAn-6 have never before been described, to the best of the present inventors' knowledge.

Oxylipins Useful in the Present Invention

One embodiment of the present invention relates to novel oxylipins derived from DPAn-6, DPAn-3, or DTAn-6, and any analogs or derivatives of such oxylipins, including any compositions or formulations or products containing such oxylipins or analogs or derivatives thereof, as well as oils or other compositions or formulations or products that have been enriched by any method for any LCPUFA oxylipin or analogs or derivatives thereof, and particularly for any oxylipin derived from DHA, EPA, DPAn-6, DPAn-3 or DTAn-6, and more particularly, for any docosanoid, and even more particularly, for any oxylipin derived from DPAn-6, DPAn-3 or DTAn-6. The present invention also relates to any oils or other compositions or formulations or products in which such oxylipins (any oxylipin derived from DHA, EPA, DPAn-6, DPAn-3 or DTAn-6, and more particularly, any docosanoid) are stabilized or retained in the oils or compositions to improve the quantity, quality or stability of the oxylipin in the oil or composition, and/or to improve the absorption, bioavailability, and/or efficacy of the oxylipins contained in oils or compositions.

As discussed above, a variety of DHA- and EPA-derived oxylipins having anti-inflammatory activity, anti-proliferative activity, antioxidant activity, neuroprotective or vasoregulatory activity (Ye et al, 2002) are known, which have been more commonly referred to as resolvins or protectins. Such oxylipins are referenced as being encompassed by the present invention, particularly in embodiments where such oxylipins are enriched in oils and compositions, preferably using the methods and processing steps of the present invention. In addition, the present invention provides novel oxylipins derived from DPAn-6, DPAn-3, and DTAn-6, including analogs or derivatives thereof, which can also be enriched in various oils and compositions, preferably using the methods and processes of the invention, or which can be produced and if desired, isolated or purified, by a variety of biological or chemical methods, including by de novo production, for use in any therapeutic, nutritional (including nutraceutical), cosmetic, or other application as described herein. Therefore, the present invention encompasses isolated, semi-purified and purified oxylipins as described herein, as well as sources of oxylipins including synthesized and natural sources (e.g., oils or plants and portions thereof), and includes any source that has been enriched for the presence of an oxylipin useful in the present invention by genetic, biological or chemical methods, or by processing steps as described herein.

In general, oxylipins can have either pro-inflammatory or anti-inflammatory properties. According to the present invention, pro-inflammatory properties are properties (characteristics, activities, functions) that enhance inflammation in a cell, tissue or organism, and anti-inflammatory properties are properties that inhibit such inflammation. Inflammation in cells, tissues and/or organisms can be identified by a variety of characteristics including, but not limited to, the production of "proinflammatory" cytokines (e.g., interleukin-1α (IL-1α), IL-1β, tumor necrosis factor-α (TNFα), IL-6, IL-8, IL-12, macrophage inflammatory protein-1α (MIP-1α), macrophage chemotactic protein-1 (MCP-1; also known as macrophage/monocyte chemotactic and activating factor or monocyte chemoattractant protein-1) and interferon-γ (IFN-γ)), eicosanoid production, histamine production, bradykinin production, prostaglandin production, leukotriene production, fever, edema or other swelling, and accumulation of cellular mediators (e.g., neutrophils, macrophages, lymphocytes, etc.) at the site of inflammation.

In one embodiment, oxylipins useful in the present invention are those having anti-inflammatory properties, such as those derived from DHA, EPA, DPAn-6, DPAn-3 and DTAn-6 (described in detail below). Other important bioactive properties of oxylipins include, but are not limited to, anti-proliferative activity, antioxidant activity, neuroprotective and/or vasoregulatory activity. These properties are also preferred properties of oxylipins useful in the present invention, and are preferably characteristic of oxylipins derived from DHA, EPA, DPAn-6, DTAn-6 and DPAn-3. In another embodiment, oxylipins of the present invention include any oxylipins derived from DPAn-6 or DPAn-3 or DTAn-6, regardless of the particular functional properties of the oxylipin. Preferred oxylipins derived from DPAn-6 or DPAn-3 or DTAn-6 include those that provide a nutritional and/or therapeutic benefit, and more preferably, have anti-inflammatory activity, anti-proliferative activity, antioxidant activity, and/or neuroprotective activity.

EPA-Derived Oxylipins

Oxylipins derived from EPA that are useful in the present invention include, but are not limited to: 15-epi-lipoxin A4 (5S,6R,15R-trihydroxy eicosatetraenoic acid) and its intermediate 15R-hydroxy eicosapentaenoic acid (15R-HEPE); Resolvin E1 (5,12,18-trihydroxy EPA) and its intermediates 5,6-epoxy,18R-hydroxy-EPE, and 5S-hydro(peroxy),18R-hydroxy-EPE, and 18R-hydroxy-EPE (18R-HEPE); and Resolvin E2 (5S,18R-dihydroxy-EPE or 5S,18R-diHEPE) and its intermediates. See FIG. 13 below for structures of these EPA derivatives. EPA-derived oxylipins are described in detail in Serhan (2005), which is incorporated herein by reference in its entirety.

DHA-Derived Oxylipins

Oxylipins derived from DHA that are useful in the present invention include, but are not limited to: Resolvin D1 (7,8, 17R-trihydroxy DHA) and Resolvin D2 (7,16,17R-trihydroxy DHA) along with their S-epimers and their intermediates including: 17S/R-hydroperoxy DHA, and 7S-hydroperoxy, 17S/R—OH-DHA, and 7(8)-epoxy-17S/R—OH-DHA; Resolvin D4 (4,5,17R-trihydroxy DHA) and Resolvin D3 (4,11,17R trihydroxy DHA) along with their S-epimers and their intermediates including 17S/R-hydroperoxy DHA, and 4S-hydroperoxy, 17S/R—OH DHA and 4(5)-epoxy-17S/R—OH DHA; and Neuroprotectin D1 (10, 17S-docosatriene, protectin D1) along with its R epimer and their intermediates including the dihydroxy product 16,17-epoxy-docosatriene (16,17-epoxy-DT) and the hydroperoxy product 17S-hydroperoxy DHA; Resolvin D5 (7S,17S-dihydroxy DHA) and Resolvin D6 and their hydroxyl containing intermediates; and epoxide derivatives 7,8 epoxy DPA, 10,11-expoxy DPA, 13,14-epoxy DPA, and 19,20-epoxy DPA and dihydroxy derivative 13,14-dihydroxy docosapentaenoic acid; other mono-hydroxy DHA derivatives, including the R and S epimers of 7-hydroxy DHA, 10-hydroxy DHA, 11-hydroxy DHA, 13-hydroxy DHA, 14-hydroxy DHA, 16-hydroxy DHA and 17-hydroxy DHA; and other dihydroxy DHA derivatives, including the R and S epimers of 10,20-dihydroxy DHA, 7,14-dihydroxy DHA and 8,14-dihydroxy DHA. See Examples 2, 7, and 10, and FIGS. 2A-2D, FIG. 7, FIG. 10 and FIGS. 14A and B below for descriptions and structures of these DHA derivatives. DHA-derived oxylipins are described in detail in Serhan (2005) and Ye et al (2002), which are incorporated herein by reference in its entirety.

DPAn-6-, DTAn-6- and DPAn-3-Derived Oxylipins and Other Novel Docosanoids from C22 Fatty Acids One embodiment of the present invention relates to novel oxylipins that are derived from DPAn-6, DTAn-6, or DPA-n-3. Another embodiment of the invention relates to novel docosanoids that can be derived from C22 PUFAs. Specifically, the present inventors describe herein novel docosanoids, the structures of which were designed de novo from C22 fatty acid structures. Oxylipins encompassed by the present invention include any oxylipins derived from DPAn-6, DTAn-6, or DPAn-3, or generally from C22 fatty acids, and more particularly described herein as docosanoids. Novel docosanoids include any oxygenated derivative of DPAn-6, DTAn-6, DPAn-3, or any other novel oxygenated derivatives of C22 fatty acids (e.g., see FIG. 23), including any derivatives or analogs thereof. In particular, docosanoids of the present invention include, but are not limited to, any R- or S-epimer of any monohydroxy, dihydroxy, or trihydroxy derivative of any of DPAn-6, DTAn-6 or DPAn-3 or an C22 fatty acids, and can include derivatizations at any carbon that forms a carbon-carbon double bond in the reference LCPUFA. Docosanoids of the present invention also include any product of an enzyme reaction that uses DPAn-6, DTAn-6, or DPAn-3 as a substrate and that is catalyzed by an oxylipin-generating enzyme including, but not limited to lipoxygenases, cyclooxygenases, cytochrome P450 enzymes and other heme-containing enzymes, such as those described in Table 1 (see below). Table 1 provides sufficient information to identify the listed known enzymes, including official names, official symbols, aliases, organisms, and/or sequence database accession numbers for the enzymes.

TABLE 1

Lipoxygenase (LOX), cyclooxygenase (COX), cytochrome P450 (CYP) enzymes and other heme-containing enzymes that can be used to process LCPUFA oils and fatty acids to produce their hydroxyl fatty acid derivatives by methods described herein.

| LIPOXYGENASE TYPE ENZYMES |
| --- |
| ALOX12 |
| Official Symbol: ALOX12 and Name: arachidonate 12-lipoxygenase [*Homo sapiens*]<br>Other Aliases: HGNC: 429, LOG12<br>Other Designations: 12(S)-lipoxygenase; platelet-type 12-lipoxygenase/arachidonate 12-lipoxygenase<br>Chromosome: 17; Location: 17p13.1GeneID: 239 |
| Alox5 |
| Official Symbol: Alox5 and Name: arachidonate 5-lipoxygenase [*Rattus norvegicus*]<br>Other Aliases: RGD: 2096, LOX5A<br>Other Designations: 5-Lipoxygenase; 5-lipoxygenase<br>Chromosome: 4; Location: 4q42GeneID: 25290 |
| ALOXE3 |
| Official Symbol: ALOXE3 and Name: arachidonate lipoxygenase 3 [*Homo sapiens*]<br>Other Aliases: HGNC: 13743<br>Other Designations: epidermal lipoxygenase; lipoxygenase-3<br>Chromosome: 17; Location: 17p13.1GeneID: 59344 |
| LOC425997 |
| similar to arachidonate lipoxygenase 3; epidermal lipoxygenase; lipoxygenase-3 [*Gallus gallus*]<br>Chromosome: UnGeneID: 425997 |
| LOC489486 |
| similar to Arachidonate 12-lipoxygenase, 12R type (Epidermis-type lipoxygenase 12) (12R-lipoxygenase) (12R-LOX) [*Canis familiaris*] |

TABLE 1-continued

Lipoxygenase (LOX), cyclooxygenase (COX), cytochrome P450 (CYP) enzymes and other heme-containing enzymes that can be used to process LCPUFA oils and fatty acids to produce their hydroxyl fatty acid derivatives by methods described herein.

Chromosome: 5GeneID: 489486
LOC584973 similar to Arachidonate 12-lipoxygenase, 12R type (Epidermis-type lipoxygenase 12) (12R-lipoxygenase) (12R-LOX) [*Strongylocentrotus purpuratus*]
Chromosome: UnGeneID: 584973
LOC583202 similar to Arachidonate 12-lipoxygenase, 12R type (Epidermis-type lipoxygenase 12) (12R-lipoxygenase) (12R-LOX) [*Strongylocentrotus purpuratus*]
Chromosome: UnGeneID: 583202
LOC579368 similar to Arachidonate 12-lipoxygenase, 12R type (Epidermis-type lipoxygenase 12) (12R-lipoxygenase) (12R-LOX) [*Strongylocentrotus purpuratus*]
Chromosome: UnGeneID: 579368
LOC504803 similar to Arachidonate 12-lipoxygenase, 12R type (Epidermis-type lipoxygenase 12) (12R-lipoxygenase) (12R-LOX) [*Bos taurus*]
Chromosome: UnGeneID: 504803
ALOX5

Official Symbol: ALOX5 and Name: arachidonate 5-lipoxygenase [*Homo sapiens*]Other Aliases: HGNC: 435, 5-LO, 5LPG, LOG5Other Designations: arachidonic acid 5-lipoxygenase; leukotriene A4 synthaseChromosome: 10; Location: 10q11.2GeneID: 240
OSJNBa0057G07.
15 lipoxygenase L-2; lipoxygenase [*Oryza sativa* (*japonica* cultivar-group)]GeneID: 3044798
Alox15b Official Symbol: Alox15b and Name: arachidonate 15-lipoxygenase, second type [*Mus musculus*]
Other Aliases: MGI: 1098228, 8-LOX, 8S-LOX, Alox8
Other Designations: 8S-lipoxygenase
Chromosome: 11; Location: 11 B4GeneID: 11688
ALOX5AP Official Symbol: ALOX5AP and Name: arachidonate 5-lipoxygenase-activating protein [*Homo sapiens*]
Other Aliases: HGNC: 436, FLAP
Other Designations: MK-886-binding protein; five-lipoxygenase activating protein
Chromosome: 13; Location: 13q12GeneID: 241
LOC489485 similar to Arachidonate 15-lipoxygenase, type II (15-LOX-2) (8S-lipoxygenase) (8S-LOX) [*Canis familiaris*]
Chromosome: 5GeneID: 489485
LOC557523 similar to Arachidonate 5-lipoxygenase (5-lipoxygenase) (5-LO) [*Danio rerio*]
Chromosome: 15GeneID: 557523
Alox5ap Official Symbol: Alox5ap and Name: arachidonate 5-lipoxygenase activating protein [*Mus musculus*]
Other Aliases: MGI: 107505, Flap
Other Designations: arachidonate 5 lipoxygenase activating protein
Chromosome: 5GeneID: 11690
LOC562561 similar to Arachidonate 5-lipoxygenase (5-lipoxygenase) (5-LO) [*Danio rerio*]
Chromosome: UnGeneID: 562561
LOC423769 similar to Arachidonate 5-lipoxygenase (5-lipoxygenase) (5-LO) [*Gallus gallus*]
Chromosome: 6GeneID: 423769
LOC573013 similar to Arachidonate 5-lipoxygenase (5-lipoxygenase) (5-LO) [*Danio rerio*]
Chromosome: UnGeneID: 573013
LOC584481

TABLE 1-continued

Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

similar to Arachidonate 5-lipoxygenase (5-lipoxygenase) (5-LO)
[*Strongylocentrotus purpuratus*]
Chromosome: UnGeneID: 584481
5LOX-potato AAD04258. Reports 5-lipoxygenase [S . . . [gi: 2789652]
15-LOX Soybean P08170. Reports Seed lipoxygenase . . . [gi: 126398]
12-LOX-porcine D10621. Reports Sus scrofa gene f . . . [gi: 60391233]

B) CYCLOOXYGENASE ENZYMES

COX2-human

AAN87129. Reports prostaglandin syn . . . [gi: 27151898]

C) HEMOGLOBIN CONTAINING ENZYMES

HBA1

Official Symbol: HBA1 and Name: hemoglobin, alpha 1 [*Homo sapiens*]
Other Aliases: HGNC: 4823, CD31
Other Designations: alpha 1 globin; alpha one globin; alpha-1 globin; alpha-1-globin; alpha-2 globin;
alpha-2-globin; hemoglobin alpha 1 globin chain; hemoglobin alpha 2; hemoglobin alpha-1 chain;
hemoglobin alpha-2
Chromosome: 16; Location: 16p13.3GeneID: 3039

HBB

Official Symbol: HBB and Name: hemoglobin, beta [*Homo sapiens*]
Other Aliases: HGNC: 4827, CD113t-C, HBD, hemoglobin
Other Designations: beta globin; beta globin chain; haemoglobin A beta chain; hemoglobin beta
chain; hemoglobin delta Etolia variant
Chromosome: 11; Location: 11p15.5GeneID: 3043

HBG1

Official Symbol: HBG1 and Name: hemoglobin, gamma A [*Homo sapiens*]
Other Aliases: HGNC: 4831, HBGA, HBGR, HSGGL1, PRO2979
Other Designations: A-gamma globin; gamma A hemoglobin; gamma globin; hemoglobin gamma-a
chain; hemoglobin, gamma, regulator of
Chromosome: 11; Location: 11p15.5GeneID: 3047

D) CYTOCHROME P450 TYPE ENZYMES (Gene, Organism, Gene Database: SwissProt, Gene database: EMBL/Genbank/DDBJ)
CYP4A11, *Homo sapiens*, CP4AB_HUMAN, L04751 D26481 S67580 S67581 AF525488 AY369778
X71480

CYP4A4, *Oryctolagus cuniculus*, CP4A4_RABIT, L04758 J02818
CYP4A5, *Oryctolagus cuniculus*, CP4A5_RABIT, M28655 X57209
CYP4A6, *Oryctolagus cuniculus*, CP4A6_RABIT, M28656 M29531
CYP4A7, *Oryctolagus cuniculus*, CP4A7_RABIT, M28657 M29530
CYP4B1, *Homo sapiens*, CP4B1_HUMAN, J02871 X16699 AF491285 AY064485 AY064486
CYP4B1, *Oryctolagus cuniculus*, CP4B1_RABIT, M29852 AF176914 AF332576
CYP4C1, *Blaberus discoidalis*, CP4C1_BLADI, M63798
CYP4C21, *Blattella germanica*, CP4CU_BLAGE, AF275641
CYP4E4, *Drosophila melanogaster*, C4AE1_DROME, AE003423 AL009194 AY058450 U34331
CYP4F11, *Homo sapiens*, CP4FB_HUMAN, AF236085 BC016853 AC005336
CYP4F12, *Homo sapiens*, CP4FC_HUMAN, AY008841 AB035130 AB035131 AY358977
CYP4F2, *Homo sapiens*, CP4F2_HUMAN, D26480 U02388 AB015306 AF467894 AC005336
BC067437 BC067439 BC067440 AF221943
CYP4F3 *Homo sapiens* CP4F3_HUMAN, D12620 D12621 AB002454 AB002461 AF054821
AY792513

CYP4F8 *Homo sapiens* CP4F8_HUMAN, AF133298
CYP4V2 *Homo sapiens* CP4V2_HUMAN, AY422002 AK122600 AK126473 BC060857
CYP4V2, *Pongo pygmaeus* CP4V2_PONPY, CR858234
CYP4X1, *Homo sapiens* CP4X1_HUMAN, AY358537 AK098065 BC028102
CYP4Z1, *Homo sapiens* CP4Z1_HUMAN, AY262056 AY358631
Cyp4a1, *Rattus norvegicus* CP4A1_RAT, M14972 X07259 M57718
Cyp4a2, *Rattus norvegicus* CP4A2_RAT, M57719 BC078684
Cyp4a3, *Rattus norvegicus* CP4A3_RAT, M33936
Cyp4a8, *Rattus norvegicus* CP4A8_RAT, M37828
Cyp4aa1, *Drosophila melanogaster*, C4AA1_DROME AE003808
Cyp4ac1, *Drosophila melanogaster*, C4AC1_DROME AE003609 AY051602

TABLE 1-continued

Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

Cyp4ac2, *Drosophila melanogaster*, C4AC2_DROME, AE003609
Cyp4ac3, *Drosophila melanogaster*, C4AC3_DROME, AE003609 AY061002
Cyp4ad1, *Drosophila melanogaster*, C4AD1_DROME, AE003837 AY061058
Cyp4b1, *Mus musculus*, CP4B1_MOUSE, D50834 BC008996
Cyp4b1 *Rattus norvegicus* CP4B1_RAT, M29853 BC074012
Cyp4c3, *Drosophila melanogaster*, CP4C3_DROME, AE003775 BT010108 U34323
Cyp4d1, *Drosophila melanogaster*, CP4D1_DROME, X67645 AF016992 AF016993 AF016994
AF016995 AF016996 AF016997 AF016998 AF016999 AF017000 AF017001 AF017002 AF017003
AF017004 AE003423 AE003423 Z98269
Cyp4d1, *Drosophila simulans*, CP4D1_DROSI, AF017005
Cyp4d10, *Drosophila mettleri*, C4D10_DROMT, U91634
Cyp4d14, *Drosophila melanogaster*, C4D14_DROME, AE003423 AL009194
Cyp4d2, *Drosophila melanogaster*, CP4D2_DROME, X75955 Z23005 AE003423 AL009194
AY118763 AF017006 AF017007 AF017008 AF017009 AF017010 AF017011 AF017012 AF017013
AF017014 AF017015 AF017016 AF017017 AF017018-Cyp4d20, *Drosophila melanogaster*,
C4D20_DROME, AE003475
Cyp4d21, *Drosophila melanogaster*, C4D21_DROME, AE003618
Cyp4d8, *Drosophila melanogaster*, CP4D8_DROME, AE003558 AY058442 U34329
Cyp4e1, *Drosophila melanogaster*, CP4E1_DROME, AE003837 AY118793
Cyp4e2, *Drosophila melanogaster*, CP4E2_DROME, U56957 AE003837 AY058518 X86076 U34332
Cyp4e3, *Drosophila melanogaster*, CP4E3_DROME, AE003626 U34330
Cyp4e5, *Drosophila mettleri*, CP4E5_DROMT, U78486
Cyp4f1, *Rattus norvegicus*, CP4F1_RAT, M94548 AF200361
Cyp4f14, *Mus musculus*, CP4FE_MOUSE, AB037541 AB037540 AF233644 AK005007 AK018676
BC011228

Cyp4f4, *Rattus norvegicus*, CP4F4_RAT, U39206
Cyp4f5, *Rattus norvegicus*, CP4F5_RAT, U39207
Cyp4f6, *Rattus norvegicus*, CP4F6_RAT, U39208
Cyp4g1, *Drosophila melanogaster*, CP4G1_DROME, AE003417 AL009188 U34328
Cyp4g15, *Drosophila melanogaster*, C4G15_DROME, AF159624 AE003486 AY060719
Cyp4p1, *Drosophila melanogaster*, CP4P1_DROME, AE003834 AY071584 U34327
Cyp4p2, *Drosophila melanogaster*, CP4P2_DROME, AE003834 AY051564
Cyp4p3, *Drosophila melanogaster*, CP4P3_DROME, AE003834 AY075201
Cyp4s3, *Drosophila melanogaster*, CP4S3_DROME AE003498
Cyp4v3, *Mus musculus*, CP4V3_MOUSE, AB056457 AK004724
Cyp4x1, *Rattus norvegicus*, CP4X1_RAT, AF439343

CYP2 Family of Cytochrome P450 Enzymes (sequences from Genbank)

CYP2J2 sequences from GenBank
NM_000775

*Homo sapiens* cytochrome P450, family 2, subfamily J, polypeptide 2 (CYP2J)
gi|18491007|ref|NM_000775.2|[18491007]
NM_000770

*Homo sapiens* cytochrome P450, family 2, subfamily C, polypeptide 8 (CYP2C8), transcript variant
Hp1-1, mRNA
gi|13787188|ref|NM_000770.2|[13787188]
NM_030878

*Homo sapiens* cytochrome P450, family 2, subfamily C, polypeptide 8 (CYP2C8), transcript variant
Hp1-2, mRNA gi|13787186|ref|NM_030878.1|[13787186]
NM_023025
*Rattus norvegicus* cytochrome P450, family 2, subfamily J, polypeptide 4 (Cyp2j4), mRNA
gi|61889087|ref|NM_023025.2|[61889087]
DN992115

TC119679 Human adult whole brain, large insert, pCMV expression library *Homo sapiens* cDNA
clone TC119679 5' similar to *Homo sapiens* cytochrome P450, family 2, subfamily J, polypeptide 2
(CYP2J2), mRNA sequence
gi|66251946|gb|DN992115.1|[66251946]
Z84061

SSZ84061 Porcine small intestine cDNA library Sus scrofa cDNA clone c13d09 5'
similar to cytochrome P450 monooxygenase CYP2J2, mRNA sequence
gi|1806390|emb|Z84061.1|[1806390]
BC091149

*Rattus norvegicus* cytochrome P450, family 2, subfamily J, polypeptide 4, mRNA (cDNA clone
MGC: 108684 IMAGE: 7323516), complete cds TABLE 1-continued Lipoxygenase (LOX), cyclooxygenase (COX), cytochrome P450 (CYP)
enzymes and other heme-containing enzymes that can be used to process LCPUFA
oils and fatty acids to produce their hydroxyl fatty acid derivatives by methods
described herein.

gi|60688166|gb|BC091149.1|[60688166]
NW_380169

*Bos taurus* chromosome Un genomic contig, whole genome shotgun sequence
gi|61630302|ref|NW_380169.1|BtUn_WGA215002_1[61630302]
BC032594

*Homo sapiens* cytochrome P450, family 2, subfamily J, polypeptide 2, mRNA (cDNA clone
MGC: 44831 IMAGE: 5527808), complete cds
gi|21595666|gb|BC032594.1|[21595666]
NT_086582

*Homo sapiens* chromosome 1 genomic contig, alternate assembly
gi|51460368|ref|NT_086582.1|Hs1_86277[51460368]
NT_032977

*Homo sapiens* chromosome 1 genomic contig
gi|51458674|ref|NT_032977.7|Hs1_33153[51458674]
CO581852

ILLUMIGEN_MCQ_46633 Katze_MMJJ Macaca mulatta cDNA clone IBIUW: 17960 5' similar to
Bases 384 to 953 highly similar to human CYP2J2 (Hs.152096), mRNA sequence
gi|50413382|gb|CO581852.1|[50413382]
AY410198

Mus musculus CYP2J2 gene, VIRTUAL TRANSCRIPT, partial sequence, genomic survey sequence
gi|39766166|gb|AY410198.1|[39766166]
AY410197

Pan troglodytes CYP2J2 gene, VIRTUAL TRANSCRIPT, partial sequence, genomic survey
sequence
gi|39766165|gb|AY410197.1|[39766165]
AY410196

*Homo sapiens* CYP2J2 gene, VIRTUAL TRANSCRIPT, partial sequence, genomic survey sequence
gi|39766164|gb|AY410196.1|[39766164]
AY426985

*Homo sapiens* cytochrome P450, family 2, subfamily J, polypeptide 2 (CYP2J2) gene, complete cds
gi|37574503|gb|AY426985.1|[37574503]
AB080265

*Homo sapiens* CYP2J2 mRNA for cytochrome P450 2J2, complete cds
gi|18874076|dbj|AB080265.1|[18874076]
AF272142

*Homo sapiens* cytochrome P450 (CYP2J2) gene, complete cds
gi|21262185|gb|AF272142.1|[21262185]
U37143

*Homo sapiens* cytochrome P450 monooxygenase CYP2J2 mRNA, complete cds
gi|18254512|gb|U37143.2|HSU37143[18254512]
AF039089

*Homo sapiens* cytochrome P450 (CYP2J2) gene, partial cds
gi|14486567|gb|AF039089.1|AF039089[14486567]
CYP5 Family of Cytochrome P450 Enzymes (sequences from Genbank)

NM_011539

*Mus musculus* thromboxane A synthase 1, platelet (Tbxas1), mRNA
gi|31981465|ref|NM_011539.2|[31981465]
NM_030984

*Homo sapiens* thromboxane A synthase 1 (platelet, cytochrome P450, family 5, subfamily A)
(TBXAS1), transcript variant TXS-II, mRNA
gi|13699839|ref|NM_030984.1|[13699839]
NM_001061

*Homo sapiens* thromboxane A synthase 1 (platelet, cytochrome P450, family 5, subfamily A)
(TBXAS1), transcript variant TXS-I, mRNA
gi|13699838|ref|NM_001061.2|[13699838]
BC041157

TABLE 1-continued

Lipoxygenase (LOX), cyclooxygenase (COX), cytochrome P450 (CYP) enzymes and other heme-containing enzymes that can be used to process LCPUFA oils and fatty acids to produce their hydroxyl fatty acid derivatives by methods described herein.

*Homo sapiens* thromboxane A synthase 1 (platelet, cytochrome P450, family 5, subfamily A), transcript variant TXS-I, mRNA (cDNA clone MGC: 48726 IMAGE: 5755195), complete cds
gi|27371225|gb|BC041157.1|[27371225]

CYP8 Family of Cytochrome P450 Enzymes (sequences from Genbank)

NM_000961

*Homo sapiens* prostaglandin I2 (prostacyclin) synthase (PTGIS), mRNA
gi|61676177|ref|NM_000961.3|[61676177]
NM_008968

*Mus musculus* prostaglandin I2 (prostacyclin) synthase (Ptgis), mRNA
gi|31982083|ref|NM_008968.2|[31982083]
D83402

*Homo sapiens* PTGIS(CYP8) gene for prostacyclin synthase, complete cds
gi|60683846|dbj|D83402.2|[60683846]
BC062151

*Mus musculus* prostaglandin I2 (prostacyclin) synthase, mRNA (cDNA clone MGC: 70035 IMAGE: 6512164), complete cds
gi|38328177|gb|BC062151.1|[38328177]

a) DPAn-6-Derived Oxylipins

DPAn-6-derived oxylipins (also referred to as oxylipins, or more particularly, docosanoids, from DPAn-6) include but are not limited to, any R- or S-epimer of any monohydroxy, dihydroxy, trihydroxy, or multi-hydroxy derivative of DPAn-6, and can include hydroxy derivatizations at any carbon that forms a carbon-carbon double bond in DPAn-6. Some exemplary, novel DPAn-6 derived oxylipins of the present invention include, but are not limited to: the R- and S-epimers of the monohydroxy products of DPAn-6, including 7-hydroxy DPAn-6,8-hydroxy DPAn-6,10-hydroxy DPAn-6,11-hydroxy DPAn-6,13-hydroxy DPAn-6,14-hydroxy DPAn-6, and 17-hydroxy DPAn-6 (most particularly 17-hydroxy DPAn-6); the R and S epimers of the dihydroxy derivatives of DPAn-6, including 7,17-dihydroxy DPAn-6, 10,17-dihydroxy DPAn-6, 13,17-dihydroxy DPAn-6, 7,14-dihydroxy DPAn-6, 8,14-dihydroxy DPAn-6, 16,17-dihdroxy DPAn-6, and 4,5-dihydroxy DPAn-6 (most particularly 10,17-dihydroxy DPAn-6); and tri-hydroxy derivatives of DPAn-6, including R and S epimers of 7,16,17-trihydroxy DPAn-6 and 4,5,17-trihydroxy DPAn-6. Structures of the DPAn-6 oxylipins are described and/or shown in Examples 3, 6, 8, and 11 and in FIGS. 3A-3D, FIG. 6, FIG. 8, FIG. 11 and FIG. 15.

The structures of various docosanoid products of enzymatic (15-lipoxygenase, 5-lipoxygenase, 12-lipoxygenase and hemoglobin) conversion of DPAn-6 are shown in Examples 3, 6, 8, and 11. These DPAn-6 derivatives are structurally analogous to those produced from DHA (Examples 2, 7 and 10) and DPAn-3 (Examples. 4, 9, and 12) when the same enzymes are used.

Examples 3-12 demonstrate the production of docosanoid products from DPAn-6, as well as DHA, DPAn-3 DTAn-6, and Example 13 describes the oxylipin (docosanoid) products found in a DHA/DPAn-6 LCPUFA oil.

b) DPAn-3-Derived Oxylipins

DPAn-3-derived oxylipins (also referred to as oxylipins, or more particularly, docosanoids, from DPAn-3) include but are not limited to, any R- or S-epimer of any monohydroxy, dihydroxy, trihydroxy, or multi-hydroxy derivative of DPAn-3, and can include hydroxy derivatizations at any carbon that forms a carbon-carbon double bond in DPAn-3. Some exemplary, novel DPAn-3 derived oxylipins of the present invention include, but are not limited to: the R- and S-epimers of the monohydroxy products of DPAn-3, including 7-hydroxy DPAn-3, 10-hydroxy DPAn-3, 11-hydroxy DPAn-3, 13-hydroxy DPAn-3, 14-hydroxy DPAn-3, 16-hydroxy DPAn-3, and 17-hydroxy DPAn-3; the R and S epimers of the dihydroxy derivatives of DPAn-3, including 7,17-dihydroxy DPAn-3, 10,17-dihydroxy DPAn-3, 8,14-dihydroxy DPAn-3, 16,17-dihydroxy DPAn-3, 13,20-dihydroxy DPAn-3, and 10,20-dihydroxy DPAn-3; and tri-hydroxy derivatives of DPAn-3, including R and S epimers of 7,16,17-trihydroxy DPAn-3. Structures of the DPAn-3 oxylipins are described and/or shown in Examples 4, 9, and 12 and in FIGS. 4A-4D, FIG. 9, FIG. 12 and FIG. 16.

c) DTAn-6-Derived Oxylipins

DTAn-6-derived oxylipins (also referred to as oxylipins, or more particularly, docosanoids, from DTAn-6) include but are not limited to, any R- or S-epimer of any monohydroxy, dihydroxy, trihydroxy, or multi-hydroxy derivative of DTAn-6, and can include hydroxy derivatizations at any carbon that forms a carbon-carbon double bond in DTAn-6. Some exemplary, novel DTAn-6 derived oxylipins of the present invention include, but are not limited to: the R- and S-epimers of the monohydroxy products of DTAn-6, including 7-hydroxy DTAn-6, 10-hydroxy DTAn-6, 13-hydroxy DTAn-6, and 17-hydroxy DTAn-6; the R and S epimers of the dihydroxy derivatives of DTAn-6, including 7,17-dihydroxy DTAn-6, 10,17-dihydroxy DTAn-6, and 16,17-dihydroxy DTAn-6; and tri-hydroxy derivatives of DTAn-6, including R and S epimers of 7,16,17-trihydroxy DTAn-6. Structures of the DTAn-6 oxylipins are described and/or shown in Example 5 and in FIGS. 5A-5C and FIG. 17.

d) Novel C22-PUFA-Derived Oxylipins

Other novel C22-PUFA-derived oxylipins (also referred to as oxylipins, or more particularly, docosanoids, from a C22-PUFA) include but are not limited to, any R- or S-epimer of any monohydroxy, dihydroxy, trihydroxy, or multi-hydroxy derivative of C22-PUFAs, and can include hydroxy derivatizations at any carbon that forms a carbon-carbon double bond in the C22-PUFAs. Some exemplary, novel docosanoids that are encompassed by the present invention include, but are not limited to 4,5-epoxy-17-hydroxy DPA, 7,8-epoxy DHA, 10,11-epoxy DHA, 13,14-epoxy DHA, 19,20-epoxy DHA, 13,14-dihydroxy DHA, 16,17-dihydroxy DTAn-6, 7,16,17-trihydroxy DTAn-6, 4,5,17-trihydroxy DTAn-6, 7,16,17-trihydroxy DTAn-3, 16,17-dihydroxy DTAn-3, 16,17-dihydroxy DTRAn-6, 7,16,17-trihydroxy DTRAn-6, 4,5-dihydroxy DTAn-6, and 10,16,17-trihydroxy DTRAn-6. Structures of these C22-PUFA-derived docosanoids are shown in FIG. 23.

DPAn-6-, DTAn-6- and DPAn-3-derived oxylipins, or other C22-PUFA-derived oxylipins of the present invention, as well as analogs or derivatives of any of such oxylipins of the present invention, can be produced by chemical synthesis or biological synthesis, including by de novo synthesis or enzymatic conversion of a substrate. Alternatively, such oxylipins can be produced by isolation, enrichment and/or conversion of substrates from natural sources (described below). According to the present invention, reference to an oxylipin "derived from" a specific LCPUFA, such as a "DPAn-6-derived oxylipin" or a "DPAn-6 oxylipin derivative", or a "DPAn-6 oxylipin analog" by way of example, refers to an oxylipin that has been produced by any method, using the knowledge of the structure of an oxylipin that can be produced using DPAn-6 as a substrate. Such an oxylipin need not be produced by an enzymatic reaction or biological system, but, as mentioned above, can alternatively be chemically synthesized de novo. In addition, analogs or derivatives of naturally occurring DPAn-6 oxylipins may be designed based on the structure of the naturally occurring DPAn-6 oxylipins, but which differ from the naturally occurring DPAn-6 oxylipin by at least one modification. Such analogs may also be synthesized de novo using chemical synthesis methods or using by modifications of biological production methods (e.g., enzyme reactions). Methods of producing oxylipins according to the present invention, including methods of enriching natural sources of such oxylipins, and by enzymatic conversion of substrates are described herein. Chemical synthesis methods for compounds such as oxylipins are also known in the art and can readily be applied to the novel oxylipin compounds of the present invention. Such methods are also described herein.

According to the present invention, the language "docosanoid-like compounds" or "docosanoid analogs" or "docosanoid derivatives" is intended to include analogs of any docosanoids described herein, including any of the novel docosanoids of the present invention that include a $C_{22}$ fatty acid having at least three olefinic groups (carbon-carbon double bonds). Similar language can also be used to more generally describe analogs and derivatives of any oxylipins as described herein (e.g., oxylipin-like compounds, oxylipin analogs, oxylipin derivatives).

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. For example, the reference compound can be a reference docosanoid such as any docosanoid derived from DHA, DPAn-6, DPAn-3 or DTAn-6, and an analog is a substance possessing a chemical structure or chemical properties similar to those of the reference docosanoid.

The terms "substituted", "substituted derivative" and "derivative", when used to describe a compound of the present invention, means that at least one hydrogen bound to the unsubstituted compound is replaced with a different atom or a chemical moiety. Examples of substituents include, but are not limited to, hydroxy, alkyl, halogen, nitro, cyano, heterocycle, aryl, heteroaryl, amino, amide, ester, ether, carboxylic acid, thiol, thioester, thioether, sulfoxide, sulfone, carbamate, peptidyl, $PO_3H_2$, and mixtures thereof.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorbtion properties.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-inflammatory activity, for example, using standard tests described herein, or using other similar tests which are well known in the art.

Prodrugs of any of the oxylipins described herein, and particularly, any of the docosanoids described herein, and even more particularly, any specific docosanoids as shown, for example, in any of FIGS. 2A-2D, 3A-3D, 4A-4D, 5A-5C, 6-17, 18A-18C and 23, may be identified using routine techniques known in the art. Various forms of prodrugs are known in the art. For examples of such prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8, 1-38 (1992); d) H. Bundgaard, et al., Journal of Pharmaceutical Sciences, 77:285 (1988); and e) N. Kakeya, et al., Chem. Pharm. Bull., 32: 692 (1984), each of which is specifically incorporated herein by reference.

In addition, the invention also includes solvates, metabolites, and salts (preferably pharmaceutically acceptable salts) of compounds of any of the oxylipins described herein, and particularly, any of the docosanoids described herein, and even more particularly, any specific docosanoids as shown, for example, in any of FIGS. 2A-2D, 3A-3D, 4A-4D, 5A-5C, 6-17, 18A-18C and 23.

The term "solvate" refers to an aggregate of a molecule with one or more solvent molecules. A "metabolite" is a pharmacologically active product produced through in vivo metabolism in the body or organism of a specified compound or salt thereof. Such products may result for example from the oxidation, reduction, hydrolysis, amidation, deamidation, esterification, deesterification, enzymatic cleavage, and the like, of the administered or produced compound. Accordingly, the invention includes metabolites of compounds of any of the oxylipins described herein, and particularly, any of the docosanoids described herein, and even more particularly, any specific docosanoids as shown, for example, in any of FIGS. 2A-2D, 3A-3D, 4A-4D, 5A-5C, 6-17, 18A-18C and 23, including compounds produced by a process comprising contacting a compound of this invention with an organism for a period of time sufficient to yield a metabolic product thereof.

A "pharmaceutically acceptable salt" or "salt" as used herein, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, gamma.-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfinuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

Oils, Compositions, Formulations or Products Containing DPAn-6, DPAn-3 DTAn-6, Other C22-LCPUFAs, Other LCPUFAs and/or Oxylipins Derived Therefrom The present invention includes oils, compositions, formulations and products comprising LCPUFAs and/or LCPUFA oxylipins described herein. According to the present invention, the term "product" can be used to generally or generically describe any oil, composition, or formulation of the present invention, although one term might be preferred over another depending on the context of use of the product. In one embodiment of the invention, oils, compositions, and formulations include at least DPAn-6, DTAn-6 or DPAn-3, or oxylipins derived therefrom, or any combinations thereof, and may additionally include any other LCPUFAs and/or any oxylipins derived therefrom. Such oxylipins can be produced by any chemical or biological (biogenic) method, including de novo synthesis, enzymatic conversion from any source (e.g., by enzymes including lipoxygenases, cyclooxygenases, cytochrome P450 enzymes and other heme-containing enzymes), purification from any source, and production from any biological source (e.g., microbial, plant, animal sources).

In one embodiment of the invention, oils are enriched for the presence of any LCPUFA-derived oxylipin (also known as an LCPUFA oxylipin), including any oxylipin derived from DHA, EPA, DPAn-6, DTAn-6, and/or DPAn-3, with LCPUFA-derived docosanoids being preferred, and oxylipins derived from DPAn-6, DTAn-6, or DPAn-3 being particularly preferred. In another embodiment, oils, compositions or formulations containing any LCPUFA-derived oxylipin are produced, processed or treated to retain, and/or improve the stability, absorption, bioactivity, bioavailability or efficacy of the LCPUFA oxylipins in the oil, compositions or formulations. Various methods of producing, processing and supplementing oils, compositions or formulations are described below.

Sources of LCPUFAs and LCPUFA-Derived Oxylipins for Use in the Present Invention Any source of LCPUFA can be used to produce the LCPUFAs, oxylipins, oils, compositions or formulations of the present invention, including, for example, animal (invertebrates and vertebrates), plant and microbial sources.

Examples of animal sources include aquatic animals (e.g., fish, marine mammals, and crustaceans such as krill and other euphausids) and lipids extracted from animal tissues (e.g. brain, liver, eyes, etc.).

More preferred sources include microorganisms and plants. Preferred microbial sources of LCPUFAs include algae, fungi (including yeast and filamentous fungi of the genus *Mortierella*), protists and bacteria. The use of a microorganism source, such as algae, can provide organoleptic advantages, i.e., fatty acids from a microorganism source may not have the fishy taste and smell that fatty acids from a fish source tend to have. However, fish oils are also included in the present invention. While fish oils may naturally undergo oxidation processes that produce aldehydes and ketones that impart bad odors and tastes to such fish oils, the present invention takes advantage of "directed" or "targeted" oxidation of specific compounds to produce docosanoids or mixtures of docosanoids that provide a beneficial quality to the oils containing such docosanoids, including fish oils. In a preferred embodiment, fish oils containing DHA and/or EPA, and DPAn-6, DTAn-6 and/or DPAn-3, are utilized in the invention.

Examples of bacterial sources include marine bacterial sources, such as members of the genus *Shewanella* and *Vibrio*.

Most preferably, the LCPUFA source comprises algae or protists. Preferred algal and protist genera are members of the kingdom Stramenopila, and more preferably, are members of the algal groups: dinoflagellates, diatoms, chrysophytes or thraustochytrids.

Preferably, dinoflagellates are members of the genus *Crypthecodinium* and even more preferably, members of the species *Crypthecodinium cohnii*.

Developments have resulted in frequent revision of the taxonomy of the Thraustochytrids (thraustochytrids). Taxonomic theorists generally place Thraustochytrids with the algae or algae-like protists. However, because of taxonomic uncertainty, it would be best for the purposes of the present invention to consider the strains described in the present invention as Thraustochytrids to include the following organisms: Order: Thraustochytriales; Family: Thraustochytriaceae (Genera: *Thraustochytrium* (which for this application, includes *Ulkenia*, although some consider it to be a separate genus), *Schizochytrium, Japonochytrium, Aplanochytrium*, or *Elina*) or Labyrinthulaceae (Genera: *Labyrinthula, Labyrinthuloides*, or *Labyrinthomyxa*). Also, the following genera are sometimes included in either family Thraustochytriaceae or Labyrinthulaceae: *Althornia, Corallochytrium, Diplophyrys*, and *Pyrrhosorus*), and for the purposes of this invention are encompassed by reference to a Thraustochytrid or a member of the order Thraustochytriales. It is recognized that at the time of this invention, revision in the taxonomy of Thraustochytrids places the genus *Labyrinthuloides* in the family of Labyrinthulaceae and confirms the placement of the two families Thraustochytriaceae and Labyrinthulaceae within the Stramenopile lineage. It is noted that the Labyrinthulaceae are sometimes commonly called labyrinthulids or *labyrinthula*, or *labyrinthuloides* and the Thraustochytriaceae are commonly called thraustochytrids, although, as discussed above, for the purposes of clarity of this invention, reference to Thraustochytrids encompasses any member of the order Thraustochytriales and/or includes members of both Thraustochytriaceae and Labyrinthulaceae. Information regarding such algae can be found, for example, in U.S. Pat. Nos. 5,407,957, 5,130,242 and 5,340,594, which are incorporated herein by reference in their entirety.

Particularly preferred LCPUFA and oxylipin sources for use in the present invention include microorganisms from a genus including, but not limited to: *Thraustochytrium, Japonochytrium, Aplanochytrium, Elina* and *Schizochytrium* within the Thraustochytriaceae, and *Labyrinthula, Labyrinthuloides*, and *Labyrinthomyxa* within the Labyrinthulaceae. Preferred species within these genera include, but are not limited to: any species within *Labyrinthula*, including *Labyrinthula* sp., *Labyrinthula algeriensis, Labyrinthula cienkowskii, Labyrinthula chattonii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula roscoffensis, Labyrinthula valkanovii, Labyrinthula vitellina, Labyrinthula vitellina pacifica, Labyrinthula vitellina vitellina, Labyrinthula zopfii*; any *Labyrinthuloides* species, including *Labyrinthuloides* sp., *Labyrinthuloides minuta, Labyrinthuloides schizochytrops*; any *Labyrinthomyxa* species, including *Labyrinthomyxa* sp., *Labyrinthomyxa pohlia, Labyrinthomyxa sauvageaui*, any *Aplanochytrium* species, including *Aplanochytrium* sp. and *Aplanochytrium kerguelensis*; any *Elina* species, including *Elina* sp., *Elina marisalba, Elina sinorifica*; any *Japonochytrium* species, including *Japonochytrium* sp., *Japonochytrium marinum*; any *Schizochytrium* species, including *Schizochytrium* sp., *Schizochytrium aggregatum, Schizochytrium limacinum, Schizochytrium minutum, Schizochytrium octosporum*; and any *Thraustochytrium* species, including *Thraustochytrium* sp., *Thraustochytrium aggregatum, Thraustochytrium arudimentale, Thraustochytrium aureum, Thraustochytrium benthicola, Thraustochytrium globosum, Thraustochytrium kinnei, Thraustochytrium motivum, Thraustochytrium pachydermum, Thraustochytrium proliferum, Thraustochytrium roseum, Thraustochytrium striatum, Ulkenia* sp., *Ulkenia minuta, Ulkenia profunda, Ulkenia radiate, Ulkenia sarkariana*, and *Ulkenia visurgensis*. Particularly preferred species within these genera include, but are not limited to: any *Schizochytrium* species, including *Schizochytrium aggregatum, Schizochytrium limacinum, Schizochytrium minutum*; or any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (Goldstein et Belsky) (ATCC 28209); *Schizochytrium limacinum* (Honda et Yokochi) (IFO 32693); *Thraustochytrium* sp. (23B) (ATCC 20892); *Thraustochytrium striatum* (Schneider) (ATCC 24473); *Thraustochytrium aureum* (Goldstein) (ATCC 34304); *Thraustochytrium roseum* (Goldstein) (ATCC 28210); *Japonochytrium* sp. (L1)(ATCC 28207); *Thraustochytrium* sp. 12B (ATCC 20890); *Thraustochytrium* sp. U42-2 (ATCC 20891); and *Labyrinthula* (labyrinthulid) strain L59 (Kumon) (IPOD AIST No. FERM P-19897).

In one aspect, the organism-sources of oils are genetically engineered to enhance the production of LCPUFAs and/or LCPUFA oxylipins. The more preferred sources are microorganisms (which can be grown in fermentors), or oilseed crops. For example, microorganisms and plants can be genetically engineered to express genes that produce LCPUFAs. Such genes can include genes encoding proteins involved in the classical fatty acid synthase pathways, or genes encoding proteins involved in the PUFA polyketide synthase (PKS) pathway. The genes and proteins involved in the classical fatty acid synthase pathways, and genetically modified organisms, such as plants, transformed with such genes, are described, for example, in Napier and Sayanova, *Proceedings of the Nutrition Society* (2005), 64:387-393; Robert et al., *Functional Plant Biology* (2005) 32:473-479; or U.S. Patent Application Publication 2004/0172682. The PUFA PKS pathway, genes and proteins included in this pathway, and genetically modified microorganisms and plants transformed with such genes for the expression and production of PUFAs are described in detail in: U.S. Pat. No. 6,566,583; U.S. Patent Application Publication No. 20020194641, U.S. Patent Application Publication No. 20040235127A1, and U.S. Patent Application Publication No. 20050100995A1, each of which is incorporated herein by reference in its entirety.

Preferred oilseed crops include soybeans, corn, safflower, sunflower, canola, flax, or rapeseed, linseed, and tobacco that have been genetically modified to produce LCPUFA as described above. More preferably, the oilseed crops also possess, or can be modified to possess (e.g., by genetic engineering), enzyme systems for converting the LCPUFA to its hydroxy derivative forms (i.e., oxylipin). Such enzymes are well known in the art and are described, for example, in Table 1.

Genetic transformation techniques for microorganisms and plants are well-known in the art. It is an embodiment of the present invention that the nucleic acid molecules encoding any one or more enzymes for converting an LCPUFA to its hydroxy-derivative form (and, if required, cofactors therefor) can be used to transform plants or microorganisms to initiate, improve and/or alter (modify, change) the oxylipin production capabilities of such plants or microorganisms. Transformation techniques for microorganisms are well known in the art and are discussed, for example, in Sambrook et al., 1989, *Molecular Cloning: A Laboratory Manual*, Cold Spring Harbor Labs Press. A general technique for transformation of dinoflagellates, which can be adapted for use with *Crypthecodinium cohnii*, is described in detail in Lohuis and Miller, *The Plant Journal* (1998) 13(3): 427-435. A general technique for genetic transformation of Thraustochytrids is described in detail U.S. Patent Application Publication No. 20030166207, published Sep. 4, 2003.

Methods for the genetic engineering of plants are also well known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119. See also, Horsch et al., *Science* 227:1229 (1985); Kado, C. I., *Crit. Rev. Plant. Sci.* 10:1 (1991); Moloney et al., *Plant Cell Reports* 8:238 (1989); U.S. Pat. No. 4,940,838; U.S. Pat. No. 5,464,763; Sanford et al., *Part. Sci. Technol.* 5:27 (1987); Sanford, J. C., *Trends Biotech.* 6:299 (1988); Sanford, J. C., *Physiol. Plant* 79:206 (1990); Klein et al., *Biotechnology* 10:268 (1992); Zhang et al., *Bio/Technology* 9:996 (1991); Deshayes et al., *EMBO J*, 4:2731 (1985); Christou et al., *Proc Natl. Acad. Sci. USA* 84:3962 (1987); Hain et al., *Mol. Gen. Genet.* 199:161 (1985); Draper et al., *Plant Cell Physiol.* 23:451 (1982); Donn et al., In Abstracts of VIIth International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

Preferably, microorganisms or oilseed plants useful as sources of LCPUFAs and oxylipins derived therefrom are microorganisms or plants that produce PUFAs (either naturally or by genetic engineering) having C20 or greater polyunsaturated fatty acids. Preferably, the LCPUFAs produced by the microorganism or plants have 3, 4 or more double bonds. Even more preferably, the microorganisms or plants produce C20 or greater LCPUFAs with 5 or more double bonds. Even more preferably, the microorganisms or plants produce C20 or greater LCPUFAs including, but not limited to: EPA (20:5n-3), DHA (C22:6n-3), DPAn-3(22:5n-3), DPAn-6(22:5n-6), DTAn-6 (22:4n-6) or combinations of these LCPUFAs.

In another embodiment, it is preferred that the microorganism or plant sources of LCPUFAs naturally express enzymes such as cyclooxygenases, lipoxygenases, cytochrome P450 enzymes (including hydroxylases, peroxidases, and oxygenases), and/or other heme-containing enzymes for biochemical conversion of LCPUFAs to oxylipins (e.g., to the hydroxy, peroxide, or epoxide derivatives of LCPUFAs). The invention also includes organisms (e.g., plants or microorganisms) that have been naturally selected or genetically engineered to express these enzymes and/or to have enhanced activity of these enzymes in the organism. Organisms can be genetically engineered to express or target any enzyme that catalyzes the biochemical conversion of LCPUFAs to oxylipins such as cyclooxygenases, lipoxygenases, cytochrome P450 enzymes (including hydroxylases, peroxidases, and oxygenases), and/or other heme-containing enzymes for biochemical conversion of LCPUFAs to oxylipins.

Numerous examples of such enzymes are known in the art and are listed in Table 1, although the invention is not limited to these particular enzymes. The enzymes in Table 1 are described by their name, official symbols, aliases, organisms, and/or by reference to the database accession number in the National Center for Biotechnology Information that contains the sequence information for the enzymes and genes encoding such enzymes. All of the information included in each of the database accession numbers is incorporated herein by reference. These enzymes and the genes encoding such enzymes, or homologues (including natural variants) thereof, can be used to genetically engineer an organism that produces LCPUFAs to express the enzyme or to target the an endogenous form of the enzyme to initiate, increase or enhance the activity of the enzyme in the organism. Optionally, these enzymes can be targeted to a particular compartment (e.g., plastids in plants), which is separated from compartments containing LCPUFAs, regulating the potential for formation and degradation of oxylipins produced in vivo. The enzymes (endogenous or recombinant) may be placed under the control of an inducible promoter, so that the production of oxylipins from LCPUFAs can be controlled in the organism. For example, in a plant, oxylipins can be formed during post-harvest processing in which the oilseeds are disrupted to allow contact of the LCPUFAs and oxygenase enzymes.

Microbial or plant cell sources of LCPUFAs useful in the present invention preferably include those microorganisms or plant cells that can be grown in a fermentor or photobioreactor. More preferably, microbial or plant cell sources of LCPUFAs useful in the present invention preferably include those microorganisms or plant cells that can be grown heterotrophically in fermentors.

Unique Characteristics of Oils Produced by the Present Invention

Oils containing oxylipins of LCPUFAs described herein have unique characteristics as compared to oxylipins that are chemically synthesized or produced by enzymatic conversion in vitro as described prior to the present invention. The LCPUFA oxylipins, and in particular, the docosanoids, are present in the oils in their free and/or esterifed forms. In the esterified form, the LCPUFA oxylipins, and in particular, the docosanoids, can be present in the triglyceride, diglyceride, monoglyceride, phospholipid, sterol ester and/or wax ester forms. Since the oxylipins have only been described previously in the free fatty acid form, the esterified forms represent novel forms of oxylipins, the presence of which can be enhanced, stabilized or retained in oils or compositions of the present invention. Without being bound by theory, the present inventors believe that once the LCPUFA oxylipins, and in particular, the docosanoids, are formed in the free fatty acid form, they can be re-esterified into one of the esterifed forms. Alternatively, the fatty acid molecules can be converted to oxylipins while they are still in an esterifed form.

The LCPUFA oil processed by the methods described according to the present invention (see below) will have total LCPUFA oxylipin concentrations, and in particular total docosanoid concentrations, that are at least 2×, at least 3×, at least 4×, at least 5×, at least 10×, at least 20×, at least 50×, at least 100×, at least 200×, at least 400×, at least 1,000×, or at least 5,000× higher (including any other increment of 1×, e.g., 20×, 21×, 22×, etc.) than the trace concentrations normally found in LCPUFA oils that have been through the standard refining, bleaching, and deodorization process commonly used for edible oils. LCPUFA oils produced by the processes outlined according to the present invention will preferably contain at least 1 µg, at least 5 µg, at least 10 µg, at least 15 µg, at least 20 µg, at least 30 µg, at least 50 µg, at least 100 µg, at least 200 µg, at least 500 µg, at least 1,000 µg, at least 2,000 µg, at least 5,000 µg, at least 10,000 µg, or at least 50,000 µg or more of at least one or more LCPUFA oxylipins, and in particular, docosanoids, per gram of oil (including any other increment in 0.1 µg increments). It is noted that through processing and purification of oils or compositions, the LCFUA oxylipin concentrations could actually be much higher (e.g., approaching 100%) during the production phase, although the oils and compositions would typically be diluted or titrated to the amounts described above prior to being used in a nutritional, therapeutic, or other process.

The oils produced from the present invention are enriched preferably with hydroxyl forms of DHA, and/or EPA and/or DPAn-3 and/or DPAn-6, and/or DTAn-6. LCPUFA hydroxy derivative-rich oils from this invention can be enriched with hydroxy forms of LCPUFA, including derivatives from just one LCPUFA (e.g. from DHA or EPA or DPAn-6 or DPAn-3 or DTAn-6), or from a combination of LCPUFAs (for example, DHA plus DPA (n-6 and/or n-3), DTAn-6, or EPA).

DPAn-6 or DPAn-3 or DTAn-6 Oils, Compositions and Formulations

One embodiment of the present invention includes the use of the LCPUFAs themselves, and particularly, DPAn-6 and/or DPAn-3, as anti-inflammatory or neuroprotective agents (i.e., the LCPUFAs are provided, alone or in combination with oxylipin metabolites thereof). DPAn-6 and/or DPAn-3 can be provided alone or in combination with other LCPUFAs, and preferably DHA and/or EPA. DTAn-6 having anti-inflammatory or neuroprotective properties is also encompassed by the present invention. Preferably, DPAn-6, DPAn-3 or DTAn-6 used in the present invention is provided in one of the following forms: as triglyceride containing DPAn-6, DTAn-6 and/or DPAn-3, as a phospholipid containing DPAn-6, DTAn-6 and/or DPAn-3, as a free fatty acid, as an ethyl or methyl ester of DPAn-6, DTAn-6 and/or DPAn-3.

In a preferred embodiment, the DPAn-6, DTAn-6 and/or DPAn-3 is provided in the form of an oil, and preferably a microbial oil (wild-type or genetically modified) or a plant oil from an oil seed plant that has been modified with genes that catalyze the production of LCPUFAs. Preferred microbial and oilseed sources have been described in detail above. Preferably, the DPAn-6, DTAn-6 or DPAn-3 to be used in the present invention, including oils or compositions containing such LCPUFAS and/or oxylipin-derivatives thereof, contains one or more of the following additional LCPUFAs or oxylipin-derivatives thereof: DHA or EPA. Most preferably, the additional LCPUFA is DHA.

DPAn-6 is the longest chain fatty acid in the omega-6 series. Docosapentaenoic acid (n-6) is found in numerous human foods and human breast milk at levels from 0.0 to 2.4% (Taber et al. 1998) and represents approximately 0.1% of total fatty acids (Koletzko et al. 1992), respectively. Major sources of DPAn-6 in the diet for adults and children are poultry (meat and eggs) and seafood (Taber et al. 1998, Nichols et al. 1998). DPAn-6 is typically a component of tissues in the human body, including the heart (Rocquelin et al. 1989), brain (Svennerholm et al. 1978, O'Brien et al. 1965), liver (Salem 1989), red blood cells (Sanders et al. 1978, Sanders et al. 1979) and adipose tissue (Clandinin et al. 1981).

Oils, compositions, or formulations (or any products) useful in the present invention preferably comprise DPAn-6, DPAn-3 and/or DTAn-6 in an amount that is at least about 2 weight percent, or at least about 5 weight percent, or at least about 10 weight percent, or at least about 15 weight percent, or at least about 20 weight percent, or at least about 25 weight percent, or at least about 30 weight percent, or at least about 35 weight percent, or at least about 40 weight percent, or at least about 45 weight percent, or at least about 50 weight percent, and so on, in increments of 1 weight percent (i.e., 2, 3, 4, 5, . . . ) up to or at least about 95 weight percent or higher of the total lipids in the oil, composition of formulation. DHA and/or EPA can also be included in an amount that is at least about 2 weight percent, or at least about 5 weight percent, or at least about 10 weight percent, or at least about 15 weight percent, or at least about 20 weight percent, or at least about 25 weight percent, or at least about 30 weight percent, or at least about 35 weight percent, or at least about 40 weight percent, or at least about 45 weight percent, or at least about 50 weight percent, and so on, in increments of 1 weight percent (i.e., 2, 3, 4, 5, . . . ) up to or at least about 95 weight percent or higher of the total lipids in the oil, composition, formulation or other product.

In another preferred embodiment, the oil, composition, formulation or other product comprises about 30 weight percent or more, about 35 weight percent or more, about 40 weight percent or more, about 45 weight percent or more, about 50 weight percent or more, about 55 weight percent or more, about 60 weight percent or more, about 65 weight percent or more, about 70 weight percent or more, about 75 weight percent or more, or about 80 weight percent or more, or about 85 weight percent or more, or about 90 weight percent or more, or about 95 weight percent or more of a combination of DPAn-6 and DHA. Preferably, the ratio of DHA to DPA (n-6) in the oil, composition, formulation or other product is between about 1:10 to about 10:1, or any ratio between 1:10 and 10:1.

Forms of Provision of LCPUFAs and Oxylipins

In accordance with the present invention, the LCPUFAs and/or oxylipin derivatives thereof that are used in oils, supplements, cosmetics, therapeutic compositions, and other formulations or products described herein are provided in a variety of forms. For example, such forms include, but are not limited to: an algal oil comprising the LCPUFAs and/or oxylipin derivatives thereof, preferably produced as described herein; a plant oil comprising the PUFA and/or oxylipin derivatives thereof, preferably produced as described herein; triglyceride oil comprising the PUFA; phospholipids comprising the PUFA; a combination of protein, triglyceride and/or phospholipid comprising the PUFA; dried marine microalgae comprising the PUFA; sphingolipids comprising the PUFA; esters of the PUFA; free fatty acid; a conjugate of the PUFA with another bioactive molecule; and combinations thereof. Long chain fatty acids can be provided in amounts and/or ratios that are different from the amounts or ratios that occur in the natural source of the fatty acids, such as by blending, purification, enrichment (e.g., through culture and/or processing techniques) and genetic engineering of the source. Bioactive molecules can include any suitable molecule, including, but not limited to, a protein, an amino acid (e.g. naturally occurring amino acids such as DHA-glycine, DHA-lysine, or amino acid analogs), a drug, and a carbohydrate. The forms outlined herein allow flexibility in the formulation of foods with high sensory quality, dietary or nutritional supplements, and pharmaceutical agents.

In one embodiment of the invention, a source of the desired phospholipids includes purified phospholipids from eggs, plant oils, and animal organs prepared via extraction by polar solvents (including alcohol or acetone) such as the Friolex process and phospholipid extraction process (PEP) (or related processes) for the preparation of oils or compositions (nutritional supplements, cosmetics, therapeutic formulations) rich in DPAn-6 and/or DPAn-6 or docosanoids derived therefrom, alone or in combination with DHA and/or EPA and/or oxylipins derived therefrom. The Friolex and related processes are described in greater detail in PCT Patent Nos. PCT/IB01/00841, entitled "Method for the Fractionation of Oil and Polar Lipid-Containing Native Raw Materials", filed Apr. 12, 2001, published as WO 01/76715 on Oct. 18, 2001; PCT/IB01/00963, entitled "Method for the Fractionation of Oil and Polar Lipid-Containing Native Raw Materials Using Alcohol and Centrifugation", filed Apr. 12, 2001, published as WO 01/76385 on Oct. 18, 2001; and PCT/DE95/01065 entitled "Process For Extracting Native Products Which Are Not Water-Soluble From Native Substance Mixtures By Centrifugal Force", filed Aug. 12, 1995, published as WO 96/05278 on Feb. 22, 1996; each of which is incorporated herein by reference in its entirety.

Any biologically acceptable dosage forms, and combinations thereof, are contemplated by the inventive subject matter. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, cereals, cereal coatings, foods, nutritive foods, functional foods and combinations thereof. The preparations of the above dosage forms are well known to persons of ordinary skill in the art. Preferably, a food (food product) that is enriched with the desired LCPUFAs and/or oxylipin derivatives thereof is selected from the group including, but not limited to: baked goods and mixes; chewing gum; breakfast cereals; cheese products; nuts and nut-based products; gelatins, pudding, and fillings; frozen dairy products; milk products; dairy product analogs; hard or soft candy; soups and soup mixes; snack foods; processed fruit juice; processed vegetable juice; fats and oils; fish products; plant protein products; poultry products; and meat products.

More particularly, oils containing LCPUFAs and oxylipin derivatives thereof, and particularly, enhanced levels of LCPUFA oxylipins (and in particular docosanoids), will be useful as dietary supplements in the form of oil-filled capsules or through fortification of foods, beverages or infant formula to enhance the anti-inflammatory benefits of these products and/or promote more balanced immune function over that achieved by an LCPUFA oil with low or no LCPUFA oxylipin (and in particular docosanoid) content. For example, LCPUFA oxylipin (and in particular docosanoid)-enriched LCPUFA oils capsules, and preferably gelatin capsules for protection against oxidation, are provided for delivery of both the LCPUFA(s) and enhanced LCPUFA oxylipin (and in particular docosanoid) content in a single dietary supplement. In another application, foods and beverages, including but not limited to dairy products and dairy analogs, bakery products and confectioneries, processed meats and meat analogs, grain products and cereals, liquid and powered beverages, including juices and juice drinks, carbonated and processed beverage products or infant formulas would be fortified with LCPUFA oils with enhanced levels of LCPUFA oxylipins (and in particular docosanoids) and thereby increase the LCPUFA oxylipin (and in particular docosanoid) intake over the non-LCPUFA oxylipin (and in particular docosanoid)-enriched LCPUFA oils alone. In another example, LCPUFA oxylipin (and in particular docosanoid)-enriched LCPUFA oils could be microencapsulated prior to fortification of the foods, beverages or formulas to reduce oxidation/degradation of the LCPUFA oxylipins (and in particular docosanoids) and/or LCPUFA and improve organoleptic properties and shelf-life of the fortified food/beverage or infant formula products. In another example, LCPUFA oxylipin (and in particular docosanoid)-enriched oils could be formulated into a cream or emulsion for topical applications for reduction of inflammation, or the LCPUFA oxylipin (and in particular docosanoid)-enriched oils could be formulated into sun screens or cosmetics, such as face or hand creams, moisturizers, foundations, eye gels or shaving creams, to reduce skin irritation or redness, allergic reactions, or puffiness/edema. In another example, more highly enriched or purified forms of the LCPUFA oxylipins (and in particular docosanoids) or LCPUFA oxylipin (and in particular docosanoid)-rich oils could be used in pharmaceutical formulations to prevent or reduce symptoms of conditions or diseases associated with local, systemic, chronic or acute inflammatory reactions or processes.

Additional Components

In one embodiment of the present invention, any of the sources of LCPUFAs and/or oxylipin derivatives thereof, including any oils or compositions or formulations containing such LCPUFAs or oxylipin derivatives thereof, can be provided with one or more additional components that may be useful in a method of the invention. Such additional components include, but are not limited to, any additional anti-inflammatory agent, nutritional supplement (e.g., vitamins, minerals and other nutritional agents, including nutraceutical agents), a therapeutic agent, or a pharmaceutical or a nutritional carrier (e.g., any excipient, diluent, delivery vehicle or carrier compounds and formulations that can be used in conjunction with pharmaceutical (including therapeutic) compositions or nutritional compositions).

In one preferred embodiment, the LCPUFAs and/or oxylipin derivatives thereof are provided along with acetosalicylic acid (ASA), or aspirin or any other anti-inflammatory agent.

Methods to Produce and Optimize Production of LCPUFAs and LCPUFA-Derived Oxylipins Methods for producing LCPUFA-containing oils (including DHA and DPAn-6) using microbial technology have been taught in the art. U.S. Pat. No. 5,130,242 and U.S. Pat. No. 5,340,594 teach methods for producing DHA and DPA rich lipids via fermentation using *Schizochytrium* spp. or *Thraustochytrium* spp. U.S. Patent Application Publication No. 2003/0161866 describes a process for preparing oils containing DHA and DPAn-6 by cultivating a microorganism belonging to the presumptive genus *Ulkenia*.

Methods for producing LCPUFA-containing plants and plant seed oils have been described in, for example, U.S. Pat. No. 6,566,583; U.S. Patent Application Publication No. 20020194641, U.S. Patent Application Publication No. 20040235127A1, and U.S. Patent Application Publication No. 20050100995A1, as well as Napier and Sayanova, *Proceedings of the Nutrition Society* (2005), 64:387-393; Robert et al., *Functional Plant Biology* (2005) 32:473-479; or U.S. Patent Application Publication 2004/0172682.

As discussed above, oxylipins useful in the present invention can be produced through chemical synthesis using LCPUFA precursors or can be synthesized completely de novo. Chemical synthesis methods for oxylipin compounds are known in the art (e.g., see Rodriguez and Spur (2004); Rodriguez and Spur, 2005; Guilford et al. (2004)). In addition, general chemical synthesis methods are well known in the art. For example, the compounds of present invention may be prepared by both conventional and solid phase synthetic techniques known to those skilled in the art. Useful conventional techniques include those disclosed by U.S. Pat. Nos. 5,569,769 and 5,242,940, and PCT publication No. WO 96/37476, all of which are incorporated herein in their entirety by this reference. Combinatorial synthetic techniques, however, may be particularly useful for the synthesis of the compounds of the present invention. See, e.g., Brown, *Contemporary Organic Synthesis*, 1997, 216; Felder and Poppinger, *Adv. Drug Res.*, 1997, 30, 111; Balkenhohl et al., *Angew. Chem. Int. Ed. Engl.*, 1996, 35, 2288; Hermkens et al., *Tetrahedron*, 1996, 52, 4527; Hermkens et al., *Tetrahedron*, 1997, 53, 5643; Thompson et al., *Chem. Rev.*, 1996, 96, 555; and Nefzi et al., *Chem. Rev.*, 1997, 2, 449-472.

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981, which is incorporated herein in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent upon the ring involved.

Alternatively, the oxylipins are catalytically produced via an enzyme-based technology using LCPUFAs as the substrate. In one embodiment, enzymes such as lipoxygenases, cyclooxygenases, cytochrome P450 enzymes and other heme-containing enzymes, such as those described in Table 1 (e.g., provided as recombinant or isolated/immobilized enzyme preparations) are contacted in vitro with the LCPUFAs produced by an organism, such as during extraction or post-harvest processing of a microorganism biomass or plant or oilseed or animal, whereby LCPUFAs produced by the organism are converted to oxylipins. The oxylipin derivatives of LCPUFAs can also be produced by microorganisms in a fermentor and recovered and purified for use. Preferred methods of production and recovery of oxylipins which are believed to enhance the quantity, quality and stability of the compounds are described below. The oxylipins produced by any of the above production technologies, can be further processed and recovered as derivatives of the oxylipins or salts thereof to aid in the recoverability, stability, absorption, bioavailability and/or efficacy, if desired. In addition, the oxylipins produced by any of the technologies described herein can be used to supplement other sources of oxylipins (e.g., a refined LCPUFA oil) or provided in the form of any composition or formulation for use in any application described herein.

Methods to Optimize Production of LCPUFA Oxylipin Concentrations in Oils Produced by Organisms The production or fermentation conditions can be optimized to enhance production of the LCPUFA oxylipins (and in particular docosanoids) and/or to stabilize them once they have been produced. These methods include selecting culture conditions that enhance activity and/or expression of the enzymes producing these compounds. For example, any culture condition that alters the cell concentration and/or specific growth rate of the culture can potentially alter the cellular composition. Culture conditions that are known to modify the production of metabolites or secondary metabolites in microorganisms include but are not limited to the following: hypoosmotic or hyperosomotic salinity stress, nutrient limitation stress (such as nitrogen, phosphorus, carbon, and/or trace metals), temperature stress (higher or lower than customary), elevated or reduced levels of oxygen and/or carbon dioxide, and physical stresses such as shear. In addition, the level of metabolites or secondary metabolites in cells can vary with phase of growth (exponential vs stationary), and by providing various precursor molecules for bioconversion by the microorganism.

These methods also include use of additives, both organic and inorganic, which enhance this enzymatic activity, or alternatively, directly enhance auto-oxidation of the LCPUFAs to these compounds and/or stabilize the LCPUFA oxylipins (and in particular docosanoids) once they are produced. For example, compounds that modify or acetylate COX2 (such as one of the many forms of acetylsalicylic acid) or compounds which stimulate expression or activity of COX2, lipoxygenase, cytochrome P450 enzymes (including hydroxylases, peroxidases, and oxygenases) and/or other heme-containing enzymes, can be added to the culture medium. Examples of compounds that may enhance the expression or activity of lipoxygenases, cyclooxygenases, cytochrome P450 and other heme-containing enzymes in culture include, but are not limited to: ATP, cytokines (e.g., interleukin-4, interleukin-13, or granulocyte-macrophage colony-stimulating factor), hormones (e.g., bradykinin or 1,25-dihydroxyvitamin $D_3$), cationic metals (e.g., $Ca^{2+}$), phospholipids (e.g., phosphatidyl serine), fatty acids (e.g., DHA), preformed hydroperoxides, glucocorticoids (e.g., dexamethasone), nonsteroidal anti-inflammatory compounds (e.g., acetosalicylic acid or aspirin), and other inducers of cytochrome P450 activities (e.g., ethanol, fibrates and other peroxisome proliferators, phenobarbital, steroids, and rifampicin). Additionally, compounds or conditions that lead to autooxidation of the LCPUFAs in the microorganism resulting in formation of the mono- thru penta-hydroxy derivatives of these LCPUFA are also preferred. For example, such compounds or conditions that can promote autooxidation of LCPUFAs include, but are not limited to, metals (including transition metals such as iron, copper or zinc, and alkali earth metals such as magnesium), peroxides, lipid radicals, and high oxygen conditions.

Improved Oil Extraction Processes that Enhance LCPUFA Oxylipin Content or Retention As enzymes play an important role in the formation of hydroxy derivatives of LCPUFAs, there are preferable methods for enhancing contact between these enzymes and the LCPUFAs to enhance formation of the hydroxy derivatives. In one preferred process, the microbial cells or oilseeds are ruptured (e.g., via homogenization for the microbial cells or by crushing for the oilseeds) and the resulting oil and biomass mixture is allowed to incubate for a period of time under optimal conditions (e.g., temperature, pH, residual water activity, ion concentration and presence of any necessary cofactors) to allow the enzymes liberated in the biomass to react directly with the LCPUFAs. Similarly, auto-oxidation processes can be facilitated in this manner.

Modification of Oil Processing Conditions

Preferred oil processing methods include methods that are focused on minimally processing the oil. Processes used in conventional oilseed processing tend to remove free fatty acids or free fatty acid-like compounds and thereby remove the fatty acid-like hydroxy derivatives of LCPUFAs. In particular, caustic treatments of the oils focused on removal of free fatty acids (commonly referred to as refining the oil), should be avoided. Preferably the oil is extracted with an alcohol (e.g. isopropyl alcohol) or other organic solvent (e.g. hexane), or mixtures thereof, or supercritical fluids (e.g. carbon dioxide) and the resulting oil is chill filtered, bleached, chill filtered again and then deodorized. In a more preferable method the chill filtration steps are eliminated and the oil is simply bleached and deodorized after extraction. In an even more preferable method, the only processing step after extraction of the oil is limited to deodorization of the oil. In the above extractions, alcohols or alcohol water mixtures are preferable for use in extracting the oil rather than using organic solvents such as hexane. As an alternative to chemical extraction, oils may be separated from the biomass through expeller pressing, or disruption followed by centrifugation, using a separating processing aid such as a primary alcohol or carrier oil. These crude oils may be purified and stabilized through one or more of the methods described above.

Methods for Further Processing LCPUFA oil (Microbial, Plant, Fish) to Enhance and/or Stabilize LCPUFA Oxylipin Content In one preferred method, once the oils have been extracted and processed by the methods described above or by any other suitable method, antioxidants can be added to the oil to help stabilize the LCPUFA oxylipins (and in particular docosanoids) in the oil. In another preferred method, antioxidants may be added at one or more points in the extraction and purification process to minimize potential oxidative degradation of oxylipins and/or LCPUFAs. In addition, the oxylipins will become more polar molecules as more hydroxy groups are incorporated into them, the oil can be prepared in an emulsion form to enhance content/solubility/stability of both polar and less polar forms of the LCPUFA oxylipins (and in particular docosanoids) and facilitate their use in, e.g., a wider variety of food and pharmaceutical applications than those available to use of an oil ingredient form alone.

In a preferable downstream process, an LCPUFA-rich oil (microbial-, plant- or animal (including fish)-based) or hydrolyzed or saponified form of the oil can be processed in an enzyme-based reaction system (e.g. column or stirred tank reactor) to facilitate the enzymatic production of the LCPUFA oxylipins (and in particular docosanoids) in the oil. The enzymes can be present in either free or immobilized forms in these systems. Exemplary enzymes (including lipoxygenases, cyclooxygenases, cytochrome P450 enzymes and other heme-containing enzymes) that can be utilized in these systems are listed in Table 1. Reaction conditions, such as temperature, pH, residual water activity, ion concentration and presence of cofactors, can be chosen to maximize the rate and extent of conversion of PUFAs to lipoxins. The oil can be processed through the column/reactor either in the oil form or as hydrolyzed free fatty acids, which are produced by hydrolyzing the PUFA-containing triglycerides in the oil to convert the PUFAs from an esterified to a free acid form.

In one embodiment of the invention, any of the oils produced by any of the methods described herein can be further processed to separate or purify the LCPUFA oxylipins from the LCPUFAs in the oil. This process can be performed on oils that have been processed by any refinement process, including oils or products thereof that have been treated to convert LCPUFAs in the oil to oxylipin derivatives. For example, LCPUFA oxylipins can be separated from LCPUFAs by any suitable technique, such as any chromatography technique, including, but not limited to, silica gel liquid chromatography. In one embodiment, LCPUFA oxylipins produced, enriched or purified by the processes of the present invention (including any of the production/processing methods described herein and/or de novo synthesis) can be added back to (titrated into) another oil, such as an LCPUFA oil produced by any method, and/or can be added to any composition or formulation or other product.

After the oils/fatty acids have been processed in this manner, the oil/fatty acids can be used directly in food, pharmaceutical or cosmetic applications or can be used to add (by blending) to LCPUFA or non-LCPUFA-containing oils to enhance their content of LCPUFA oxylipins (and in particular docosanoids). In this manner, a consistent LCPUFA oxylipin (and in particular docosanoid) content of the final oil product can be achieved.

When using lipoxygenase enzymes in these types of systems, up to 100% of the target LCPUFA can be transformed into their hydroxy derivatives. An example of such a system would be an immobilized enzyme column containing immobilized 15-lipoxygenase. When DPAn-6 is processed thru this system, the DPAn-6 is transformed to the hydroperoxides 17-hydroperoxyxy DPAn-6 and 10,17-di-hydroperoxy DPAn-6, which can then be transformed into the hydroxy derivatives 17-hydroxy DPAn-6 and 10,17-di-hyroxy DPAn-6, following reduction with an agent such as $NaBH_4$. This concentrated form of LCPUFA oxylipins (and in particular docosanoids) can then be titrated into an appropriate edible oil to achieve the desired LCPUFA oxylipin (and in particular docosanoid) content in the final oil.

Applications of DPAn-6, DPAn-3, and/or DTAn-6 LCPUFA Oxylipins and Oils or Compositions Comprising DPAn-6, DPAn-3, and/or DTAn-6 and/or any Other LCPUFA Oxylipins The present invention is based on the use of LCPUFAs comprising DPAn-6, DTAn-6, and/or DPAn-3 and/or the oxylipin derivatives thereof, and/or various oils that have been enriched for oxylipin derivatives of C20 and greater PUFAs, and particularly for docosanoids, to provide anti-inflammatory, anti-proliferative, neuroprotective and/or vasoregulatory effects in humans and other animals. Such effects are useful for enhancing the general health of an individual, as well as in treating or preventing a variety of diseases and conditions in an individual. For example, the invention includes methods for treating metabolic imbalances and disease states that could benefit from the modulation of inflammation provided by the LCPUFA and oxylipin, and particularly, docosanoid, containing compositions and oils described herein.

Additional applications encompassed by the present invention for the use of any of the LCPUFA and/or oxylipin-containing oils, compositions or formulations described herein (preferably including DPAn-6, DPAn-3 or oxylipin derivatives thereof, and as applicable DTAn-6 or oxylipin derivatives thereof, as well as oils and products produced with such oils that are enriched for oxylipin derivatives), include, but are not limited to, the following: (1) $Rh^+$ incompatibility during pregnancy; (2) inflammatory diseases of the bowel and gastrointestinal tract (e.g. Crohn's, inflammatory bowel disease, colitis, and necrotizing enterocolitis in infants); (3) autoimmune diseases (e.g. insulin-dependent diabetes mellitus (Type I diabetes), multiple sclerosis, rheumatoid arthritis, systemic lupus erythematosus, myasthenia gravis, celiac disease, autoimmune thyroiditis, Addison's disease, Graves' disease and rheumatic carditis); (4) chronic adult-onset diseases that involve inflammation (e.g. cardiovascular disease, Type II diabetes, age-related macular degeneration, atopic diseases, metabolic syndrome, Alzheimer's disease, cystic fibrosis, colon cancer, etc.); (5) inflammatory diseases of the skin (e.g., dermatitis (any form), eczema, psoriasis, rosacea, acne, pyoderma gangrenosum, urticaria, etc.); (6) inflammatory diseases of the eye; and (7) inflammation due to infectious diseases (bacteria, fungal, viral, parasitic, etc.). Many of these are diseases in which patients may not want to be on steroids or non-specific anti-inflammatory drugs because of negative side effects.

Accordingly, one embodiment of the present invention relates to the use of: (1) DPAn-6, DPAn-3 and/or an oxylipin derivative (docosanoid) thereof and, in some embodiments, DTAn-6 and/or an oxylipin derivative thereof, alone or in combination with each other and/or with other LCPUFAs and/or oxylipin derivatives thereof (preferably DHA or EPA, and most preferably, DHA); and/or (2) an oil or product produced using such oil, wherein the oil has been enriched in quantity, quality and/or stability of the LCPUFA oxylipins contained therein, and preferably the docosanoids. The use of these compositions is typically provided by an oil or product using such oil, a nutritional supplement, cosmetic formulation or pharmaceutical composition (medicament or medicine). Such oils, supplements, compositions and formulations can be used for the reduction of inflammation in a patient that has or is at risk of developing inflammation or a disease or condition associated with inflammation. Such oils, supplements, compositions and formulations can also be used for the reduction of any symptoms related to neurodegeneration or a disease associated with neurodegeneration in a patient that has or is at risk of developing a neurodegenerative condition or disease. In particular, the patient to be treated using the composition of the invention has inflammation associated with the production of eicosanoids and/or what are generally termed in the art as "proinflammatory" cytokines. Such cytokines include, but are not limited to, interleukin-1α (IL-1α), IL-1β, tumor necrosis factor-α (TNFα), IL-6, IL-8, IL-12, macrophage inflammatory protein-1α (MIP-1α), macrophage chemotactic protein-1 (MCP-1) and interferon-γ (IFN-γ). The patient is administered a composition comprising an amount of such LCPUFAs and/or oxylipin derivatives thereof in an amount effective to reduce at least one symptom of inflammation or neurodegeneration in the patient.

Symptoms of inflammation include both physiological and biological symptoms including, but are not limited to, cytokine production, eicosanoid production, histamine production, bradykinin production, prostaglandin production, leukotriene production, fever, edema or other swelling, pain (e.g., headaches, muscle aches, cramps, joint aches), chills, fatigue/loss of energy, loss of appetite, muscle or joint stiffness, redness of tissues, fluid retention, and accumulation of cellular mediators (e.g., neutrophils, macrophages, lymphocytes, etc.) at the site of inflammation. Diseases associated with inflammation include, but are not limited to, conditions associated with infection by infectious agents (e.g., bacteria, viruses), shock, ischemia, cardiopulmonary diseases, autoimmune diseases, neurodegenerative conditions, and allergic inflammatory conditions, and various other diseases detailed previously herein. The Examples describe the use of docosanoids of the present invention to reduce inflammation in vivo and in vitro, as measured by multiple parameters of an inflammatory response.

Symptoms associated with neurodegeneration include both physiological and biological symptoms including, but not limited to: neurodegeneration, intellectual decline, behavioral disorders, sleep disorders, common medical complications, dementia, psychosis, anxiety, depression, inflammation, pain, and dysphagia. Neurodegenerative diseases that may be treated using the oxylipin derivatives and compositions of the invention include, but are not limited to: schizophrenia, bipolar disorder, dyslexia, dyspraxia, attention deficit hyperactivity disorder (ADHD), epilepsy, autism, Alzheimer's Disease, Parkinson's Disease, senile dementia, peroxisomal proliferator activation disorder (PPAR), multiple sclerosis, diabetes-induced neuropathy, macular degeneration, retinopathy of prematurity, Huntington's Disease, amyotrophic lateral sclerosis (ALS), retinitis pigmentosa, cerebral palsy, muscular dystrophy, cancer, cystic fibrosis, neural tube defects, depression, Zellweger syndrome, Lissencepahly, Down's Syndrome, Muscle-Eye-Brain Disease, Walker-Warburg Syndrome, Charoct-Marie-Tooth Disease, inclusion body myositis (IBM) and Aniridia.

In one embodiment of the present invention, the novel docosanoids of the invention, and/or oils or compositions containing such docosanoids are used to selectively target the particular proinflammatory cytokines and conditions or diseases associated with the production of these cytokines. Based on the observation by the present inventors that particular docosanoids of the invention may selectively inhibit certain cytokines, the inventors propose that such docosanoids can be used in particular conditions or diseases to provide a more selective treatment of an individual and avoid side effects that may be associated with more global inhibition of inflammatory processes. For example, the present inventors have shown that the DPAn-6 docosanoids, 17-hydroxy DPAn-6 and 10,17-dihydroxy DPAn-6, significantly reduced secretion of the potent pro-inflammatory cytokine IL-1β, with the reduction produced by 10,17-dihydroxy DPAn-6 being significantly larger than with that produced by either the DHA oxylipin derivative or the general anti-inflammatory agent, indomethacin. Even more striking were the observed differences between the activities of two different oxylipin derivatives of DPAn-6. As shown in Examples 20 and 21, while both 17-HDPAn-6 and 10,17-dihydroxy DPAn-6 are demonstrated to be potent anti-inflammatory agents, there were differences between the activity of these two DPAn-6 oxylipins in their effect on cytokine production (e.g., IL-1β), indicating that one compound may be more suitable than the other for specific applications (e.g., sepsis versus swelling). Specifically, 17-HDPAn-6 was more potent than the DHA-derived oxylipin for inhibiting cell migration, and 10,17-dihydroxy DPAn-6 was more potent than the DHA oxylipin for reduction in IL-1β secretion. Therefore, one of skill in the art can select docosanoids of the present invention for specific uses, and reduce the potential side effects of a treatment as compared to using more pan-specific or generic anti-inflammatory agents.

The compositions and method of the present invention preferably protect the patient from inflammation, or a condition or disease associated with inflammation. As used herein, the phrase "protected from a disease" (or symptom or condition) refers to reducing the symptoms of the disease; reducing the occurrence of the disease, and/or reducing the severity of the disease. Protecting a patient can refer to the ability of a nutritional or therapeutic composition of the present invention, when administered to the patient, to prevent inflammation from occurring and/or to cure or to alleviate inflammation and/or disease/condition symptoms, signs or causes. As such, to protect a patient from a disease or condition includes both preventing occurrence of the disease or condition (prophylactic treatment) and treating a patient that has a disease or condition or that is experiencing initial symptoms of a disease or condition (therapeutic treatment). The term, "disease" or "condition" refers to any deviation from the normal health of an animal and includes a state when disease symptoms are present, as well as conditions in which a deviation (e.g., infection, gene mutation, genetic defect, etc.) has occurred, but symptoms are not yet manifested.

According to the present invention, the oxylipins (or analogs or derivatives thereof), compositions comprising such oxylipins, and methods of the invention, are suitable for use in any individual (subject) that is a member of the Vertebrate class, Mammalia, including, without limitation, primates, livestock and domestic pets (e.g., a companion animal). Most typically, an individual will be a human. According to the present invention, the terms "patient", "individual" and "subject" can be used interchangeably, and do not necessarily refer to an animal or person who is ill or sick (i.e., the terms can reference a healthy individual or an individual who is not experiencing any symptoms of a disease or condition). In one embodiment, an individual to which an oxylipin(s) or composition or formulation or oil of the present invention can be administered includes an individual who is at risk of, diagnosed with, or suspected of having inflammation or neurodegeneration or a condition or disease related thereto. Individuals can also be healthy individuals, wherein oxylipins or compositions of the invention are used to enhance, maintain or stabilize the health of the individual.

The amount of an LCPUFA or oxylipin derivative thereof to be administered to a individual can be any amount suitable to provide the desired result of reducing at least one symptom of inflammation or neurodegeneration or protecting the individual from a condition or disease associated with such inflammation or neurodegeneration. In one embodiment, an LCPUFA such as DPAn-6 is administered in a dosage of from about 0.5 mg of the PUFA per kg body weight of the individual to about 200 mg of the PUFA per kg body weight of the individual, although dosages are not limited to these amounts. An LCPUFA oxylipin derivative or mixture of oxylipin derivatives is administered in a dosage of from about 0.2 ug of the oxylipin per kg body weight of the individual to about 50 mg of the oxylipin per kg body weight of the individual, although dosages are not limited to these amounts.

Although compositions and formulations of the invention can be administered topically or as an injectable, the most preferred route of administration is oral administration. Preferably, the compositions and formulations used herein are administered to subjects in the form of nutritional supplements and/or foods (including food products) and/or pharmaceutical formulations and/or beverages, more preferably foods, beverages, and/or nutritional supplements, more preferably, foods and beverages, more preferably foods.

As discussed above, a variety of additional agents can be included in the compositions when administered or provided to the subject, such as other anti-inflammatory agents, vitamins, minerals, carriers, excipients, and other therapeutic agents. A preferred additional agent is aspirin, or another suitable anti-inflammatory agent.

The oxylipins (or analogs or derivatives or salts thereof), compositions comprising such oxylipins, and methods of the invention, are also suitable for use as feed ingredients, nutritional supplements or therapeutic agents in aquaculture applications in any individual (subject) that is a member of the Vertebrate class such as fish or for invertebrates such as shrimp.

The following experimental results are provided for purposes of illustration and are not intended to limit the scope of the invention.

EXAMPLES

Example 1

The following example demonstrates that DPAn-6 can be completely converted to a mono-hydroxy diene derivative by 15-lipoxygenase, and is more efficiently converted than either of DPAn-3 or DHA.

Soybean 15-lipoxygenase (Sigma-Aldrich, St. Louis, Mo.) at a final concentration of 4 µg/ml was mixed into 100 µM solutions of DHA, DPAn-6, or DPAn-3 (NuChek Prep, Elysian, Minn.) in 0.05M sodium borate buffer, pH 9.0, and the reaction mixtures were incubated at 0° C. Appearance of the mono-hydroxy conjugated diene derivatives of the fatty acids was monitored through absorbance at 238 nm. Conjugated diene products were quantified using an extinction coefficient of 28,000 $M^{-1}cm^{-1}$ (Shimizu et al; Methods in Enzymology, 1990 Vol 187, 296-306). As shown in Example. 1, 100% of the DPAn-6 was efficiently converted to its conjugated diene derivative under these conditions, whereas about 85% of DPAn-3 and 50% of DHA were converted to their respective conjugated diene (mono-hydroxy) derivative by the 15-lipoxygenase. No appreciable accumulation of the dihydroxy derivatives occurred under these reaction conditions.

Example 2

The following example describes the major 15-lipoxygenase products of DHA.

DHA (100 µM, NuChek Prep, Elysian, Minn.) was incubated with 15-LOX (4 µg/ml) in 0.05M sodium borate buffer, pH 9.0, at 4° C. with vigorous stirring for 30 min. Reaction products were reduced with $NaBH_4$ (0.45 mg/ml) and then extracted on a solid phase C-18 cartridge (Supelco Discovery DSC-19) using anhydrous ethanol for elution. Reaction products were analyzed by LC/MS/MS using an Agilent 1100 Series High Performance Liquid Chromatography (HPLC) Instrument (San Paulo, Calif. USA) interfaced with an Esquire 3000 ion trap mass spectrometer equipped with electrospray ionization source (Bruker Daltonics, Billerica Mass. USA). The HPLC was carried out on a LUNA C18(2) column (250×4.6 mm, 5 micron, Phenomenex, Torrance Calif., USA) using a mobile phase consisting of 100 mM ammonium acetate in 30% methanol in water with an acetonitrile gradient increasing from 48 to 90% over 50 min (0.4 ml/min flow rate). The mass spectrometer was operated in the negative ion detection mode. Nitrogen was used as nebulizing and drying gas with nebulizer pressure at 20 psi and drying gas flow rate of 7 L/min. The interface temperature was maintained at 330 C.

FIG. 2A depicts the structures of the mono- and dihydroxy products of this DHA reaction. FIG. 2B depicts MS/MS spectrum of the mono-hydroxy product showing the molecular ion (m/z of 343) and the characteristic fragments of 17-hydroxy DHA. Inset shows the UV spectrum of this compound with the expected peak at 237 nm, characteristic of a conjugated diene. FIGS. 2C and 2D depict MS/MS spectra of the two dihydroxy products with molecular ions (m/z of 359) and characteristic fragments of 10,17-hydroxy DHA (2C) and 7,17-dihydroxy DHA (2D) indicated. The UV spectrum insets show the expected triplet peaks at 270 nm characteristic of a conjugated triene for 10,17-dihydroxy DHA and a single peak at 242 characteristic of two pairs of conjugated dienes separated by a methylene group for 7,17-dihydroxy DHA.

Example 3

The following example indicates the major 15-lipoxygenase products of DPAn-6 and demonstrates production of mono- and dihydroxy derivatives analogous to those produced from DHA (see Example 2).

DPAn-6 was treated with 15-lipoxygenase and analyzed by LC/MS/MS under the conditions described in Example 2. FIG. 3A depicts the structures of the mono- and dihydroxy reaction products of this DPAn-6/15-LOX reaction. FIG. 3B depicts MS/MS spectrum of the mono-hydroxy product showing molecular ion (m/z of 345) and fragments characteristic of 17-hydroxy DPAn-6. The inset shows the UV spectrum of this compound with the expected peak at 237 nm characteristic of a conjugated diene. FIGS. 3C and 3D depict MS/MS spectra of the two dihydroxy products with molecular ions (m/z of 361) and fragments characteristic of 10,17-hydroxy DPAn-6 (3C) and 7,17-dihydroxy DPAn-6 (3D) indicated. The UV spectrum insets show the expected triplet peaks at 270 nm characteristic of a conjugated triene for 10,17-dihydroxy DPAn-6 and a single peak at 242 characteristic of two pairs of conjugated dienes separated by a methylene group for 7,17-dihydroxy DPAn-6.

Example 4

The following example indicates the major 15-lipoxygenase products of DPAn-3 and demonstrates production of mono- and dihydroxy derivatives analogous to those produced from DHA (Example 2) and DPAn-6 (Example 3).

DPAn-3 was treated with 15-lipoxygenase and analyzed by LC/MS/MS under conditions described in Example 2. FIG. 4A depicts the structures of the mono- and dihydroxy reaction products of this DPAn-3/15-LOX reaction. FIG. 4B depicts LC/MS spectrum of the monohydroxy product showing molecular ion (m/z of 345) and fragments characteristic of 17-hydroxy DPAn-3. Inset shows UV spectrum of this compound with the expected peak at 237 nm, characteristic of a conjugated diene. FIGS. 4C and 4D depict MS/MS spectra of the two dihydroxy products with molecular ions (m/z of 361) with fragments characteristic of 10,17-hydroxy DPAn-3 (4C) and 7,17-dihydroxy DPAn-3 (4D) indicated. The UV spectrum insets show the expected triplet peaks at 270 nm characteristic of a conjugated triene for 10,17-dihydroxy DPAn-3 and a single peak at 242 characteristic of two pairs of conjugated dienes separated by a methylene group for 7,17-dihydroxy DPAn-3.

Example 5

The following example indicates the major 15-lipoxygenase products of DTAn-6 and demonstrates production of a mono-hydroxy and a dihydroxy derivative analogous to those formed from DHA (Example 2), DPAn-6 (Example 3) and DPAn-3 (Example 4).

DTAn-6 was mixed with 15-lipoxygenase and analyzed by LC/MS/MS under conditions described in Example 2. FIG. 5A depicts the structure of the mono-hydroxy reaction product. FIG. 5B depicts an LC/MS spectrum of the mono-hydroxy product showing molecular ion (m/z of 347) and fragments characteristic of 17-hydroxy DTAn-6. Inset shows UV spectrum indicating the expected peak at 237 nm, characteristic of a conjugated diene. FIG. 5C depicts an LC/MS spectra of the dihydroxy product with molecular ion (m/z of 361) and fragments characteristic of 7,17-hydroxy DTAn-6 indicated. The UV spectrum inset shows the expected peak at 242, characteristic of two pairs of conjugated dienes separated by a methylene group.

Example 6

The following example shows the structure of the enzymatic oxylipin products produced from DPAn-6 after sequential treatment with 15-lipoxygenase followed by hemoglobin.

DPAn-6 (at a concentration of 100 μM) was mixed with soybean 15-lipoxygenase (20 μg/ml final concentration) with vigorous stirring at 4° C. Products were immediately extracted on Supelco Discovery DSC-19 cartridges using anhydrous ethanol for final elution. The hydroperoxy derivatives thus obtained were concentrated to 1.5 mM and were used for subsequent hemoglobin catalyzed reactions. The hydroperoxy derivatives (final reaction concentration, 30 μg/ml) were mixed with human hemoglobin (300 μg/ml, Sigma-Aldrich) in Dulbecco's phosphate buffered saline at 37° C. for 15 minutes. The reaction was acidified to pH 3 with glacial acetic acid and products purified by solid phase extraction. Reaction products were analyzed by LC-MS/MS. FIG. 6 illustrates the docosanoid products of the enzymatic reaction as deduced from the mass spectra (not shown).

Example 7

The following example indicates of the major 5-lipoxygenase products of DHA.

To a 10-ml reaction mixture containing 100 μM DHA (NuChek Prep, Elysian, Minn.) in 0.05M NaMES buffer, pH 6.3, 100 μM SDS and 0.02% $C_{12}E_{10}$, was added 200 μl of 10 U/μl potato 5-lipoxygenase (Caymen Chemicals, Minneapolis, Minn.). The reaction proceeded for 30 min at 4° C., and reaction products were reduced by addition of 1 ml of 0.5 mg/ml $NaBH_4$ Reaction products were extracted using solid phase C-18 cartridges and analyzed by LC/MS/MS as described in Example 2. Major reaction products as determined by tandem mass spectroscopy along with the diagnostic molecular ion and fragments are shown (FIG. 7).

Example 8

The following example indicates the major 5-lipoxygenase product of DPAn-6 and indicates production of a mono-hydroxy derivative analogous to the 5-LOX products of DHA (Example 7).

DPAn-6 (100 µM) was treated with 5-lipoxygenase as described in Example 7. Reaction products were analyzed by LC/MS/MS as in Example 2. Major reaction products as determined by tandem mass spectroscopy along with the diagnostic molecular ion and fragments are shown (FIG. 8).

Example 9

The following example indicates the major 5-lipoxygenase products of DPAn-3 and indicates production of mono- and dihydroxy derivatives analogous to the 5-LOX products of DHA (Example 7).

DPAn-3 (100 µM) was treated with 5-lipoxygenase as described in Example 7. Reaction products were analyzed by LC/MS/MS as in Example 2. Major reaction products as determined by tandem mass spectroscopy along with the diagnostic molecular ion and fragments are shown (FIG. 9).

Example 10

The following example indicates the major 12-lipoxygenase products of DHA.

For the enzyme reaction, 100 µl of 0.75 U/µl porcine leukocyte-derived 12-lipoxygenase (Caymen Chemicals, Minneapolis, Minn.) was added to a 10-ml solution containing 100 µM DHA (NuChek Prep, Elysian, Minn.) in 0.1M Tris-HCl, pH 7.5, 5 mM EDTA and 0.03% Tween-20. The reaction continued for 30 min at 4° C. and reaction products were reduced by adding 1 ml of 0.5 mg/ml $NaBH_4$. Reaction products were extracted using solid phase C-18 cartridges and analyzed by LC/MS/MS as described in Example 2. Major reaction products as determined by tandem mass spectroscopy, along with the diagnostic molecular ion and fragments, are shown (FIG. 10).

Example 11

The following example indicates the major 12-lipoxygenase products of DPAn-6 and indicates production of mono- and dihydroxy derivatives analogous to those from the DHA/12-LOX reaction (Example 10).

DPAn-6 (100 µM) was treated with 12-lipoxygenase as described in Example 10. Reaction products were analyzed by LC/MS/MS as in Example 2. Major reaction products as determined by tandem mass spectroscopy, along with the diagnostic molecular ion and fragments, are shown (FIG. 11).

Example 12

The following example indicates the major 12-lipoxygenase products of DPAn-3 and indicates production of mono- and dihydroxy derivatives analogous to those produced from the DHA/12-LOX reaction (Example 10) and the DPAn-6/12-LOX reaction (Example 11).

DPAn-3 (100 µM) was treated with 12-lipoxygenase as described in Example 10. Reaction products were analyzed by LC/MS/MS as in Example 2. Major reaction products as determined by tandem mass spectroscopy along with the diagnostic molecular ion and fragments are shown (FIG. 12).

Example 13

The following example describes a mass spectral analysis of oxylipins in algal DHA/DPAn-6 LCPUFA oil.

Algal-derived DHA+DPAn-6 oil (0.5 g) diluted in 1.5 ml hexane was run through a 15 mm×200 mm silica gel column, using increasing concentrations of ethyl acetate in hexane to elute the various lipid classes. Fractions containing lipids were identified by thin layer chromatography (TLC) using petroleum ether: ethyl ether: acetic acid (80:20:1) as the mobile phase and then further screened for mono- and dihydroxy docosanoids (m/z of 343, 345, 359, or 361) using LC/MS on a Hewlett Packard model 1100 liquid chromatograph equipped with electro spray ionization (ESI) and a Hewlett Packard model 1100 mass selective detector (MSD). Fractions containing hydroxyl docosanoid products were pooled, concentrated, and further analyzed by tandem mass spectroscopy (MS/MS) on a Applied Biosystems API QSTAR® Pulsar i Hybrid triple quadrapole-time of flight hybrid LC/MS/MS (Colorado University mass spectroscopy facility). The sample was introduced using direct infusion into an ESI source utilizing negative ionization.

Example 14

Figure 1:
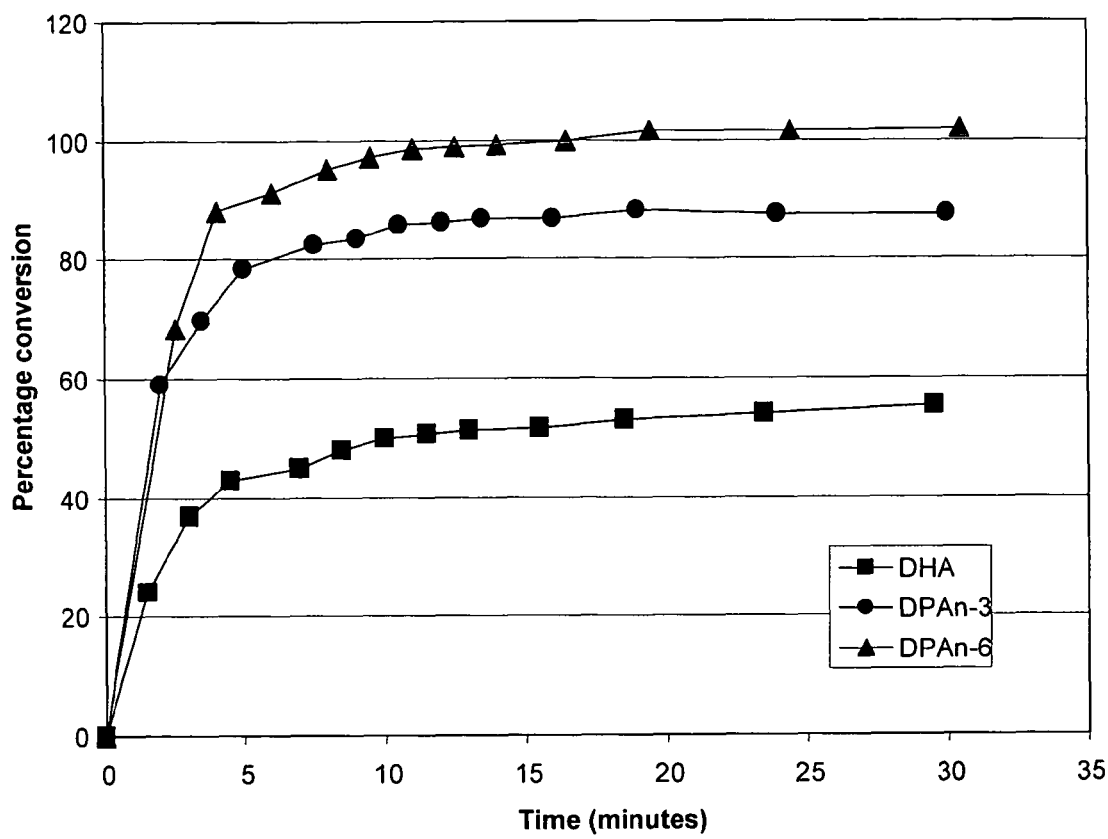
Figure 2A:
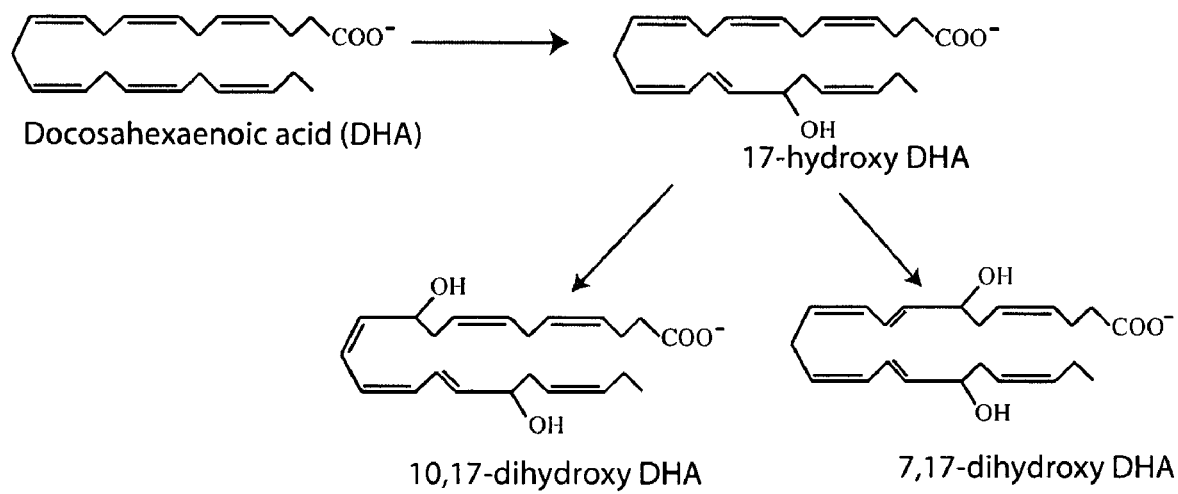
Figure 2B:
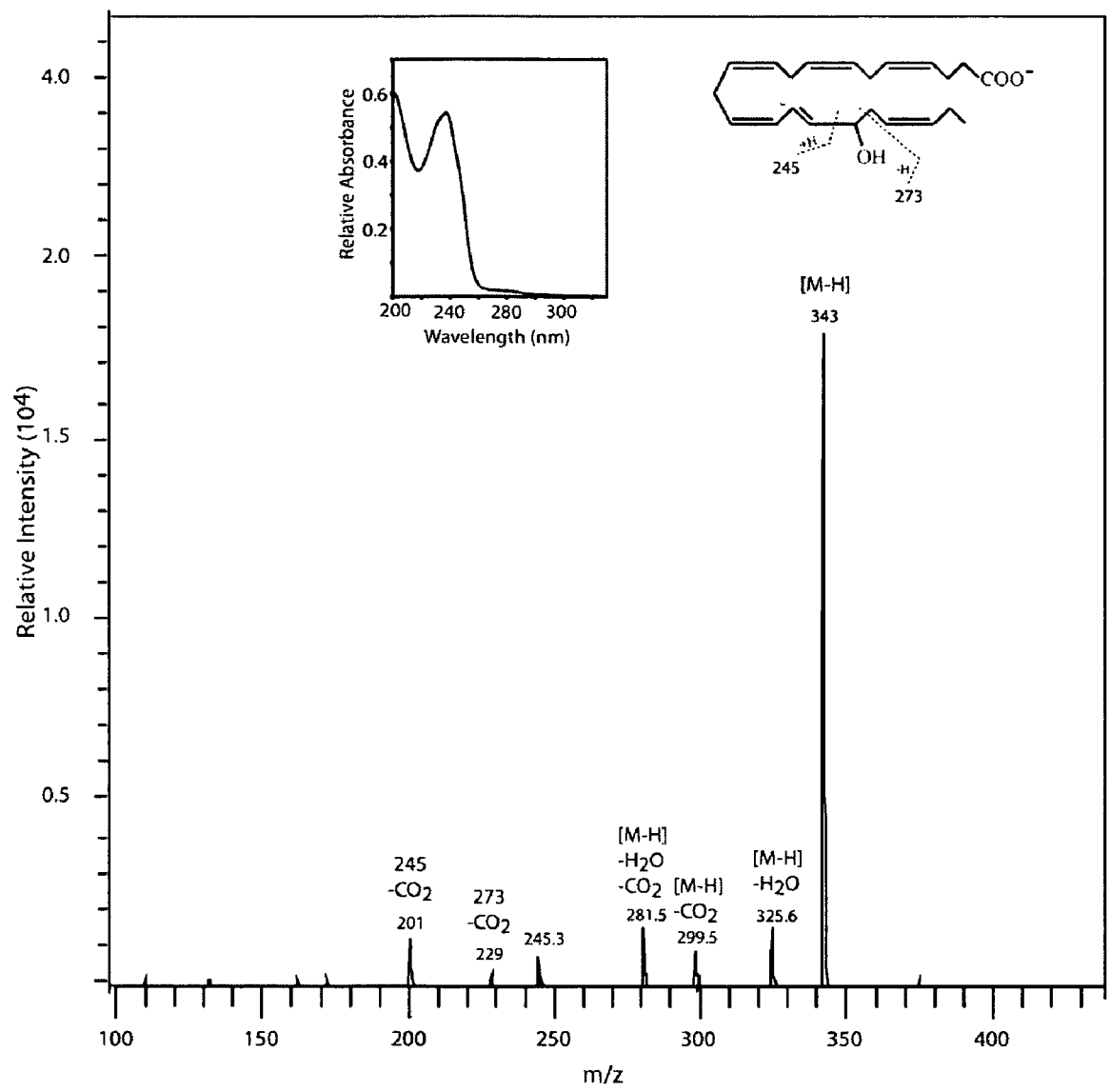
Figure 2C:
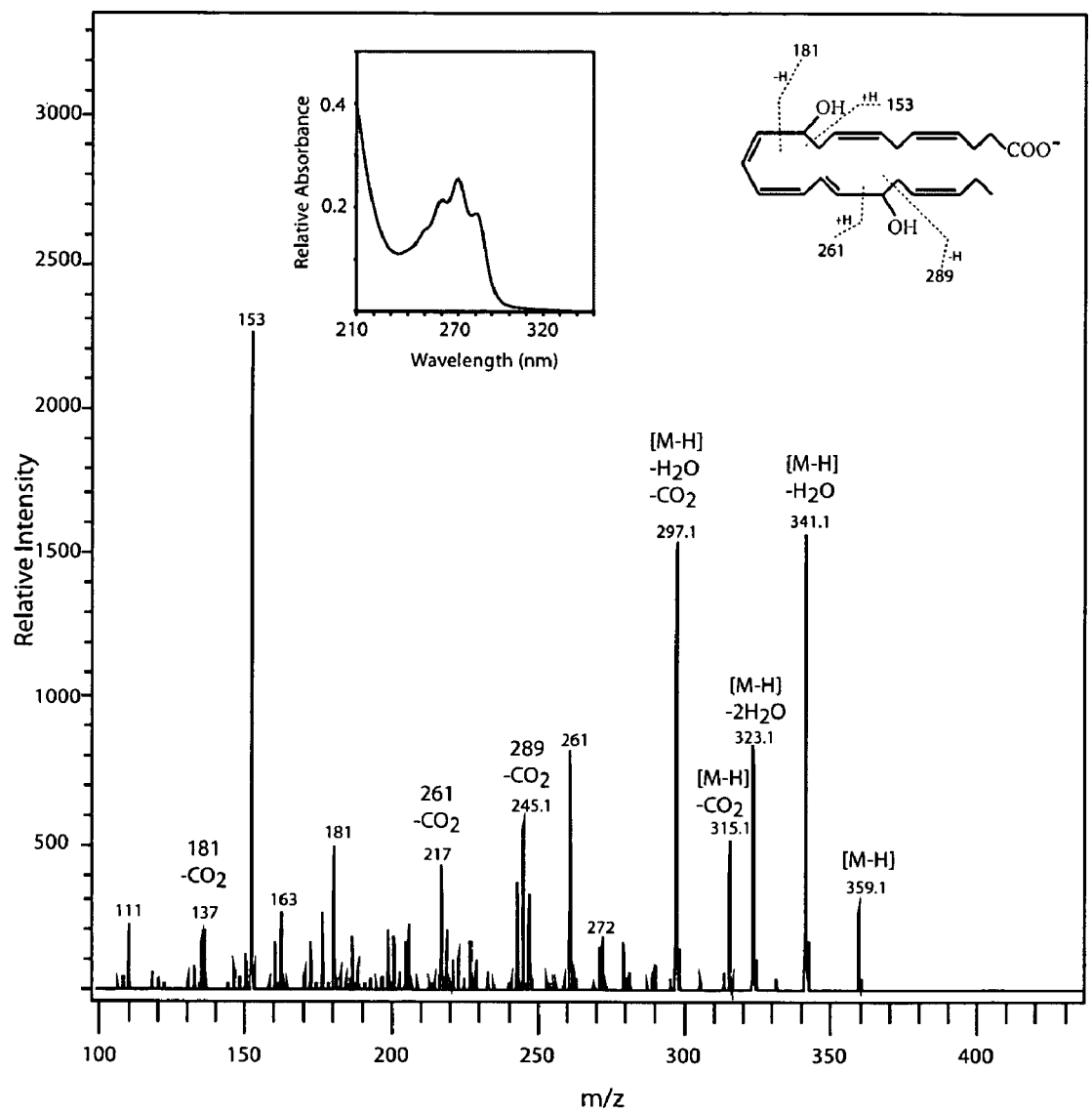
Figure 2D:
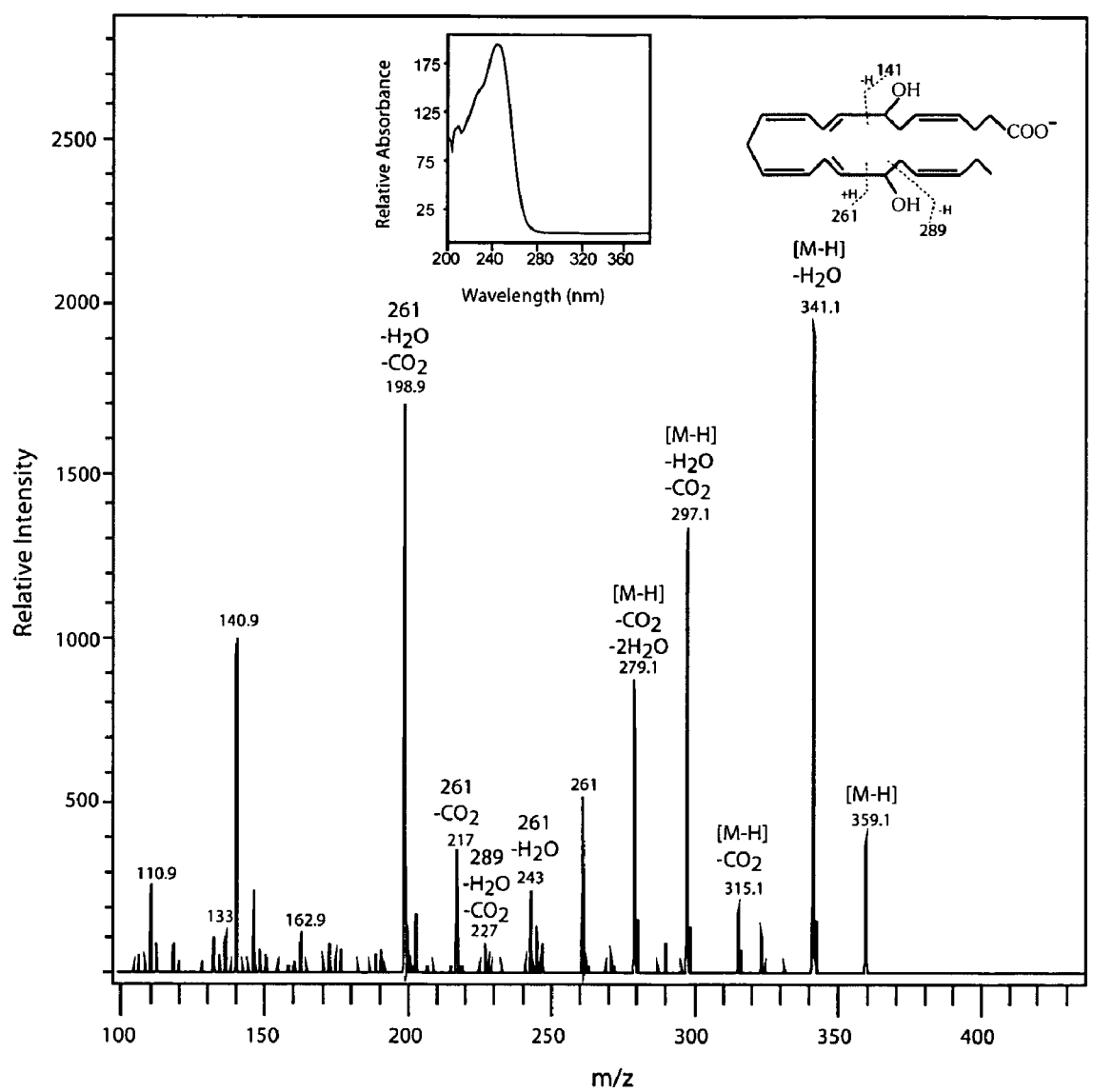
Figure 3A:
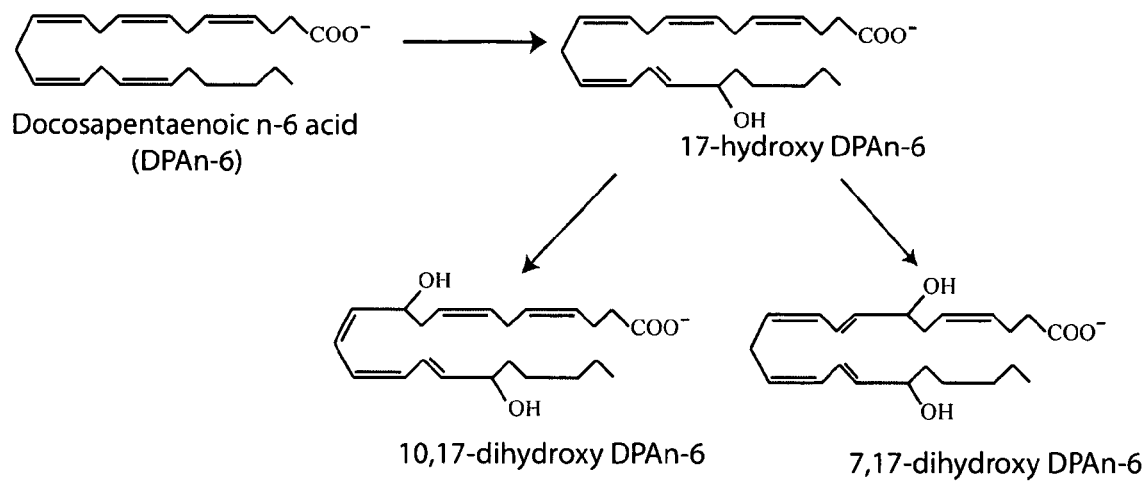
Figure 3B:
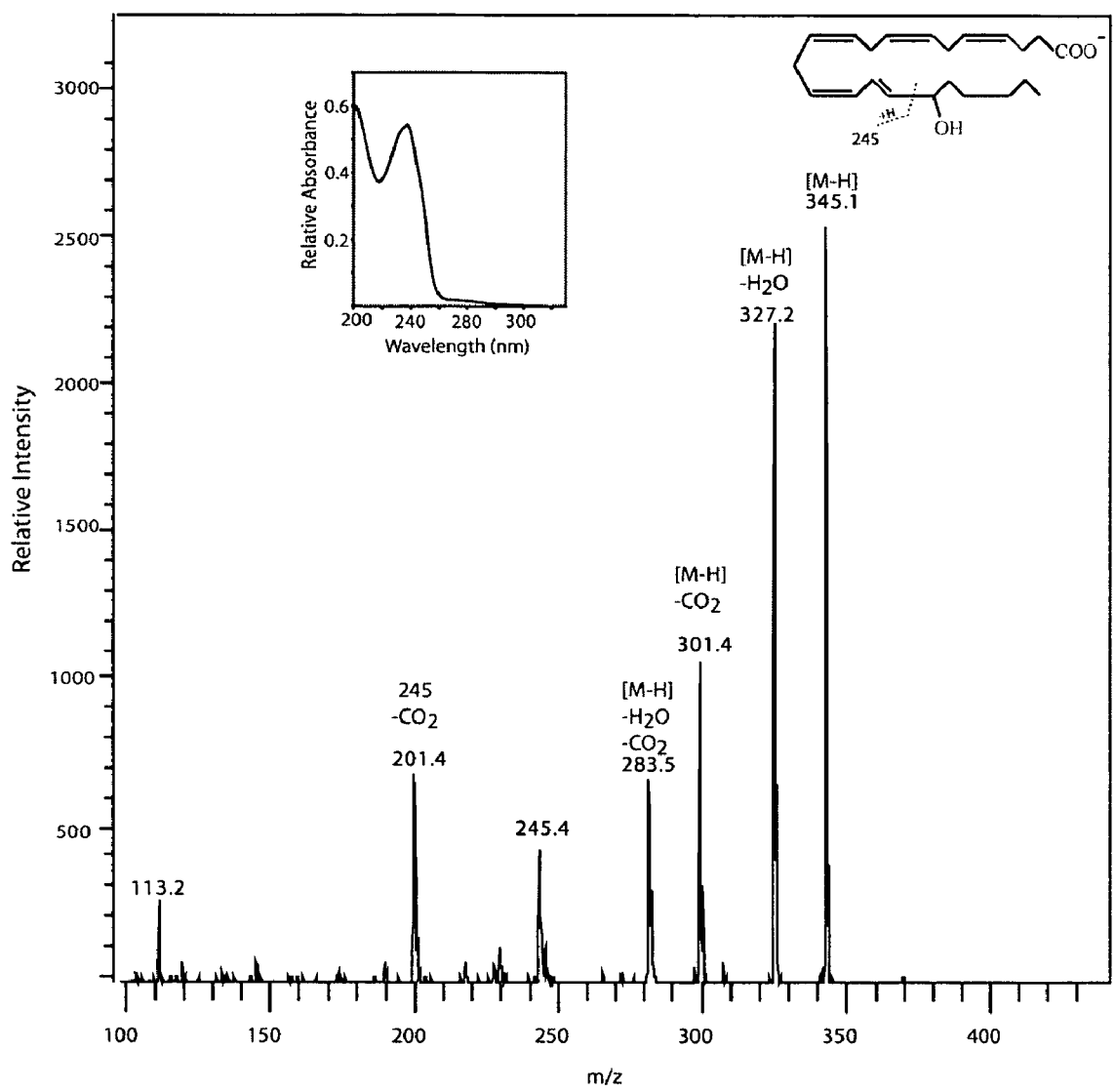
Figure 3C:
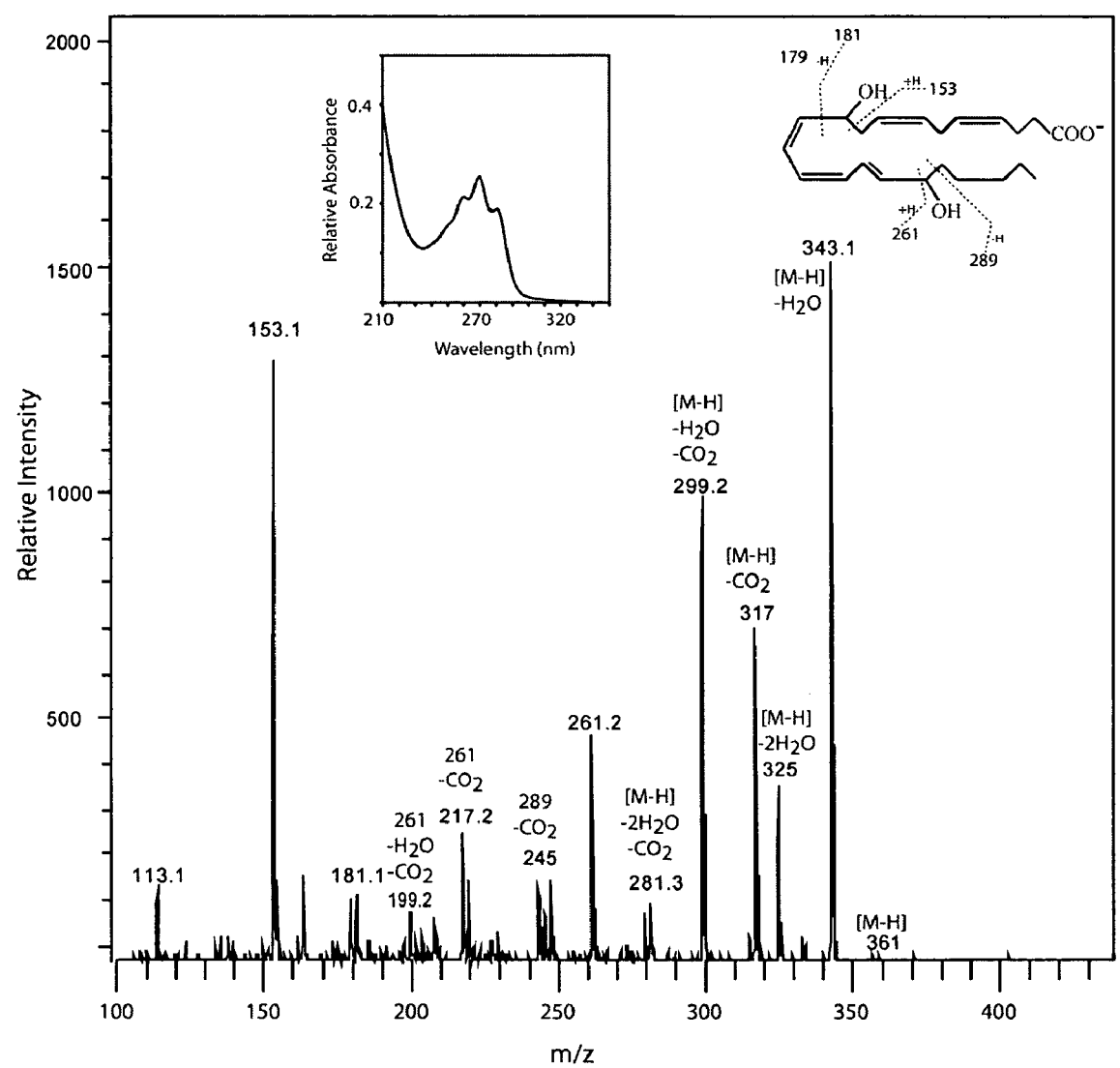
Figure 3D:
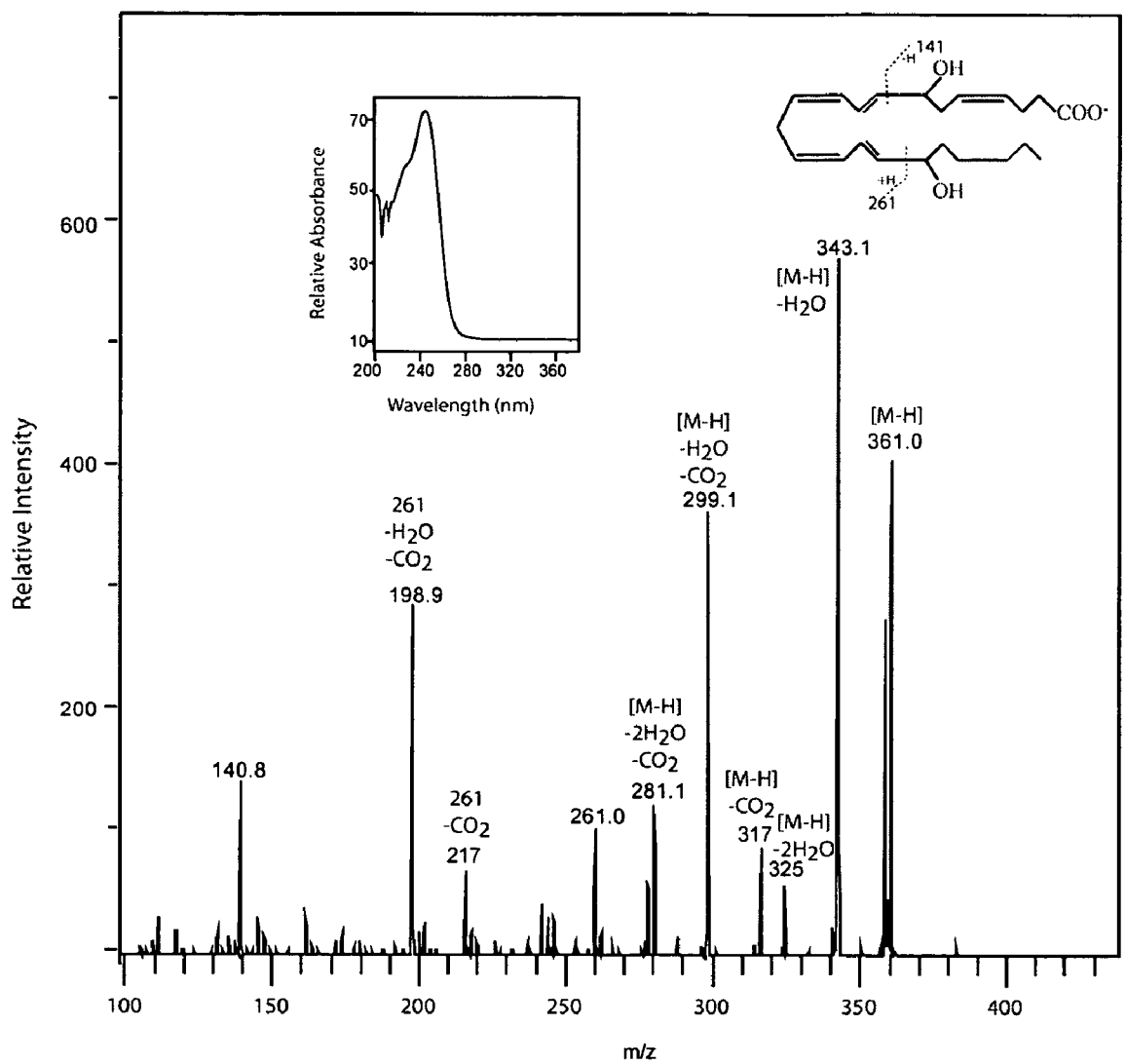
Figure 4A:
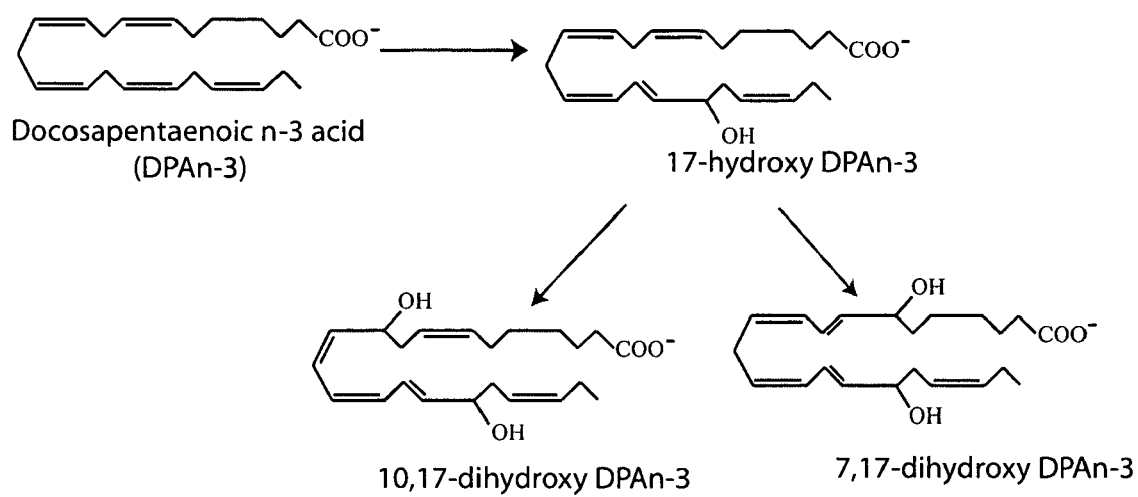
Figure 4B:
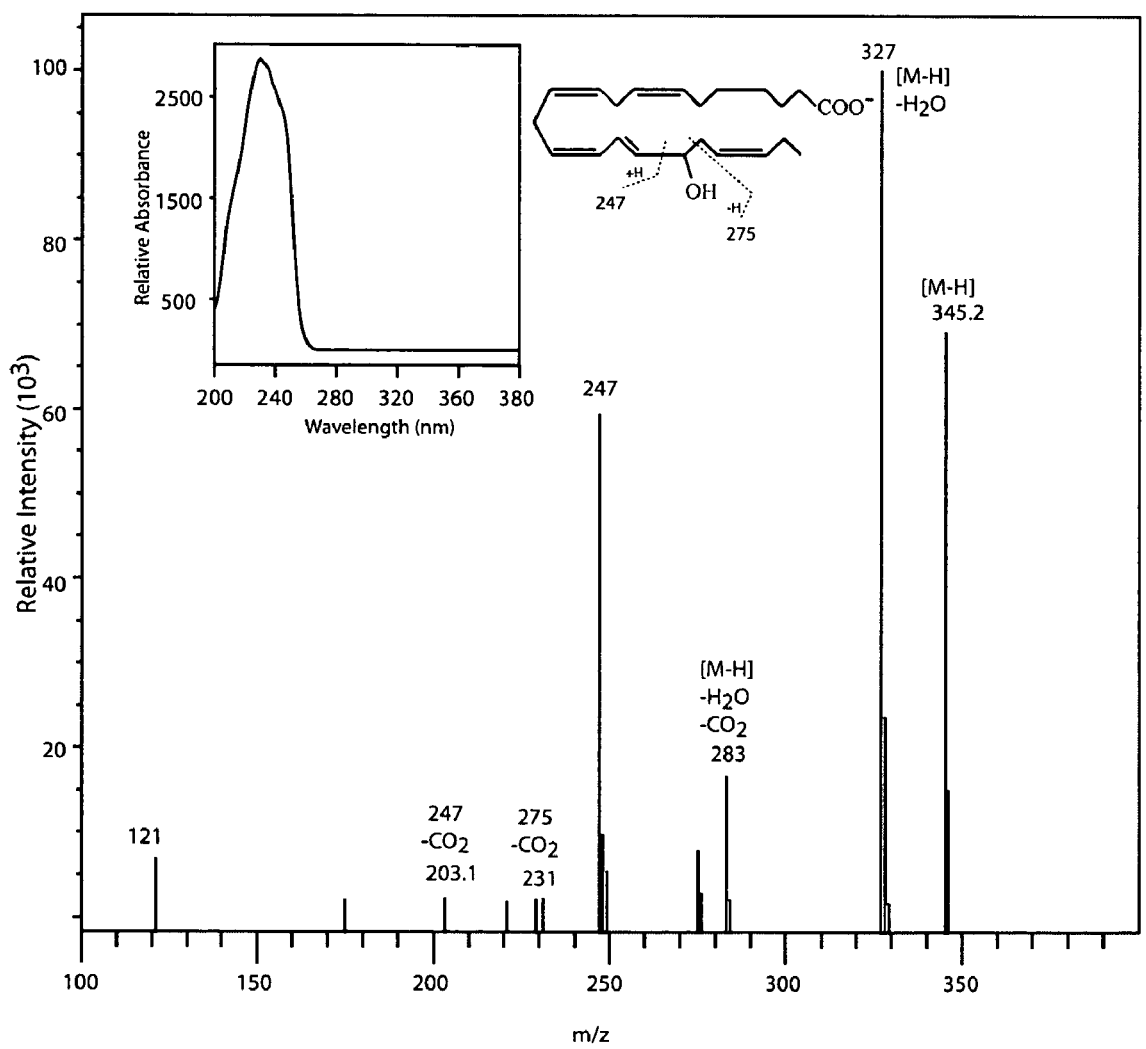
Figure 4C:
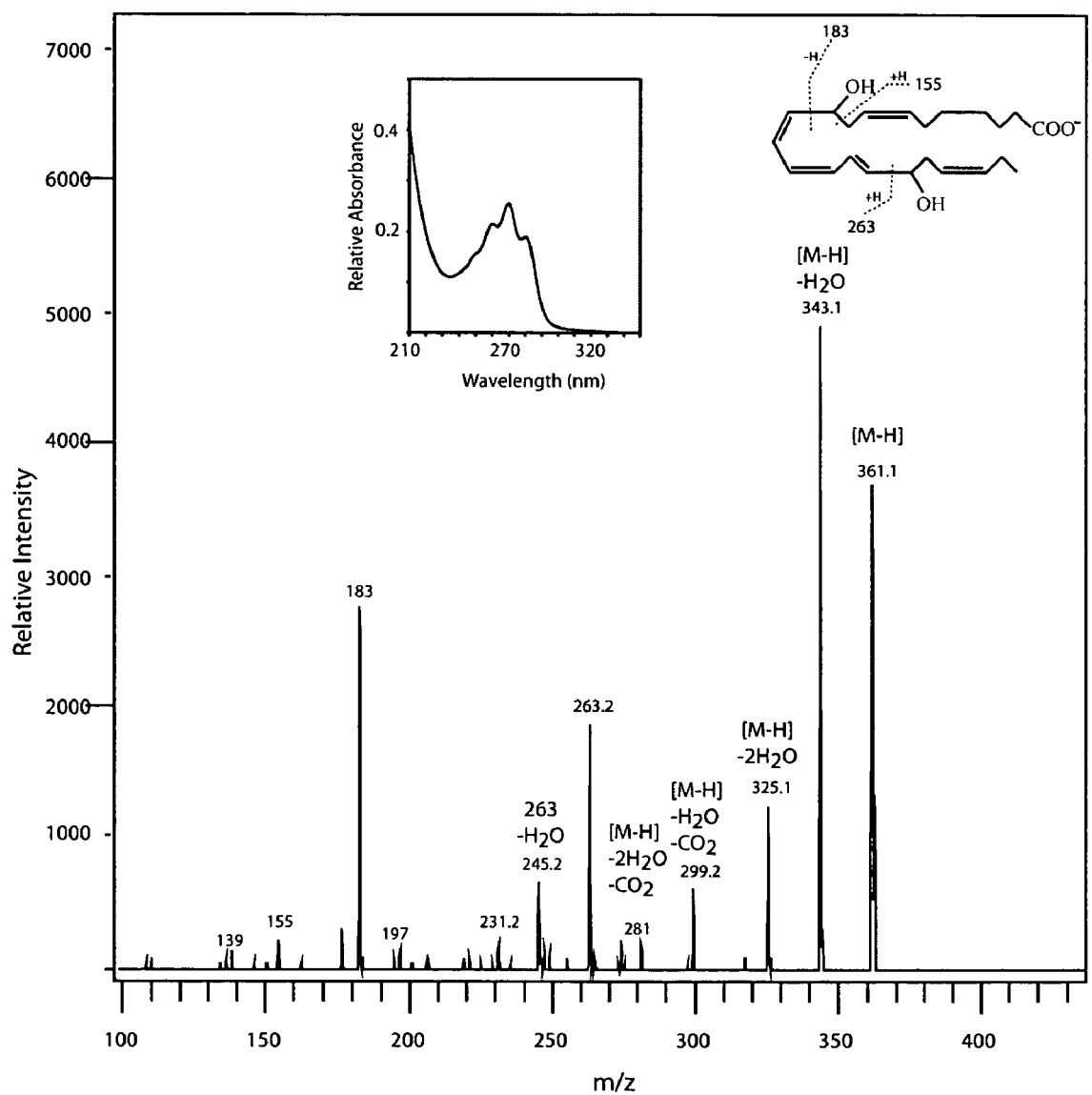
Figure 4D:
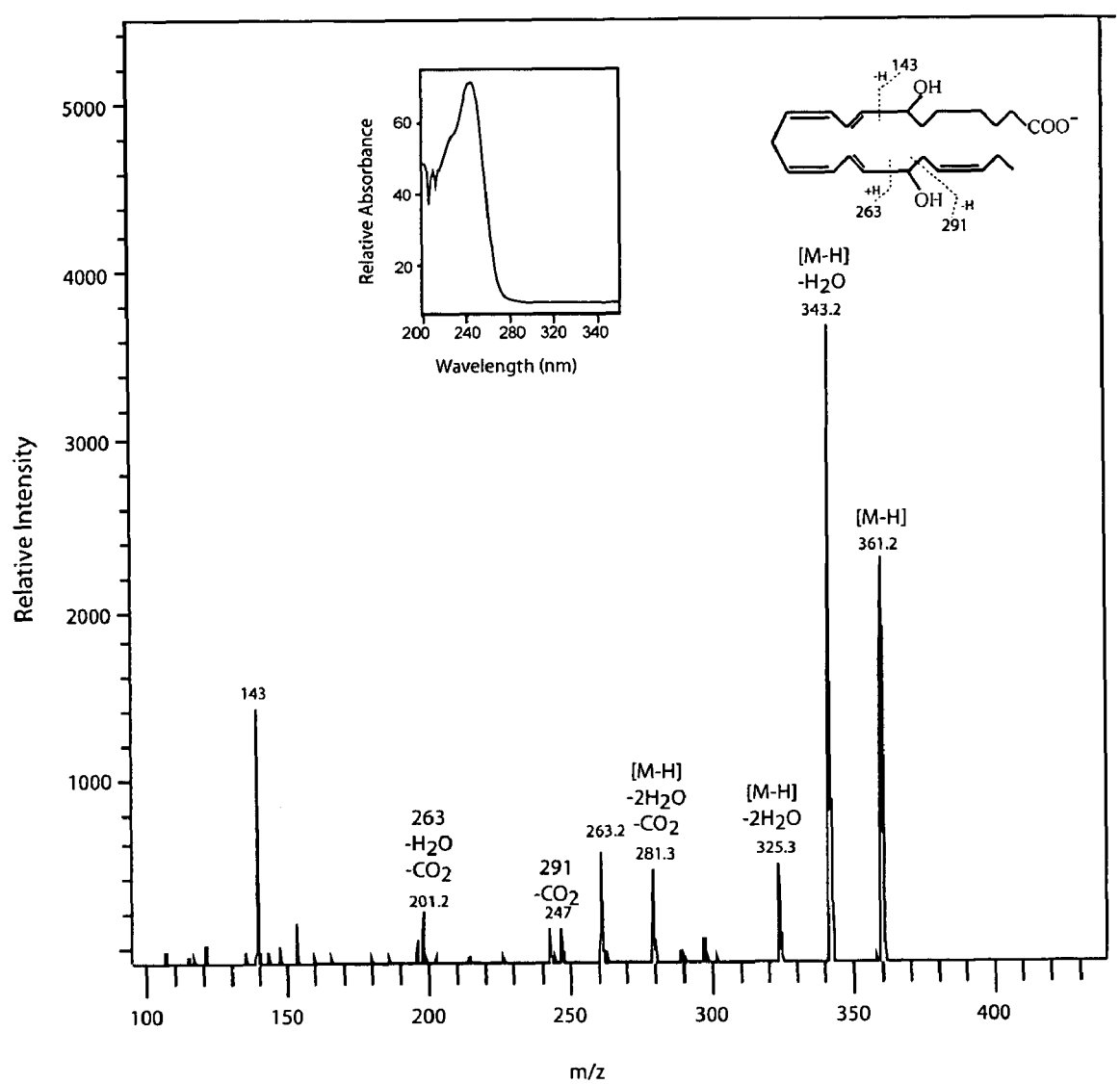
Figure 5A:
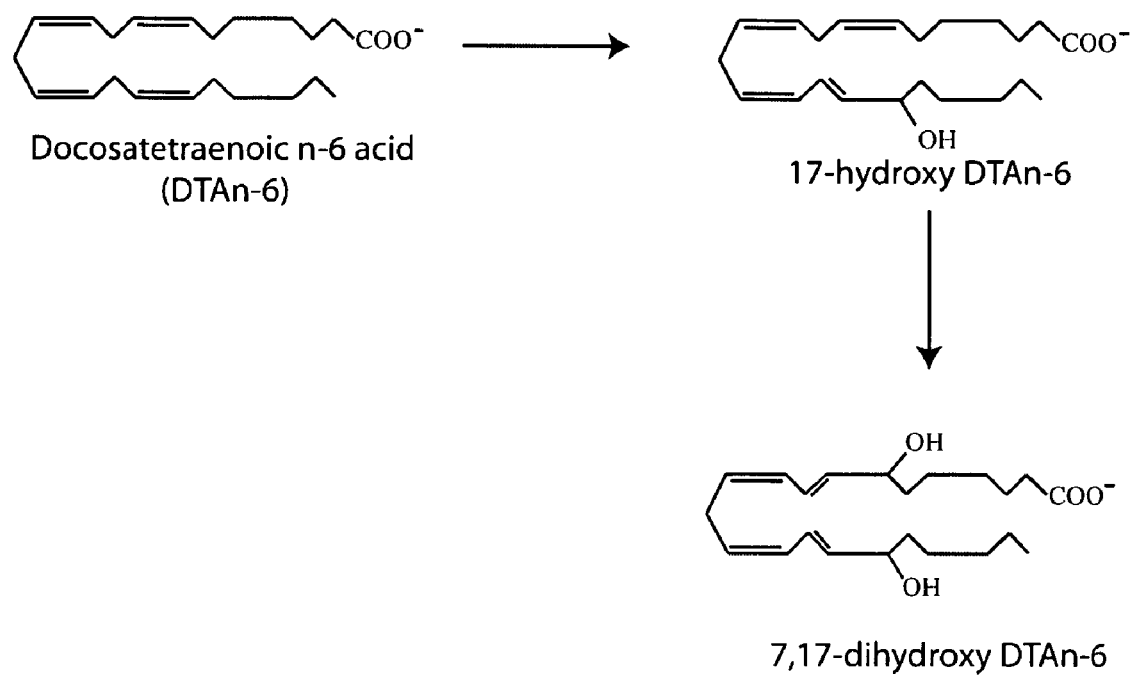
Figure 5B:
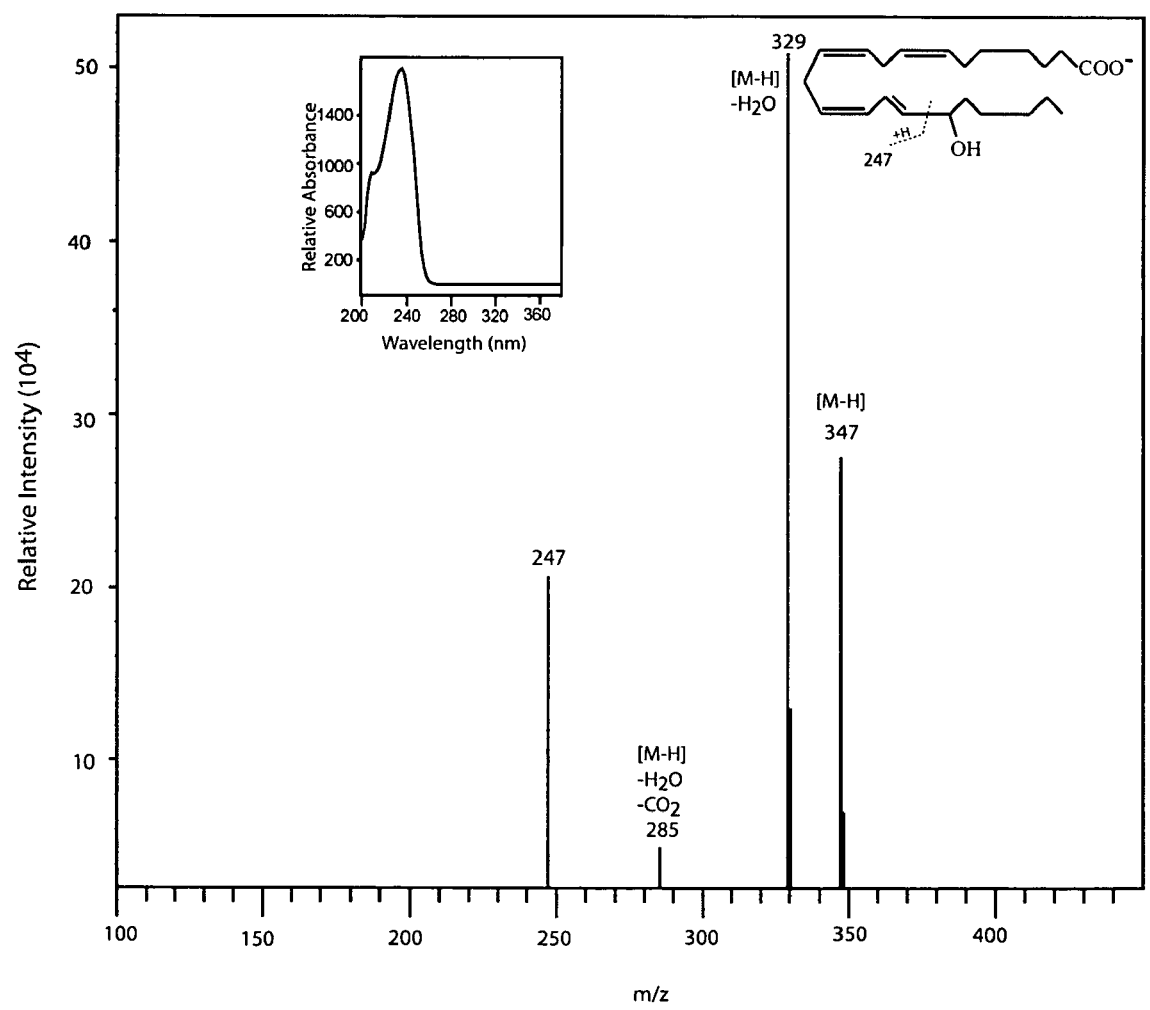
Figure 5C:
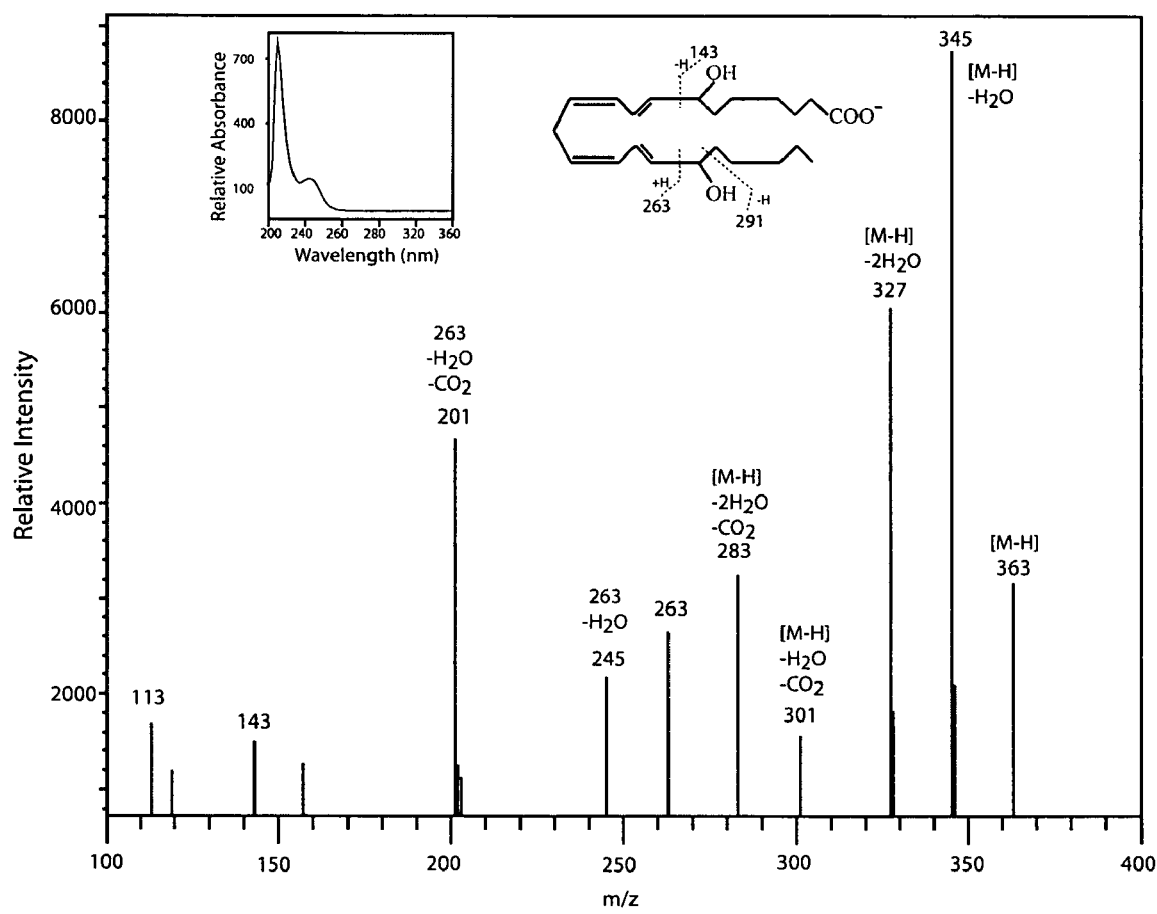
Figure 6:
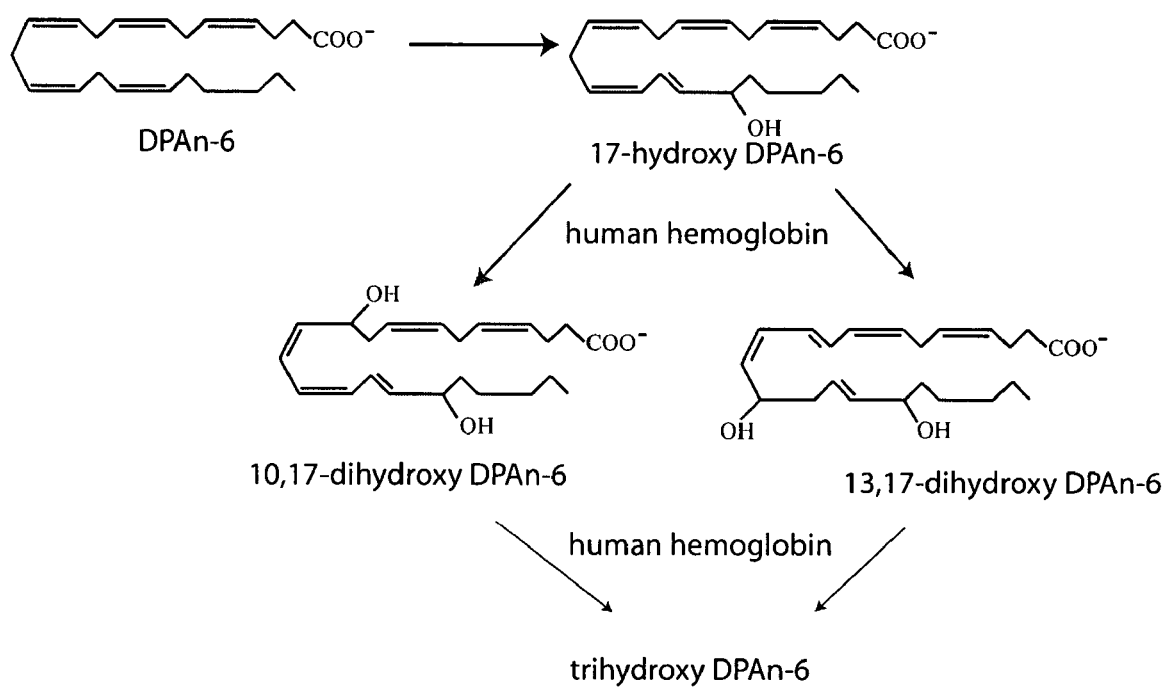
Figure 8:
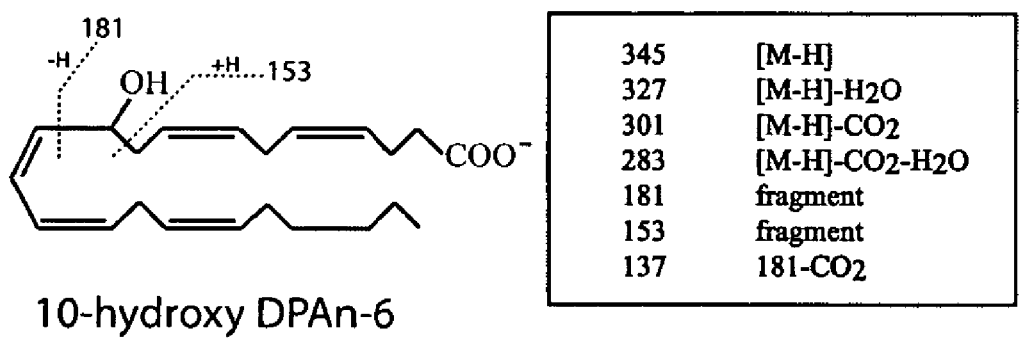
Figure 13:
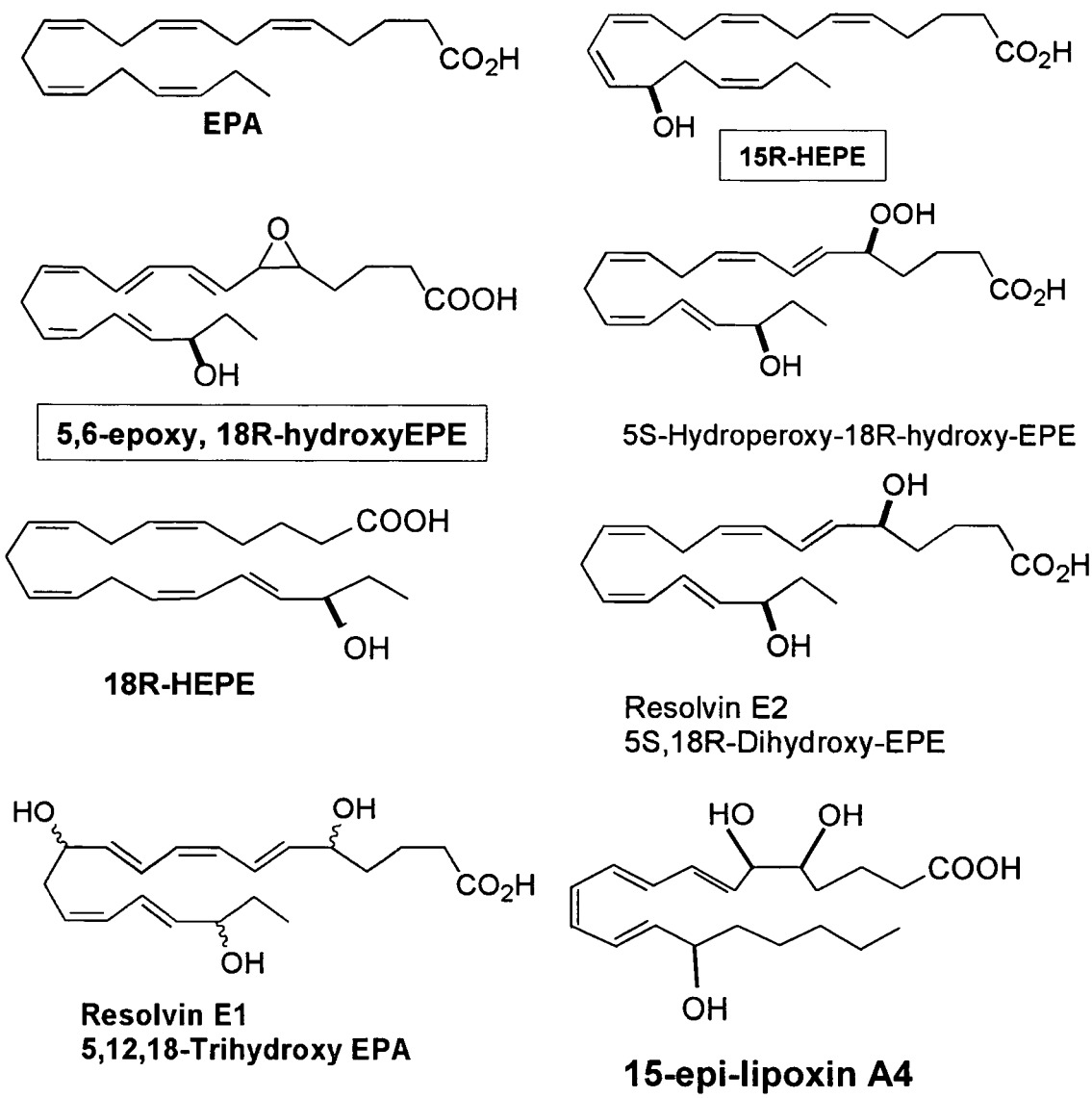
Figure 14A:
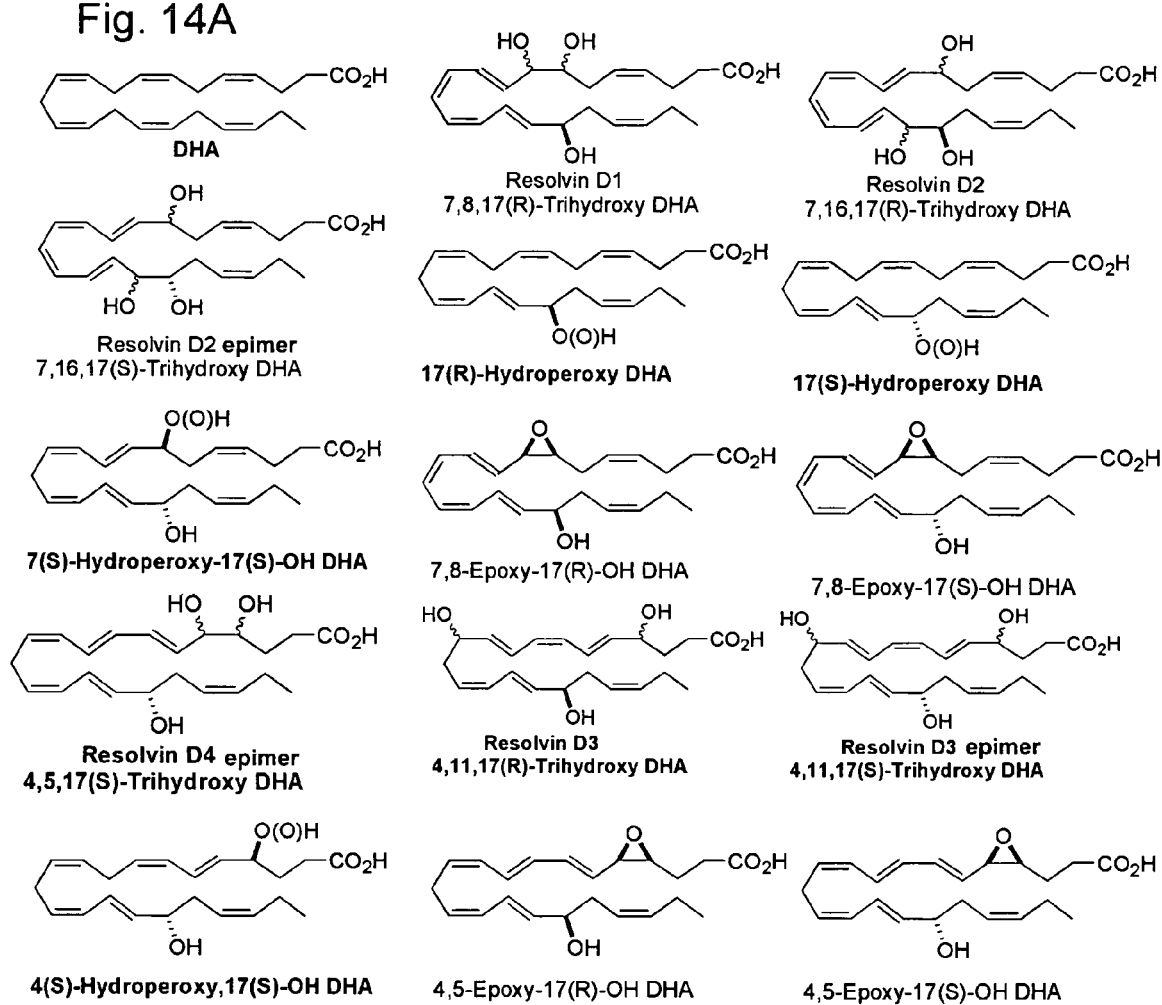
Figure 14B:
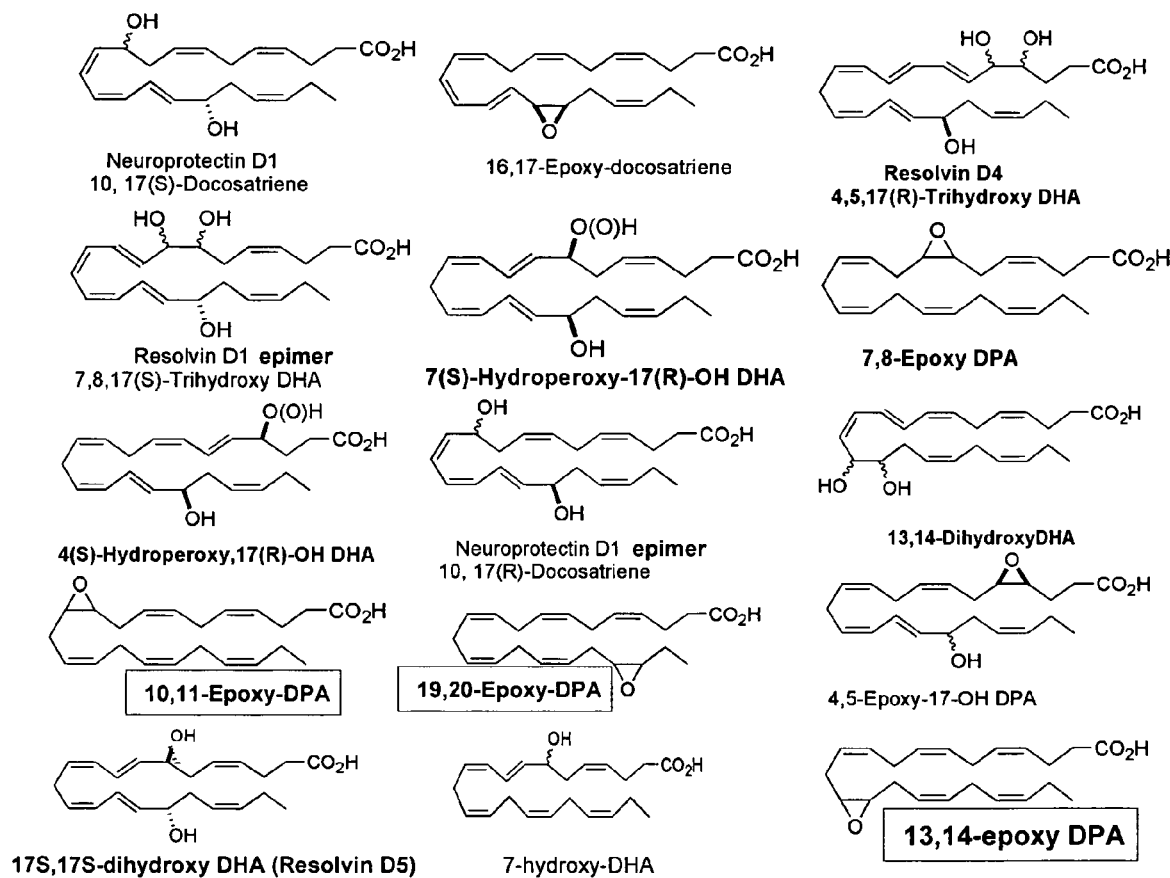
Figure 15:
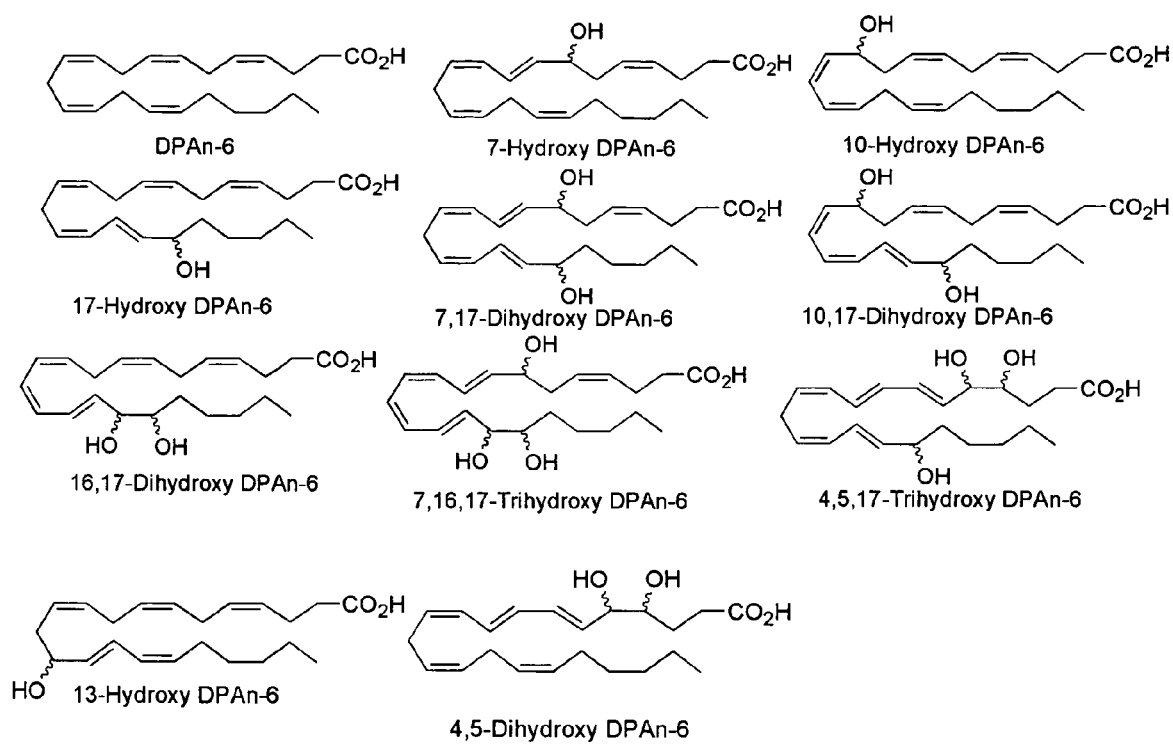
Figure 16:
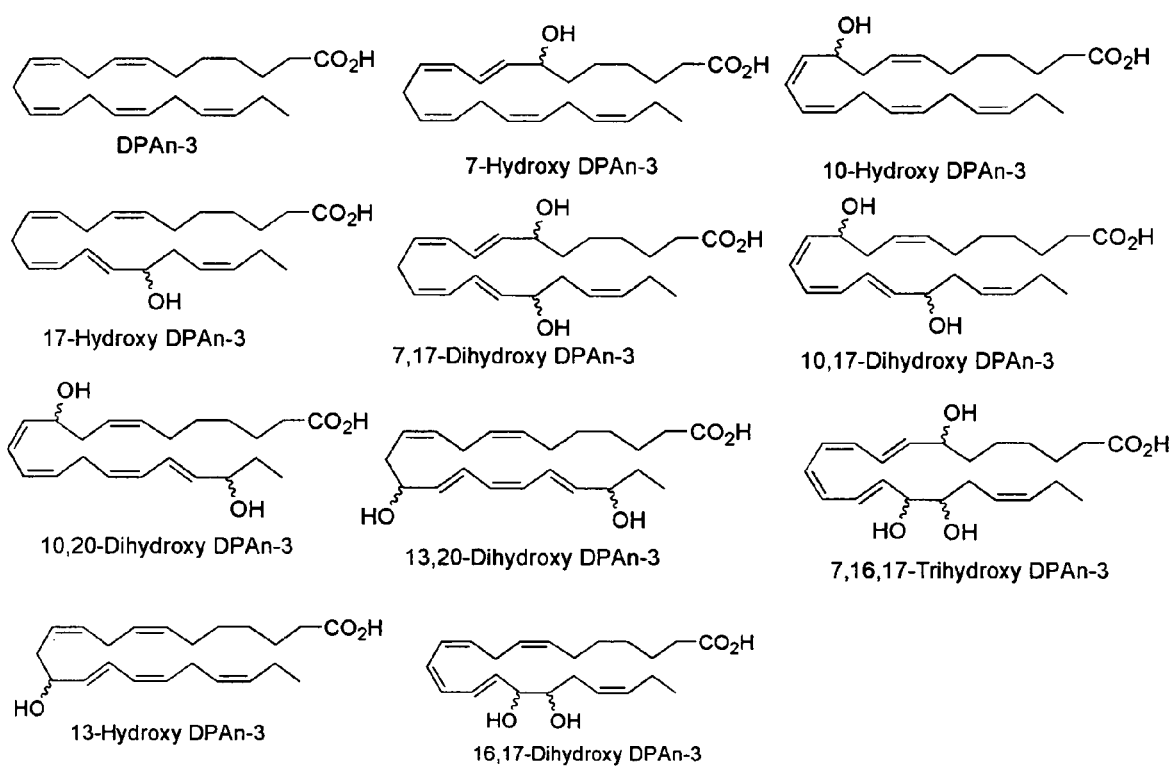
Figure 17:
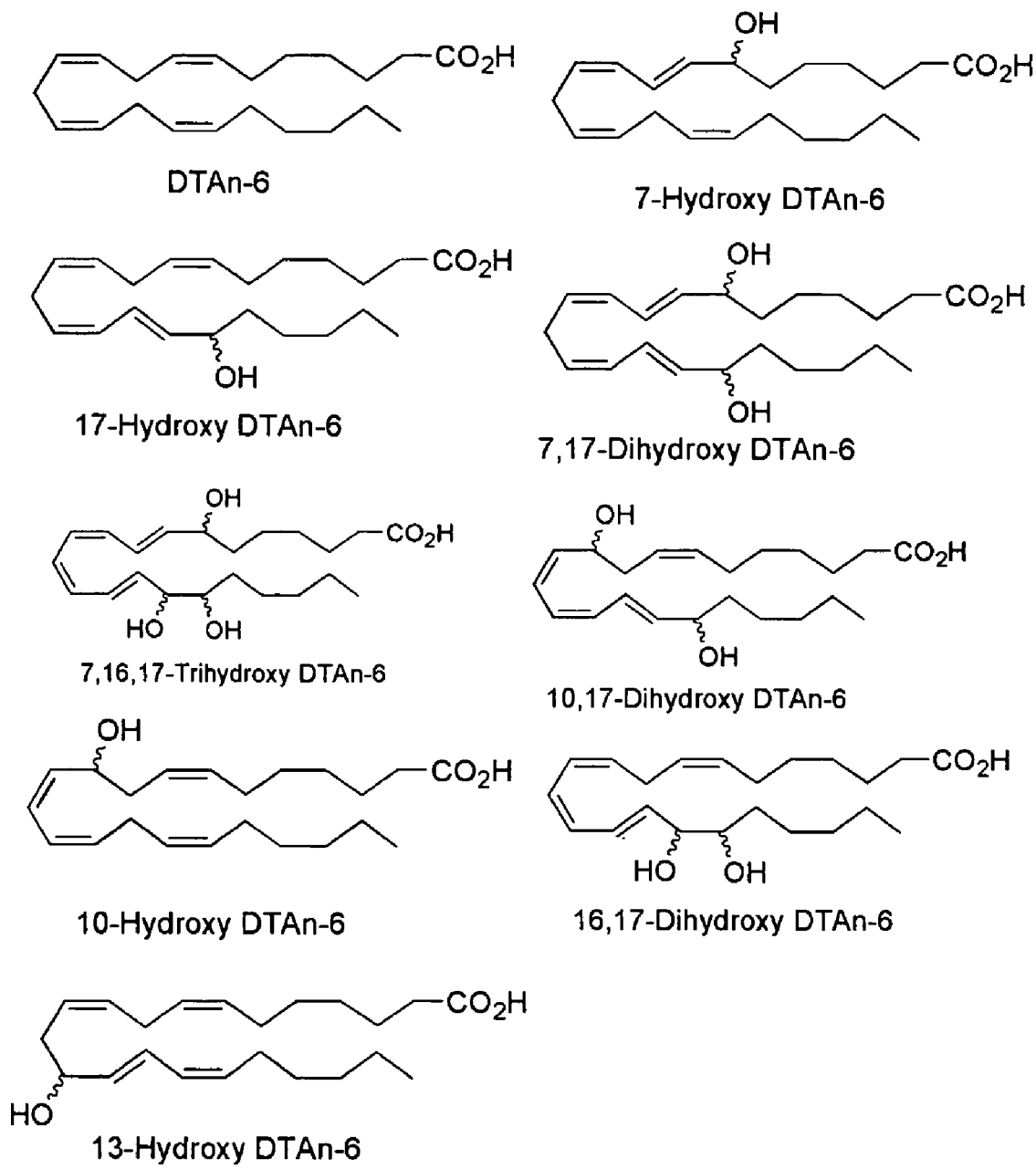
Figure 18A:
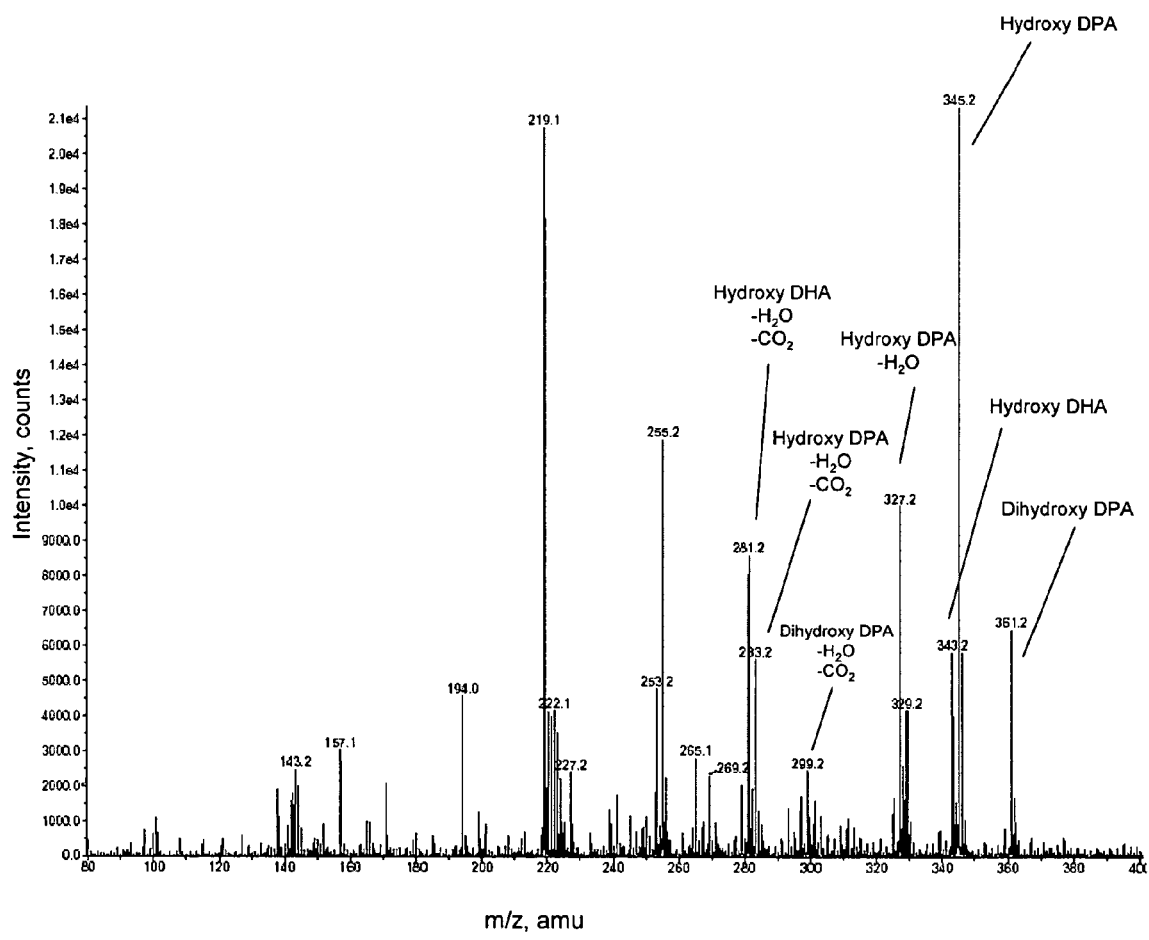
FIG. 18A depicts an MS total ion chromatograph (TIC) of the docosanoid fraction, indicating the presence of mono-hydroxy DPA (HDPA) and dihydroxy DPA (di-HDPA) ([M-H] of 345 and 361 m/z, respectively) and mono-hydroxy DHA (HDHA, [M-H] of 343 m/z) along with fragments corresponding to [M-H]—$H_2O$, [M-H]—$CO_2$ and [M-H]—$H_2O/CO_2$ that are characteristic fragments of these compounds.
Figure 18B:
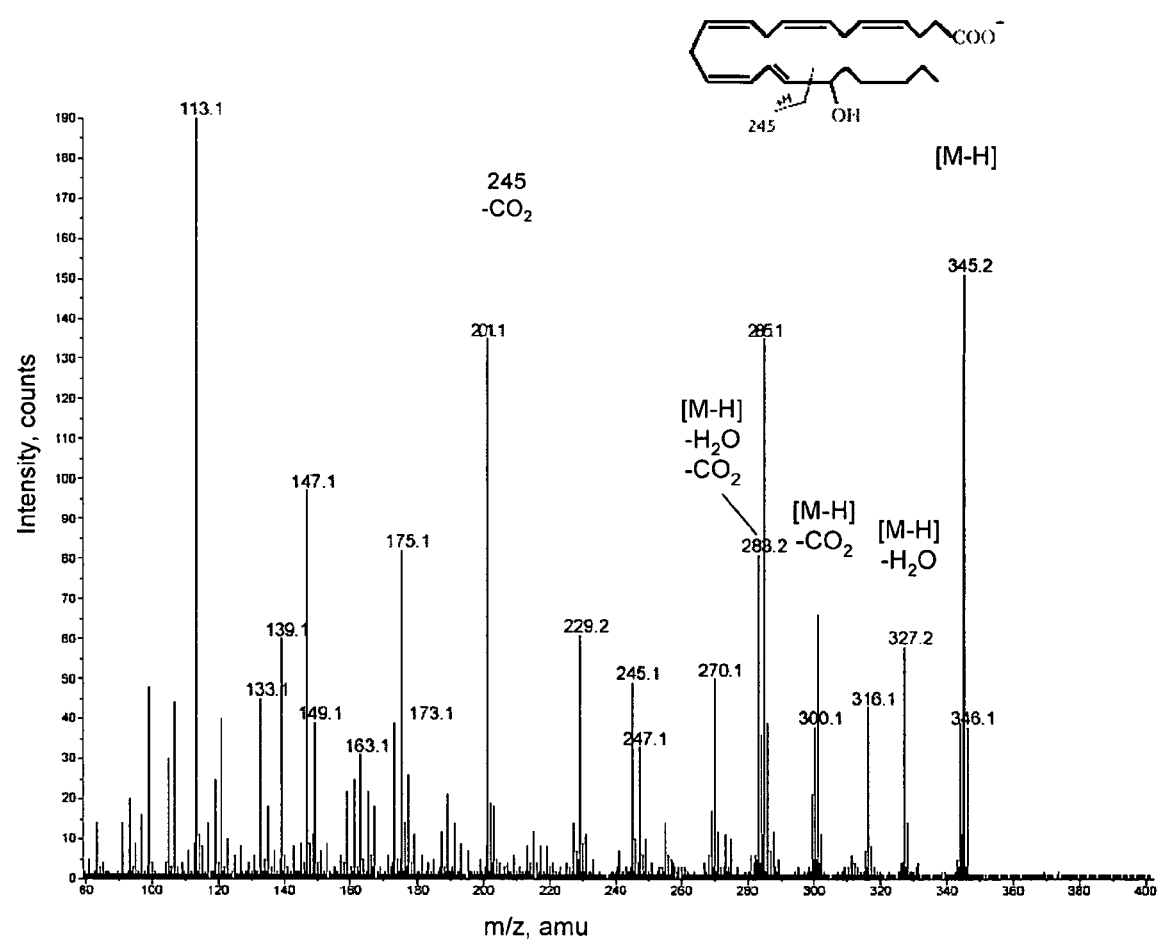
FIG. 18B depicts an MS/MS spectra of mono-hydroxy DPAn-6 ([M-H] 345 m/z) showing characteristic [M-H]—$H_2O$, [M-H]—$CO_2$ and [M-H]—$H_2O/CO_2$ fragments along with m/z 245 and 201 fragments indicating the presence of 17-HDPAn-6 in the oil.
Figure 18C:
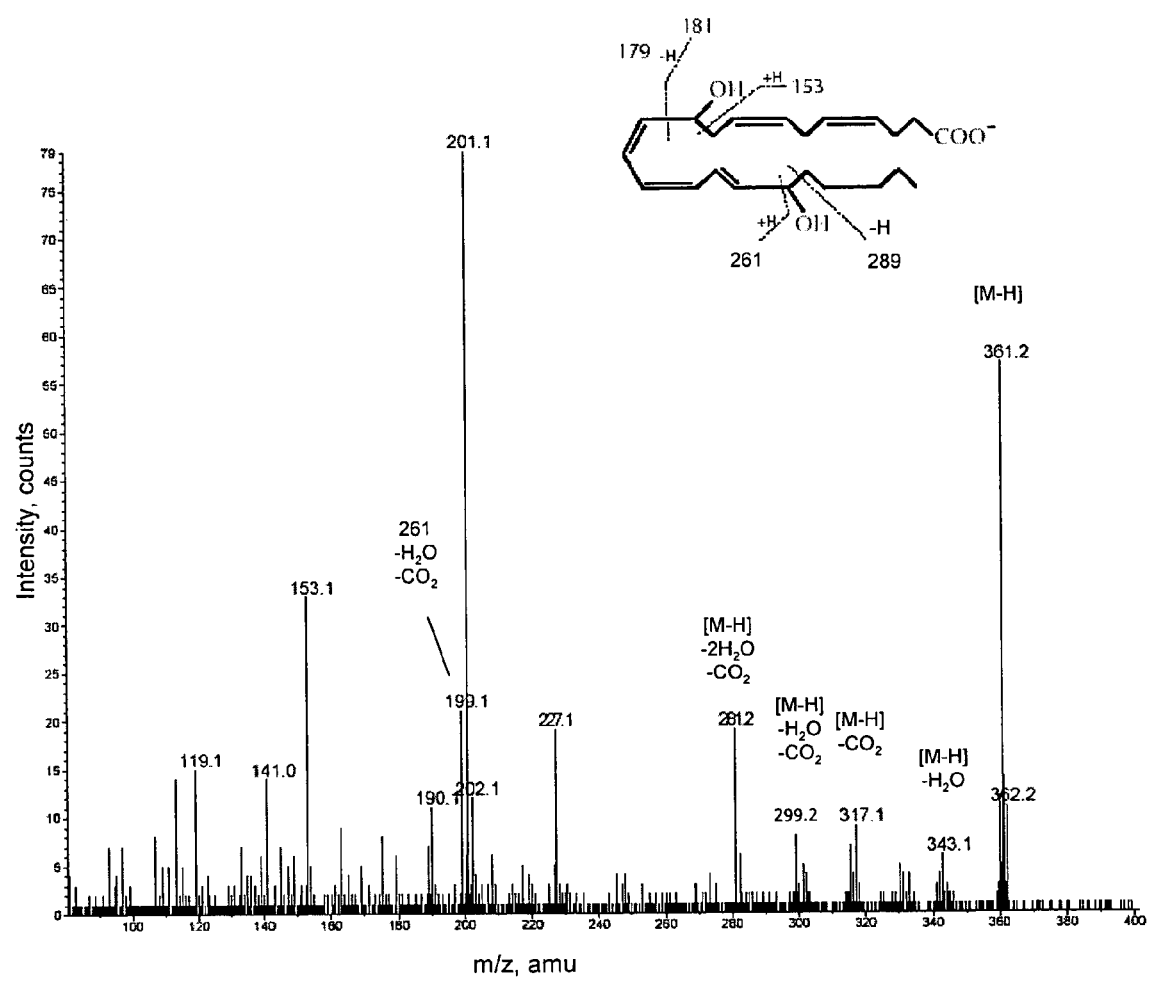
FIG. 18C depicts an MS/MS of dihydroxy-DPAn-6 with characteristic fragments corresponding to [M-H]—H2O (m/z 343), [M-H]—$CO_2$ (m/z 317) and [M-H]—$H_2O/CO_2$ (m/z 299), [M-H]-$2H_2O/CO_2$ (m/z 281) and fragments indicating the presence of 10,17-dihydroxyDPAn-6 (m/z 261-$H_2O$/$CO_2$; 153).
Figure 19:
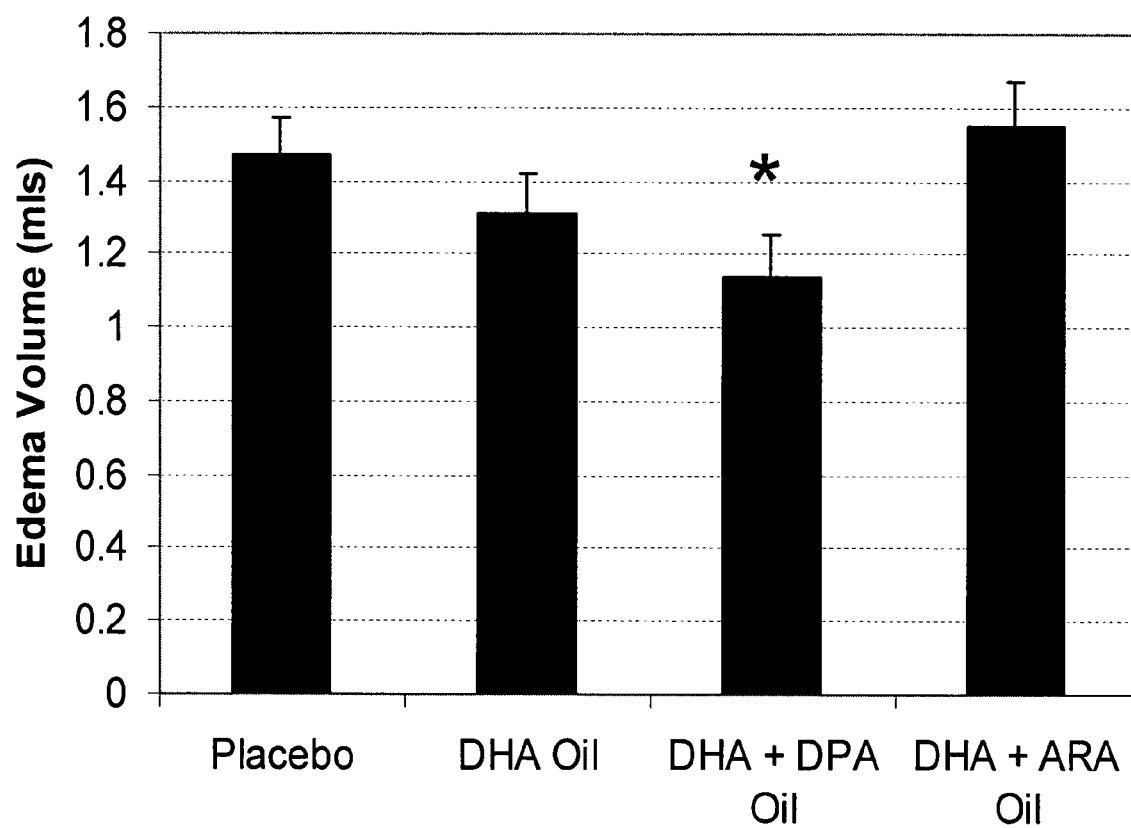

The following example shows the results of a rat paw edema study in which various combinations of LCPUFAs were fed to the animals Adult, male, Sprague Dawley rats (n=10/treatment group) were fed modified AIN-76 diets formulated to include 1.2% DHA, 1.2% DHA+0.44% DPAn-6, or 1.2% DHA+0.46% arachidonic acid (ARA) for 4 weeks. Carrageenan (1%) was used to induce hind paw edema on Day 14 (left paw) and Day 28 (right paw) of feeding. Edema was measured plethysmographically using water displacement 3 hours post-injection. Day 28 means (±stdev) are shown in FIG. 19. Similar results were obtained on day 14. *$p \leq 0.05$.

FIG. 19 shows that the oil containing a combination of DHA and DPAn-6 produced a statistically significantly better reduction in edema volume than DHA alone or DHA and ARA. The omega-6 fatty acid ARA reversed the anti-inflammatory activity of DHA in this model.

Example 15

The following example demonstrates the potent anti-inflammatory effect of the DPAn-6-derived oxylipins 17-hydroxy DPAn-6 and 10,17-dihydroxy-DPAn-6 in a mouse dorsal air pouch model.

Pure 17R-hydroxy DHA (17R-HDHA) was purchased from Caymen Chemicals (Ann Arbor, Mich.). Docosanoids 17-hydroxy-DPAn-6 (17-HDPAn-6) and 10,17-dihydroxyDPAn-6 (10,17-HDPAn-6) were synthesized biogenically from DPAn-6 (NuChek Prep, Elysian, Minn.) using soybean 15-lipoxygenase (Sigma-Aldrich) and purified by HPLC as described in Example 2. Organic solvents were evaporated and the compounds were re-dissolved in phosphate buffered saline (PBS), filter sterilized and concentrations were adjusted to 1000 ng/ml using molar extinction coefficients of 28,000 and 40,000 $M^{-1}cm^{-1}$ for the mono- and dihydroxy docosanoids, respectively. Female C57/B16 mice (n=10 mice per group) were injected with sterile air subcutaneously in the back to initiate dorsal air pouches. Six days later, 0.9 ml sterile PBS followed by 100 ng docosanoid in 0.1 ml PBS or PBS alone were administered by intra-pouch injection. This injection was followed within 5 min by intra-pouch injection of 100 ng of mouse recombinant TNFα (Peprotech, Inc, NJ, USA) in 0.1 ml PBS. Control animals received no TNFα. As a positive control, 2 mg/kg indomethacin (Calbiochem, San Diego, Calif.) was administered intraperitoneally 30 min prior to administration of TNFα. Four hours after TNFα administration, air pouch exudates were removed and cells were stained with Turk's solution and counted. Exudates were frozen for later cytokine analyses using commercial ELISA kits. Bars represent group (n=10) means (±stdev). Groups were compared using Student's t test, with p values indicated.

Figure 20A:
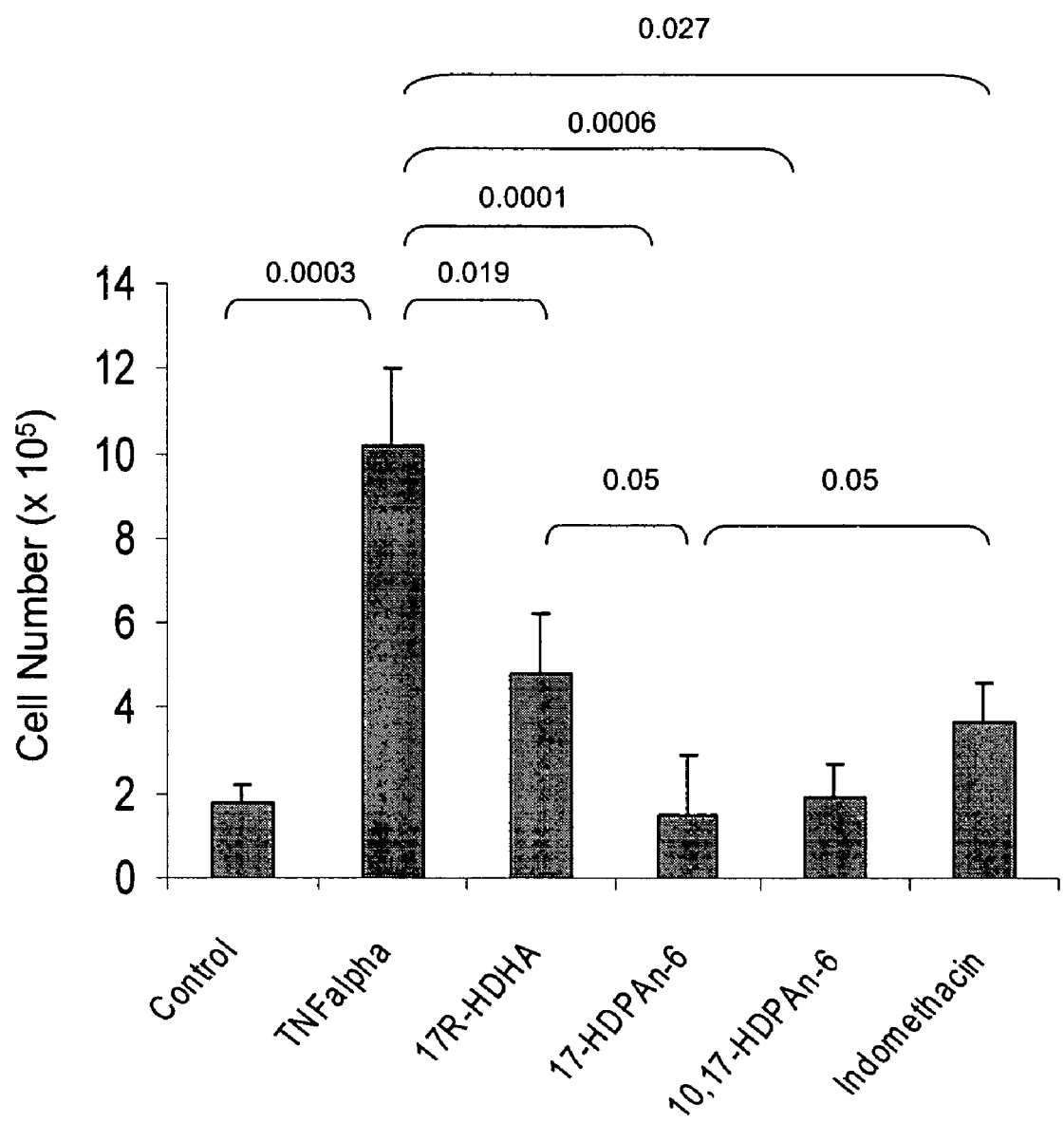

FIG. 20A shows the total cell migration into air pouch exudates. 17-hydroxy DPAn-6 and 10,17-dihydroxy DPAn-6 resulted in significant reductions in the total number of cells in the pouch, due to reductions in both the number of neutrophils and macrophages (not shown). 17-hydroxy DPAn-6 was more potent than both 17R-hydroxy DHA and indomethacin in reducing cell infiltration.

Figure 20B:
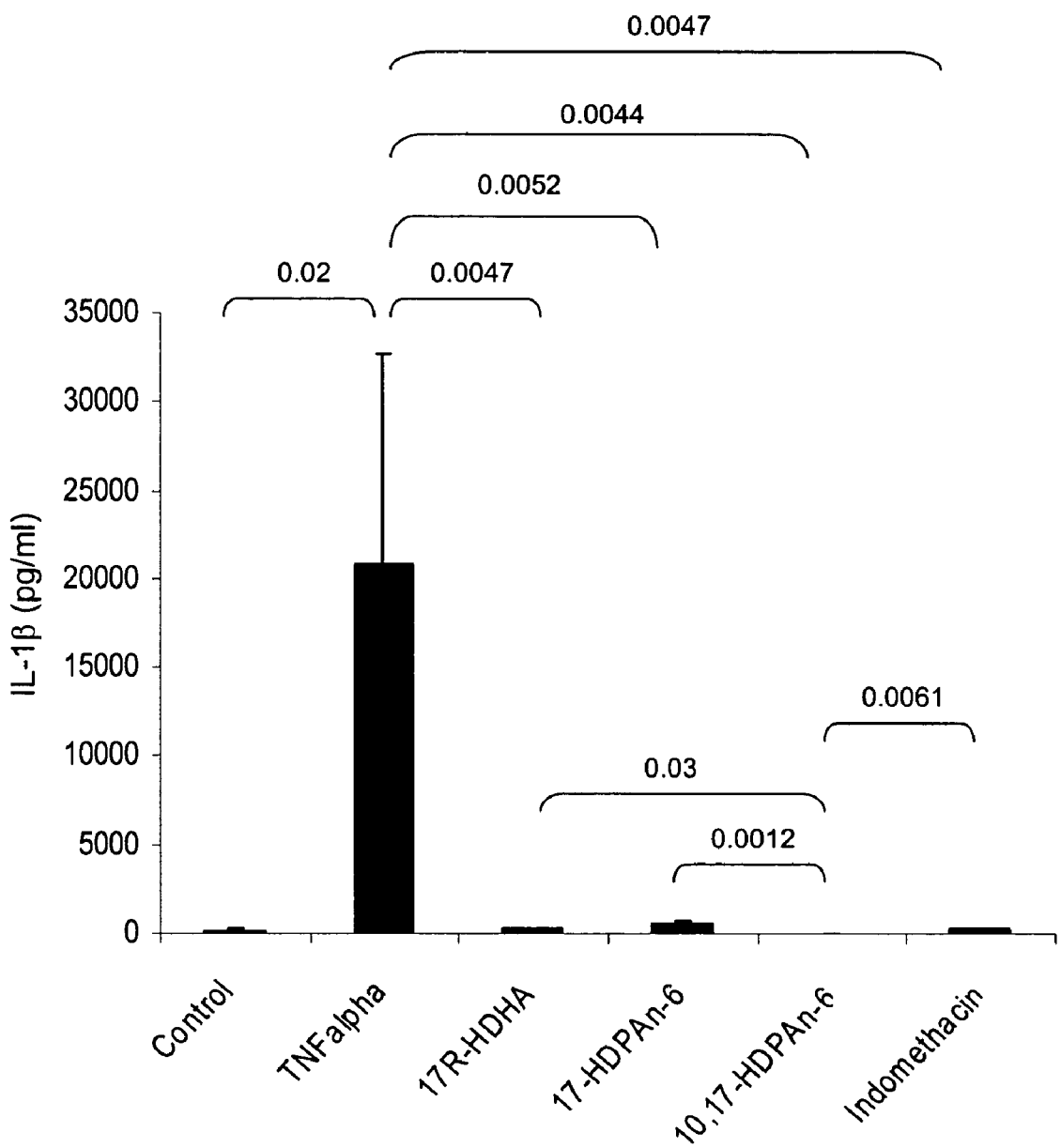

FIG. 20B shows the IL-1β concentrations in air pouch exudates. Both 17-hydroxy DPAn-6 and 10,17-dihydroxy DPAn-6 resulted in significant reductions in the secretion of the potent pro-inflammatory cytokine IL-1β, with the reduction produced by 10,17-dihydroxy DPAn-6 significantly larger than with that produced by either the DHA oxylipin derivative or indomethacin.

Figure 20C:
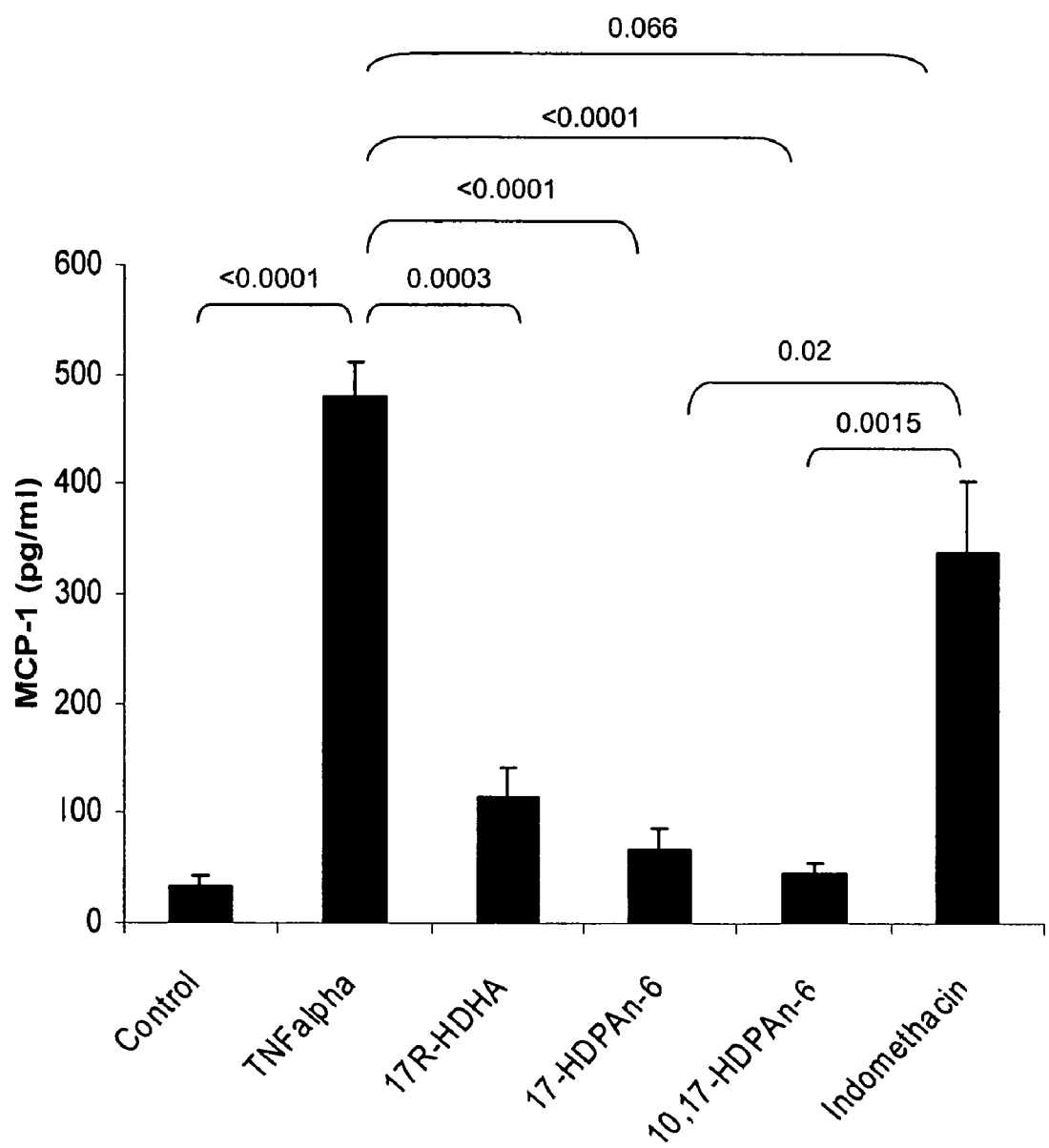

FIG. 20C shows the macrophage chemotactic protein-1 (MCP-1) concentrations in air pouch exudates. Both 17-hydroxy DPAn-6 and 10,17-dihydroxy DPAn-6 resulted in significant reductions in the secretion of this chemoattractant cytokine, and both compounds resulted in a larger inhibition of MCP-1 secretion than indomethacin.

FIGS. 20A-C indicate that the two DPAn-6 oxylipin derivatives 17-hydroxy DPAn-6 and 10,17-dihydroxy DPAn-6 are potent anti-inflammatory agents, resulting in reduced immune cell migration in this inflammation model. A reduction in key pro-inflammatory cytokines may contribute to this anti-inflammatory activity. Notably, there are differences between the activity of these two DPAn-6 oxylipins in their effect on cytokine production (e.g., IL-1β), suggesting that one compound may be more suitable than the other for specific applications (e.g., sepsis vs swelling). 17-hydroxy DPAn-6 is more potent than the DHA-derived oxylipin for inhibiting cell migration and 10,17-dihydroxy DPAn-6 is more potent than the DHA oxylipin for reduction in IL-1β secretion.

Example 16

The following example shows the anti-inflammatory effect of DHA and DPAn-6-derived docosanoids in cell culture.

Figure 21:
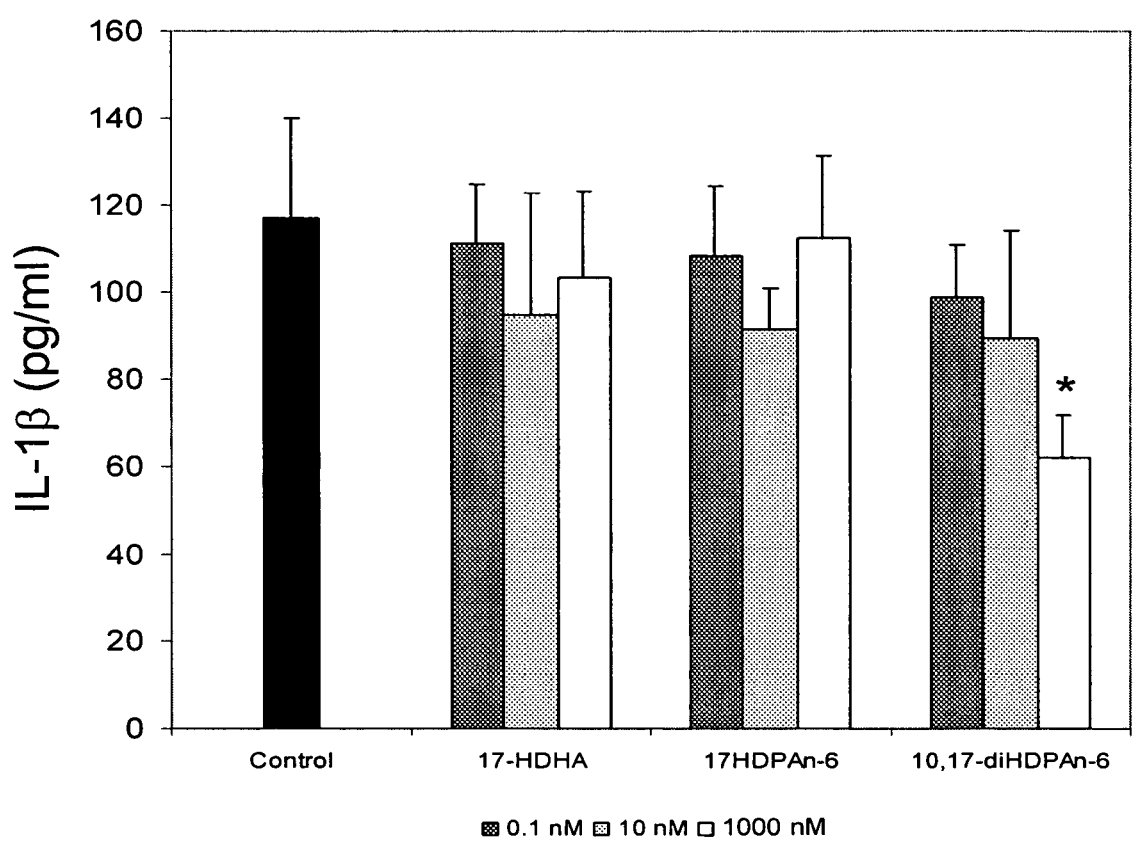

Effect of Docosanoids on TNFα-induced IL-1β Production by Glial Cell: Human glial cells (DBGTRG-05MG, ATCC, Manassas, Va.) were cultured for 24 hrs in 96-well culture dishes ($10^5$ cells per well) in 0.2 ml RPMI-medium containing supplements and serum (as specified by ATCC) after which the medium was replaced with fresh medium containing docosanoids or vehicle (PBS) followed within 5 minutes by addition of human recombinant TNFα (Sigma-Aldrich, St. Louis, Mo.) at a final concentration of 100 ng/ml. Cells were incubated for 17 hrs before supernatants were removed and cells were lysed with 0.2% Triton-X100 in PBS. Cell lysates were assayed for IL-1β using a commercial ELISA kit (R&D Systems, Minneapolis, Minn.) (FIG. 21). Bars represent means (n=3)±stdev. *p=0.06 compared to control using t-sided Student's t test. 17-HDHA: 17R-hydroxy DHA; 17HDPAn-6: 17-hydroxy DPAn-6; 10,17-diHDPAn-6: 10,17-dihydroxy DPAn-6.

Example 17

The following example further illustrates the anti-inflammatory effect of 10,17-dihydroxy DPAn-6 on human lymphocytes in culture and demonstrates that the dihydroxy DPAn-6 compound is more potent than the DHA analog (10,17,dihydroxy DHA) in reducing TNFα secretion by T lymphocytes stimulated with anti-CD3/anti-CD28 antibodies.

Figure 22A:
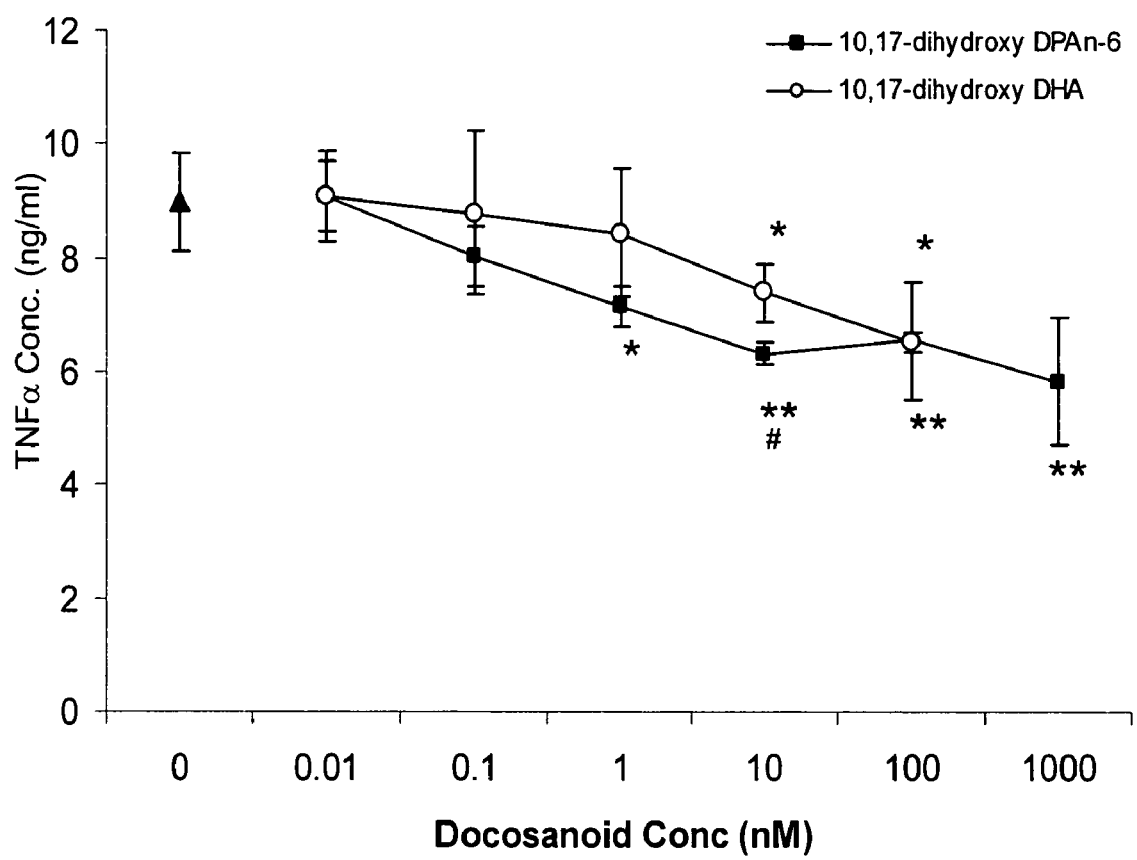

FIG. 22A: Effect of Docosanoids on TNFα Secretion by Human T Lymphocytes. The assay was performed essentially as described in Ariel et al, 2005. Briefly, human peripheral blood mononuclear cells were isolated from venous blood by Ficoll-Paque™ Plus (Amersham biosciences) gradient. T lymphocytes were isolated using a human T cell enrichment column (R&D Systems) per manufacturer's instructions. Purified T cells were treated with 10,17-dihydroxy DPAn-6 or 10,17-dihydroxy DHA or vehicle (0.05% ethanol) in RPMI-1640 media containing 10% heat inactivated fetal bovine serum for 6 hrs at 37° C. Lymphocytes (200,000 cells in 200 µl media per well) were then transferred to 96-well plates coated with both anti-CD3 antibody and anti-CD28 antibody (100 µl of 2 µg/ml of each antibody overnight to coat wells) and incubated for 41 hrs. TNFα concentrations were determined in cell supernatants by ELISA (R&D Systems). Group means±stdev (n=4) were compared by Student's t test. *p<0.05 and **p<0.01 compared to control; # indicates statistical difference (p=0.037) between the groups treated with 10,17-dihydroxy DPAn-6 and 10,17-dihydroxy DHA at the 10 nM concentrations.

Figure 22B:
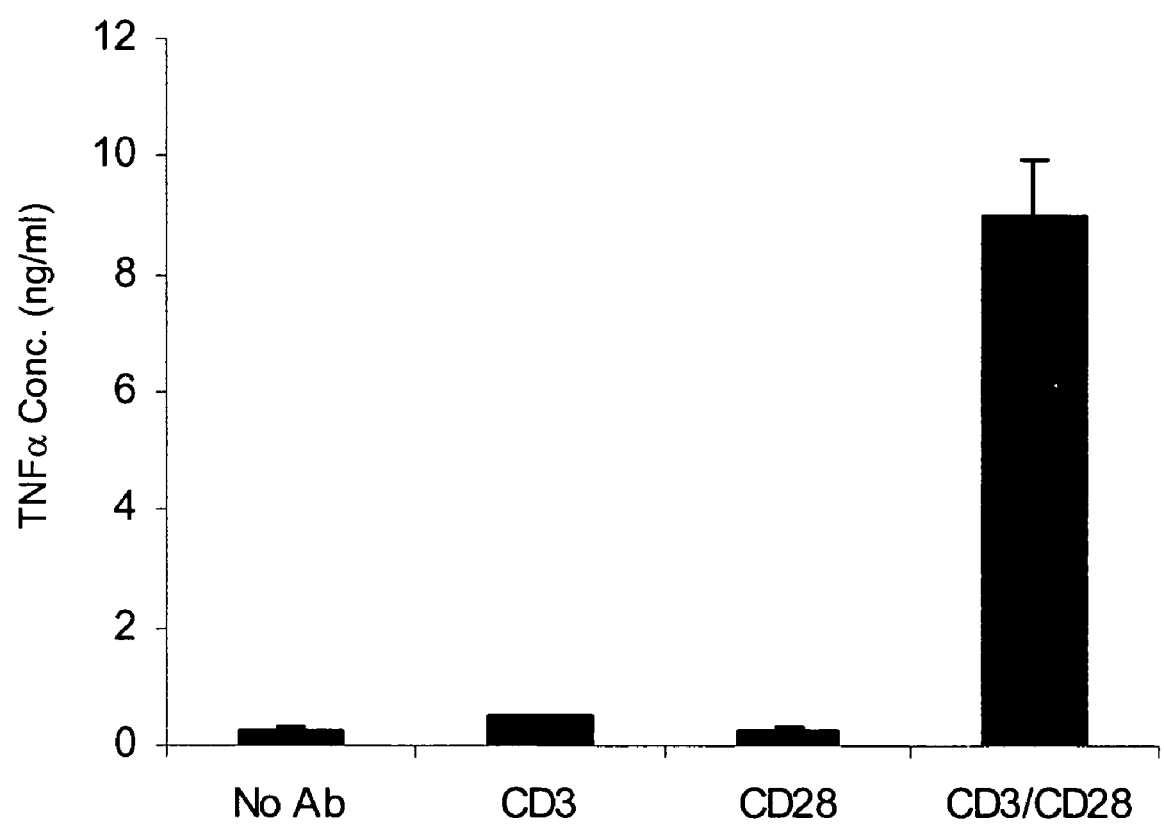
Figure 23:
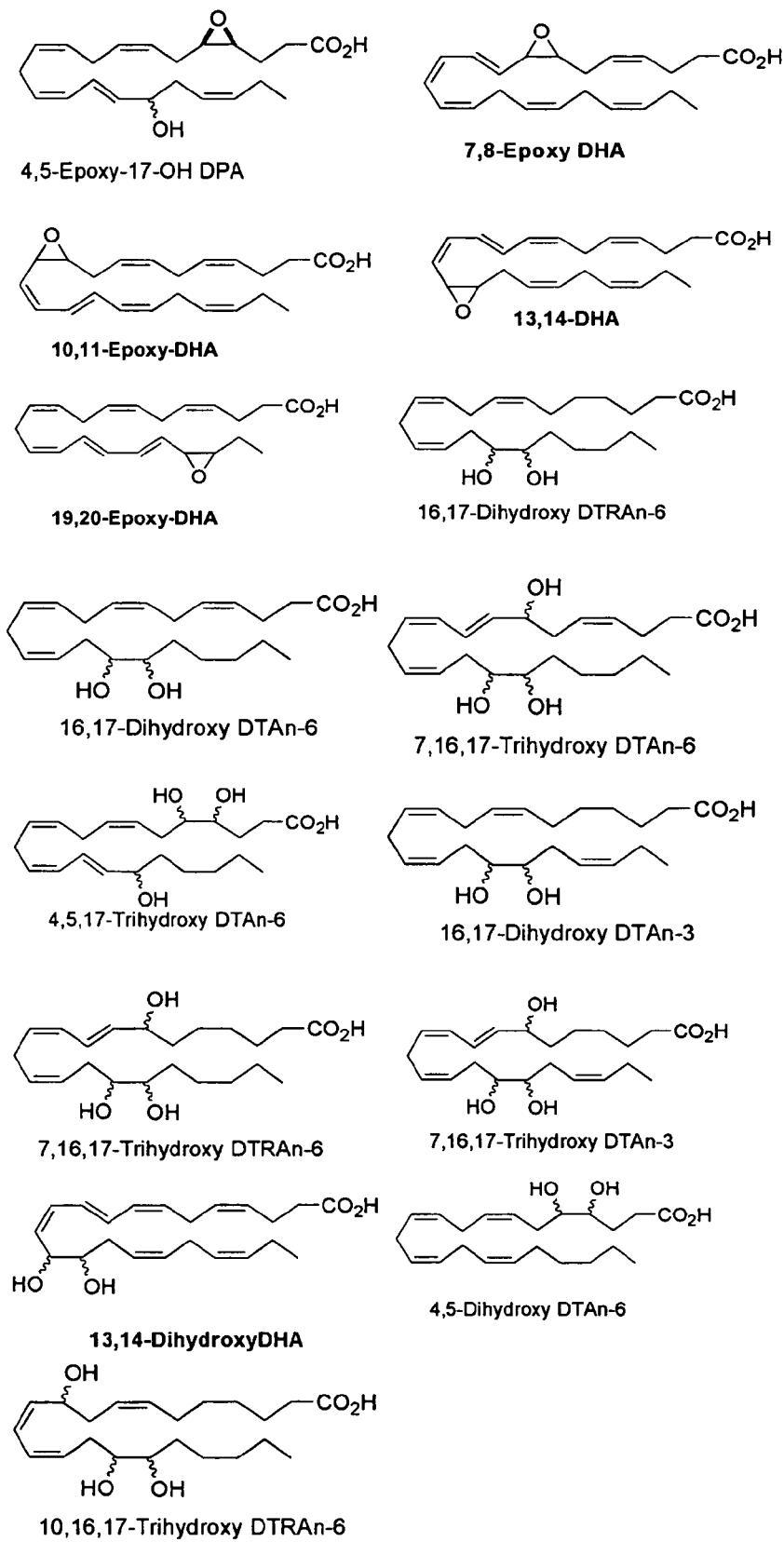

FIG. 22B shows the TNFα concentration in supernatants from lymphocytes not treated with docosanoids that were cultured in uncoated wells or in wells coated with anti-CD3 antibody only, with anti-CD28 antibody only or with a combination of the two antibodies.

REFERENCES

Ariel et al (2005). The docosoatriene prototectin D1 is produced by Th2-skewing and promotes human T cell apoptosis via lipid-raft clustering. JBC Papers in Press, Manuscript M509796200.

Arita et al. (2005a). The contributions of aspirin and microbial oxygenase to the biosynthesis of anti-inflammatory resolvins: Novel oxygenase products from omega-3 polyunsaturated fatty acids. Biochem Biophys Res Commun. 2005 (in press)

Arita et al. (2005b). Resolvin E1, an endogenous lipid mediator derived from omega-3 eicosapentaenoic acid, protects against 2,4,6-trinitrobenzene sulfonic acid-induced colitis. Proc Natl Acad Sci USA, 102(21):7671-6.

Arita et al. (2005c). Stereochemical assignment, anti-inflammatory properties, and receptor for the omega-3 lipid mediator resolvin E1. J Exp Med. 201(5):713-22

Bannenberg et al. (2005a). Molecular circuits of resolution: formation and actions of resolvins and protectins. J Immunol. 174(7):4345-55. Erratum in: J Immunol. 2005 May 1; 174(9):5884.

Bannenberg et al. (2005b). Molecular circuits of resolution: formation and actions of resolvins and protectins. J Immunol. 174(7):4345-55

Bazan (2005a). Lipid signaling in neural plasticity, brain repair, and neuroprotection. Mol Neurobiol. 32(1):89-103.

Bazan (2005b). Neuroprotectin D1 (NPD1): a DHA-derived mediator that protects brain and retina against cell injury-induced oxidative stress. Brain Pathol. (2):159-66.

Bazan et al. (2005). Brain response to injury and neurodegeneration: endogenous neuroprotective signaling. Ann N Y Acad Sci. 1053:137-47

Belayev et al. (2005). Docosahexaenoic acid complexed to albumin elicits high-grade ischemic neuroprotection. Stroke. 36(1):118-23.

Bouarab et al. (2004). The innate immunity of a marine red alga involves oxylipins from both the eicosanoid and octadecanoid pathways. Plant. Physiol. 135:1838-1848.

Butovich et al 2005. On the structure, synthesis and mechanism of formation of neuroprotectin D1-a novel anti-inflammatory compound of docosahexaenoic acid family. J Lipid Res. 2005 (in press)

Chen & Bazan (2005). Lipid signaling: sleep, synaptic plasticity, and neuroprotection. Prostaglandins Other Lipid Mediat. 77(1-4):65-76.

Flower and Perretti (2005). Controlling inflammation: a fat chance? J Exp Med. 201(5):671-4.

Gerwick (1994). Structure and biosynthesis of marine algal oxylipins. Biochimica et Biophysica Acta 1221:243-255.

Gerwick & Bemart (1993). Eicosanoids and related compounds from marine algae. Pages 101-150 in, Zaborski and Attaway (eds) Marine Biotechnology Vol. 1: Pharmaceutical and bioactive products. Plenum Press, NY.

Gerwick et al. 1993. Biologically active oxylipins from seaweeds. Hydrobiologia 260/261:653-665.

Gilroy et al (2004). Inflammatory resolution: new opportunities for drug discovery. Nature Reviews 3:401-416.

Guilford et al (2004). Novel 3-oxa lipoxin A4 analogues with enhanced chemical and metabolic stability have anti-inflammatory activity in vivo. J Med Chem. 2004 Apr. 8; 47(8):2157-65.

Hong et al. (2003). Novel docosatrienes and 17S-resolvins generated from docosahexaenoic acid in murine brain, human blood, and glial cells. Autacoids in anti-inflammation. J Biol Chem, 278(17):14677-87.

Lukiw et al. (2005). A role for docosahexaenoic acid-derived neuroprotectin D1 in neural cell survival and Alzheimer disease. J Clin Invest. 2005 (in press)

Marcjeselli et al. (2003). Novel docosanoids inhibit brain ischemia-reperfusion-mediated leukocyte infiltration and pro-inflammatory gene expression. J Biol Chem. 278(44): 43807-17.

Meydani (1990) Dietary modulation of cytokines and biological functions. Nutrition Reviews 48:361-367.

Mukherjee et al. (2004). Neuroprotectin D1: a docosahexaenoic acid-derived docosatriene protects human retinal pigment epithelial cells from oxidative stress. Proc Natl Acad Sci USA. 101(22):8491-6.

Rodriguez and Spur (2004) First total synthesis of 7(S), 16(R),17(S)-Resolvin D2, a potent anti-inflammatory lipid mediator. Tetrahedron Letters 45:8717-8720.

Rodriguez and Spur (2005) First total synthesis of 7(s),17(S)-Resolvin D5, a potent anti-inflammatory docosanoid. Tetrahedron Letters 46(21): 3623-7.

Rorrer et al. (1996). Development and bioreactor cultivation of a novel semidifferentiated tissue suspension derived from the marine plant *Acrosiphonia coalita*. Biotechnology and Bioengineering 49:559-567.

Rorrer et al. (1997). Production of hydroxyl fatty acids by cell suspension cultures of the marine brown alga *Laminaria saccharina*. Phytochemistry 46(5):871-877.

Serhan et al. (2004a). Resolvins, docosatrienes, and neuroprotectins, novel omega-3-derived mediators, and their endogenous aspirin-triggered epimers. Lipids. 39(11):1125-32.

Serhan et al. (2004b). Resolvins, docosatrienes, and neuroprotectins, novel omega-3-derived mediators, and their aspirin-triggered endogenous epimers: an overview of their protective roles in catabasis. Prostaglandins Other Lipid Mediat. 73(3-4):155-72.

Simopoulos (2002). Omega-3 fatty acids in inflammation and autoimmune diseases. J Am Coll Nutr 21(6): 495-505.

Ye et al (2002). Cytochrome P-450 epoxygenase metabolites of docosahexaenoate potently dilate coronary arterioles by activating large-conductance calcium-activated potassium channels. J Pharmacol Therapeut 303(2): 768-76.

Each reference described or cited herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated tri-hydroxy derivative of DPAn-6 selected from the group consisting of 7,16,17-trihydroxy DPAn-6; and 4,5,17-trihydroxy DPAn-6.

2. A composition comprising at least one tri-hydroxy docosanoid of claim 1.

3. The composition of claim 2, wherein the composition is a therapeutic composition, a nutritional composition, or a cosmetic composition.

4. The composition of claim 2, further comprising aspirin.

5. The composition of claim 2, further comprising a compound selected from the group consisting of: DPAn-6, DPAn-3, DTAn-6, DHA, EPA, an oxylipin derivative of DHA and an oxylipin derivative of EPA.

6. The composition of claim 2, further comprising at least one agent selected from the group consisting of: a statin, a non-steroidal anti-inflammatory agent, an antioxidant, and a neuroprotective agent.

7. The composition of claim 2, wherein the composition comprises an oil selected from the group consisting of a microbial oil, a plant seed oil, and an aquatic animal oil.

* * * * *